US008945482B2

(12) United States Patent
Mitragotri et al.

(10) Patent No.: US 8,945,482 B2
(45) Date of Patent: Feb. 3, 2015

(54) SYSTEM, METHOD AND DEVICE FOR TISSUE-BASED DIAGNOSIS

(75) Inventors: Samir Mitragotri, Santa Barbara, CA (US); Sumit Paliwal, Goleta, CA (US); Makoto Ogura, Ryugasaki (JP)

(73) Assignee: The Regents of the University of California, Oakland, CA (US)

( * ) Notice: Subject to any disclaimer, the term of this patent is extended or adjusted under 35 U.S.C. 154(b) by 750 days.

(21) Appl. No.: 13/126,105

(22) PCT Filed: Feb. 12, 2010

(86) PCT No.: PCT/US2010/024010
§ 371 (c)(1),
(2), (4) Date: Apr. 26, 2011

(87) PCT Pub. No.: WO2010/093861
PCT Pub. Date: Aug. 19, 2010

(65) Prior Publication Data
US 2011/0212485 A1 Sep. 1, 2011

Related U.S. Application Data

(60) Provisional application No. 61/152,585, filed on Feb. 13, 2009.

(51) Int. Cl.
*G01N 1/28* (2006.01)
*A61B 10/02* (2006.01)
(Continued)

(52) U.S. Cl.
CPC ............ *A61B 10/02* (2013.01); *A61M 37/0015* (2013.01); *G01N 1/286* (2013.01);
(Continued)

(58) Field of Classification Search
USPC ................................ 422/63–67, 536; 436/180
See application file for complete search history.

(56) References Cited

U.S. PATENT DOCUMENTS

| 4,268,613 A | 5/1981 | Okishi |
| 5,398,690 A | 3/1995 | Batten et al. |

(Continued)

FOREIGN PATENT DOCUMENTS

| CN | 101115449 A | 1/2008 |
| EP | 0743519 A2 | 11/1996 |
| JP | 2006-167428 | 6/2006 |

OTHER PUBLICATIONS

Ayliffe, et al. "Hand disinfection: a comparison of various agents in laboratory and ward studies" J. Hospital Infection, 1988, 11, 226-243.
(Continued)

*Primary Examiner* — Jill Warden
(74) *Attorney, Agent, or Firm* — Pabst Patent Group LLP

(57) ABSTRACT

The current invention provides devices, methods and systems involving application of energy and/or a liquefaction promoting medium to a tissue of interest to generate a liquefied sample comprising tissue constituents so as to provide for rapid tissue sampling, tissue decontamination as well as qualitative and/or quantitative detection of analytes that may be part of tissue constituents (e.g., several types of biomolecules, drugs, and microbes). In addition, the current invention provides specific compositions of the said liquefaction promoting medium so as to facilitate liquefaction, preserve liquefied tissue constituents, and enable delivery of molecules into tissues. Determination of tissue composition in the liquefied tissue sample can be used in a variety of applications, including diagnosis or prognosis of local as well as systemic diseases, evaluating bioavailability of therapeutics in different tissues following drug administration, forensic detection of drugs-of-abuse, evaluating changes in the tissue microenvironment following exposure to a harmful agent, and various other applications. The methods, devices and systems are used to deliver one or more drugs through or into the site of the tissue to be liquefied.

20 Claims, 24 Drawing Sheets

(51) Int. Cl.
| | |
|---|---|
| *A61M 37/00* | (2006.01) |
| *G01N 1/40* | (2006.01) |
| *A61B 10/00* | (2006.01) |
| *A61B 10/04* | (2006.01) |
| *A61B 18/20* | (2006.01) |
| *A61B 17/00* | (2006.01) |
| *A61B 17/32* | (2006.01) |
| *A61B 18/00* | (2006.01) |
| *A61N 7/02* | (2006.01) |
| *G01N 1/44* | (2006.01) |

(52) U.S. Cl.
CPC .......... *G01N 1/4044* (2013.01); *A61B 10/0045* (2013.01); *A61B 10/0096* (2013.01); *A61B 10/0283* (2013.01); *A61B 10/04* (2013.01); *A61B 18/20* (2013.01); *A61B 2017/00761* (2013.01); *A61B 2017/320004* (2013.01); *A61B 2018/00452* (2013.01); *A61M 2037/0023* (2013.01); *A61M 2037/0046* (2013.01); *A61N 7/02* (2013.01); *G01N 1/44* (2013.01)
USPC .......................................... 422/536; 436/180

(56) References Cited

U.S. PATENT DOCUMENTS

| | | | |
|---|---|---|---|
| 5,492,126 | A | 2/1996 | Hennige et al. |
| 5,739,432 | A | 4/1998 | Sinha |
| 5,804,452 | A | 9/1998 | Provonost et al. |
| 5,913,833 | A | 6/1999 | Elstrom et al. |
| 6,007,497 | A | 12/1999 | Huitema |
| 6,093,551 | A | 7/2000 | Raithel et al. |
| 6,165,500 | A | 12/2000 | Cevic |
| 6,544,211 | B1 | 4/2003 | Andrew et al. |
| 6,560,478 | B1 | 5/2003 | Alfano et al. |
| 6,589,173 | B1 | 7/2003 | Mitragotri |
| 7,709,193 | B2* | 5/2010 | Van Eyk et al. ............ 435/6.16 |
| 2002/0082518 | A1 | 6/2002 | Weiss et al. |
| 2002/0188280 | A1* | 12/2002 | Nguyen et al. ................ 604/542 |
| 2003/0060818 | A1 | 3/2003 | Kannenberg et al. |
| 2003/0143116 | A1 | 7/2003 | Zheng et al. |
| 2003/0211520 | A1 | 11/2003 | Afar et al. |
| 2004/0151745 | A1 | 8/2004 | Zimmer et al. |
| 2005/0164903 | A1 | 7/2005 | Ko et al. |
| 2005/0214825 | A1 | 9/2005 | Stuelpnagel |
| 2006/0046261 | A1 | 3/2006 | Porter et al. |
| 2006/0100569 | A1 | 5/2006 | McRury et al. |
| 2006/0116563 | A1 | 6/2006 | Asano et al. |
| 2006/0165823 | A1 | 7/2006 | Herrera |
| 2006/0166222 | A1 | 7/2006 | Lu et al. |
| 2007/0055181 | A1 | 3/2007 | Deem et al. |
| 2007/0055261 | A1 | 3/2007 | Reiley et al. |
| 2007/0059687 | A1 | 3/2007 | Ohno et al. |
| 2007/0173448 | A1 | 7/2007 | Shah et al. |
| 2007/0183936 | A1* | 8/2007 | Newsam et al. ............ 422/102 |
| 2008/0114418 | A1 | 5/2008 | Myeong et al. |
| 2008/0119831 | A1 | 5/2008 | Myeong et al. |
| 2009/0325837 | A1 | 12/2009 | Mundschau et al. |
| 2010/0261176 | A1 | 10/2010 | Mitragotri et al. |
| 2011/0212485 | A1 | 9/2011 | Mitragotri et al. |
| 2011/0262892 | A1 | 10/2011 | Aoyagi et al. |
| 2012/0004592 | A1 | 1/2012 | Mitragotri et al. |

OTHER PUBLICATIONS

Written Opinion of the International Searching Authority from related PCT Application No. PCT/US08/72384.

International Search Report from related PCT Application No. PCT/US2012/038169, Published as WO2013172832.

Sugimura et al., Transgenic *patchouli* plants produced by *Agrobacterium*-mediated transformation. Plant Cell, Tissue and Organ Culture (2005) 82: 251-257.

Zanten et al., Cerebrospinal fluid tumour markers in patients treated for meningeal malignancy. Journal of Neurology, Neurosurgery, and Psychiatry 1991;S4:119-123.

Guenthner et al., Gram-negative bacilli as nontransient flora on the hands of hospital personnel. J. Clin. Microbial. 1987, 25(3):488.

* cited by examiner

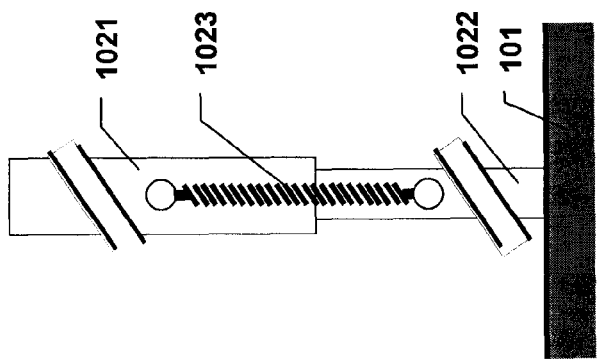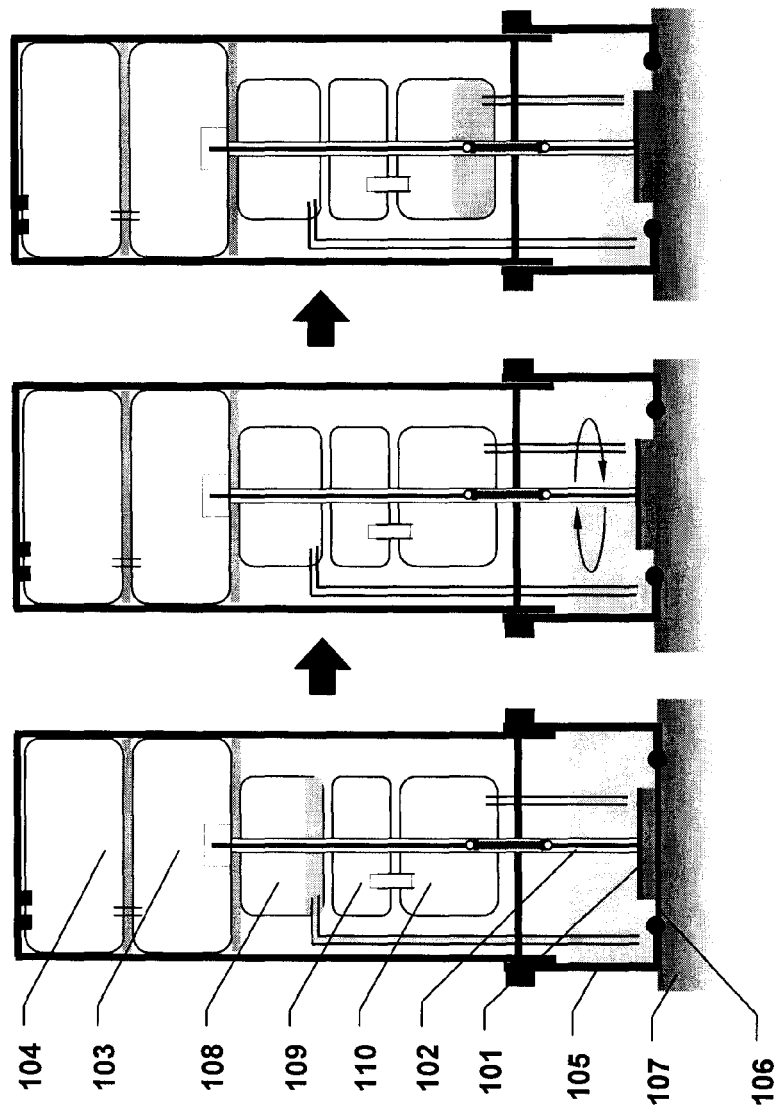

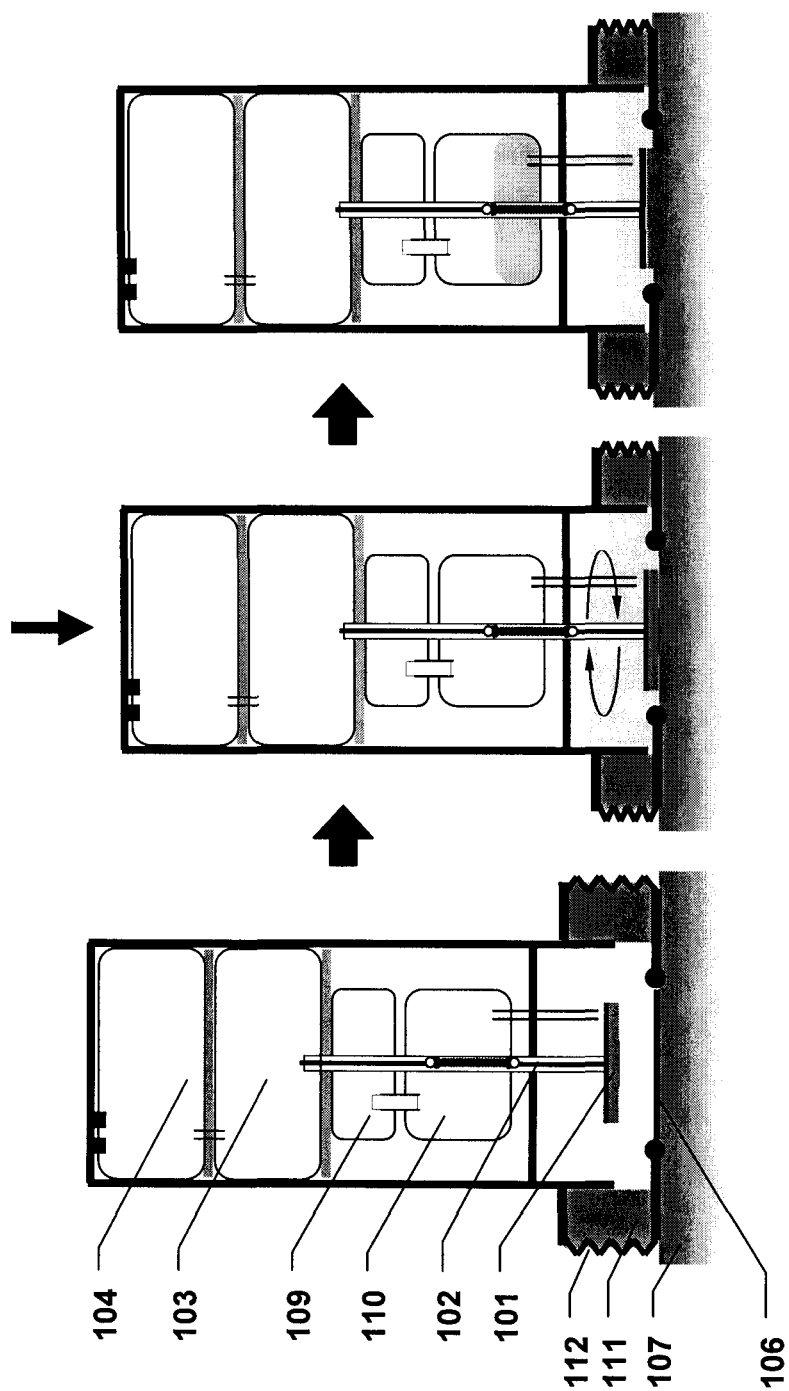

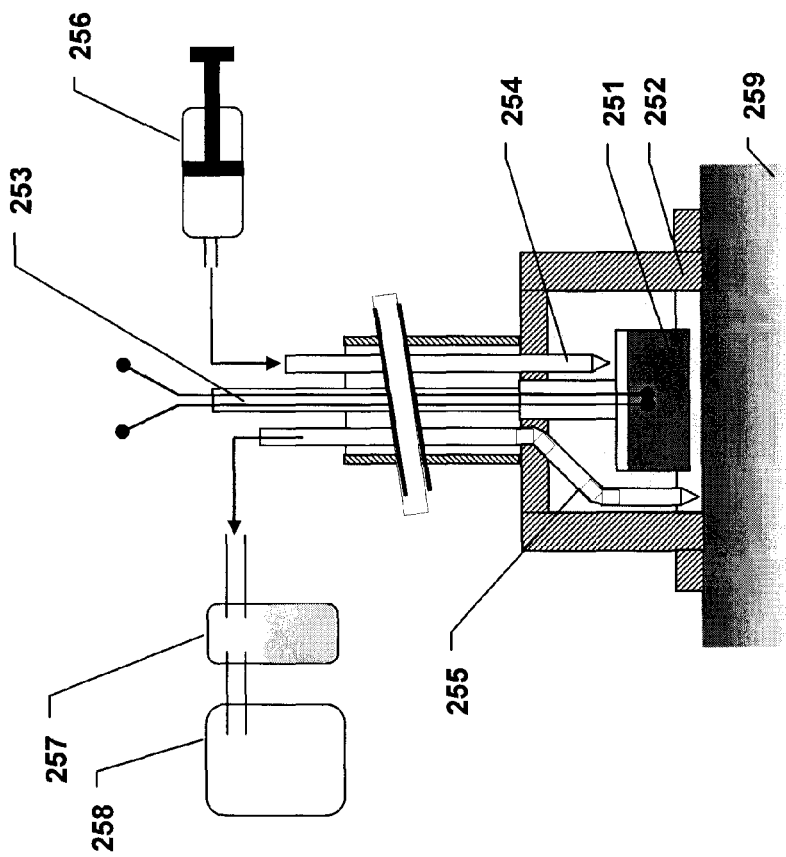
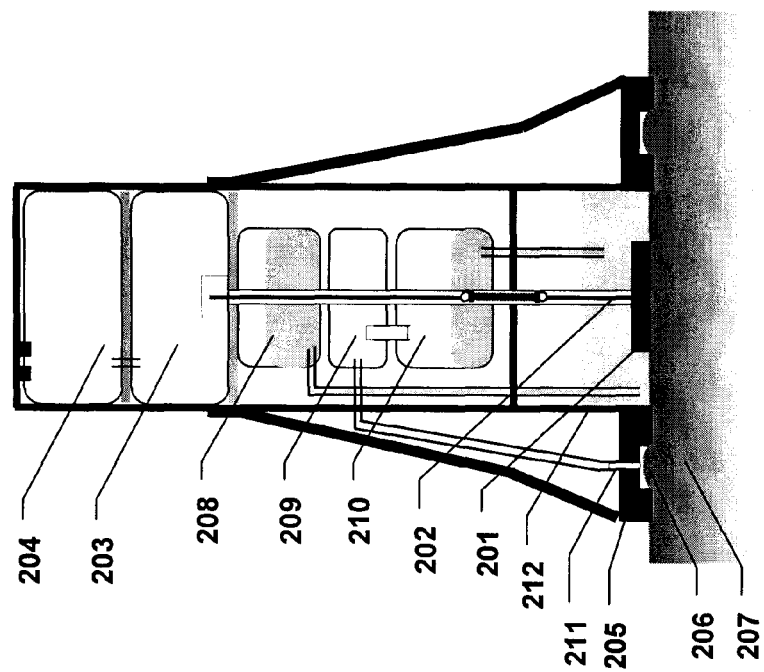
Figure 2b
Figure 2a

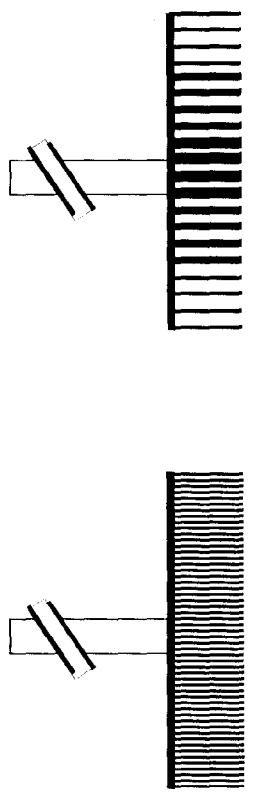
Figure 4a
Figure 4b
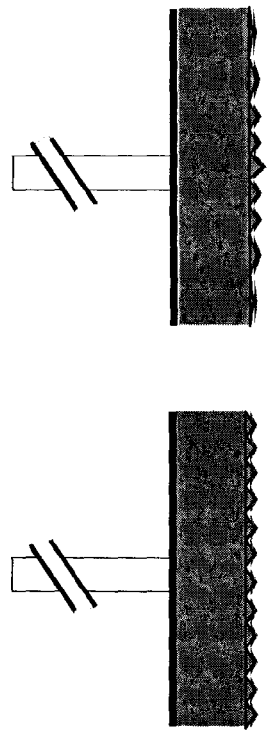
Figure 4e
Figure 4f
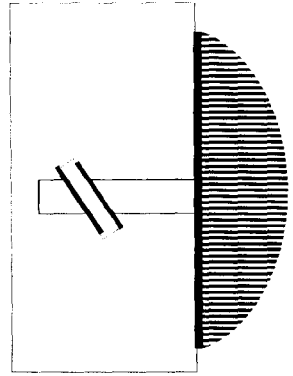
Figure 4c
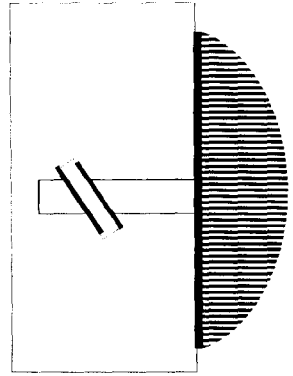
Figure 4d
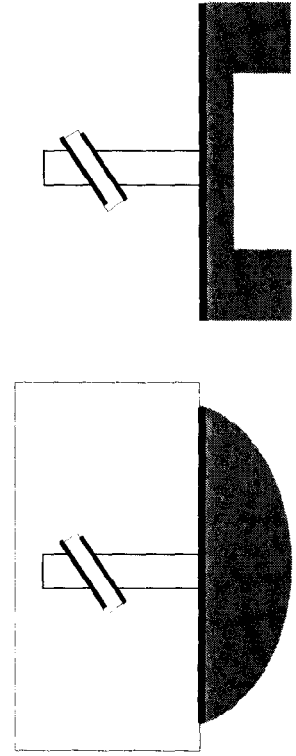
Figure 4g

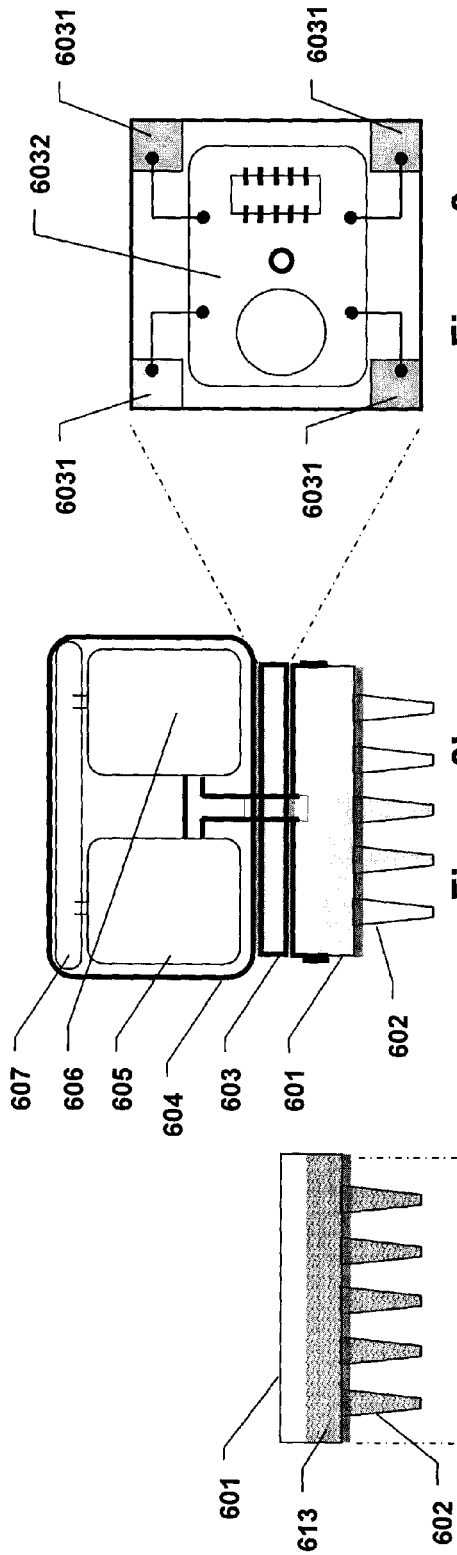
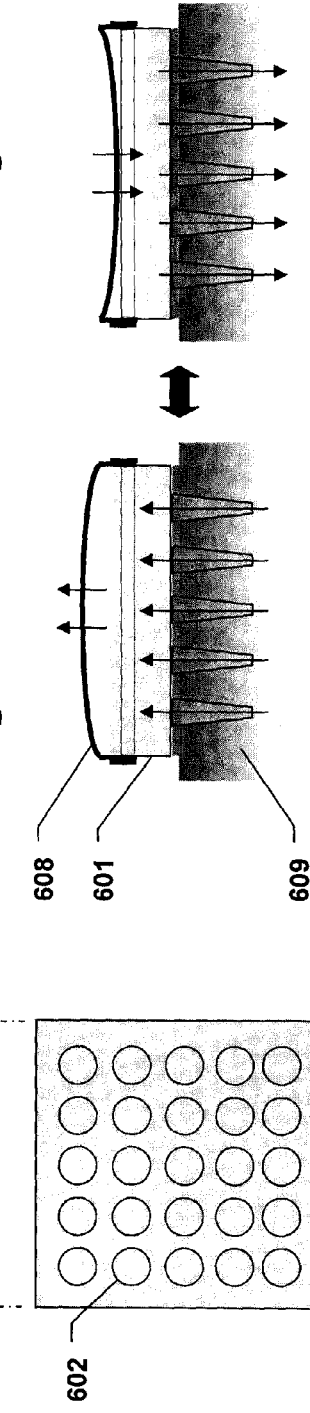
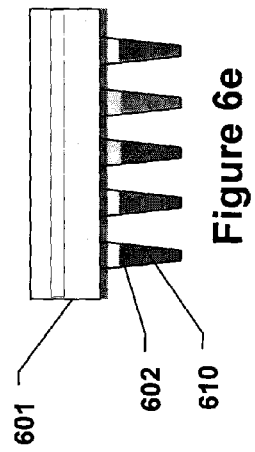
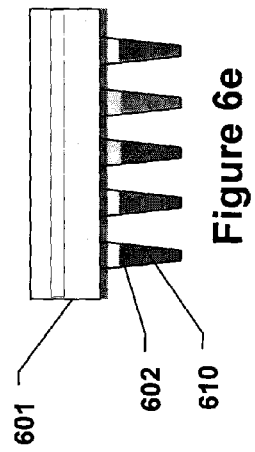
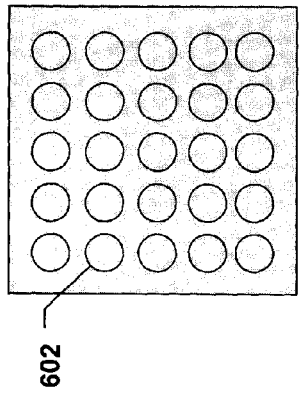

SYSTEM, METHOD AND DEVICE FOR TISSUE-BASED DIAGNOSIS

CROSS-REFERENCE TO RELATED APPLICATIONS

This application claims the benefit of U.S. Provisional Patent Application No. 61/152,585, filed Feb. 13, 2009, which is incorporated by reference in its entirety.

BACKGROUND OF THE INVENTION

The biomolecular composition of human tissues, represented by a multitude of lipids, proteins, nucleic acids, and other miscellaneous molecules, is a sensitive indicator of local pathologies, such as cancer, allergies, and eczema, as well as several systemic diseases, such as cardiovascular disease, Alzheimer's disease, and diabetes. In addition, tissue molecular composition also holds critical information about the body's exposure to exogenous chemical and biological entities. However, this information is not currently used in diagnostic methods due to a lack of patient-friendly and standardized methods for routine sample collection from tissues. Instead, clinical diagnosis is invariably performed by visual observation and histopathological analysis of tissue biopsies, which are highly limited due to their qualitative nature, leading to increased misdiagnosis and inappropriate use. In addition to being invasive, current methods also fall short in explaining a complete molecular genesis of diseases, and fail to distinguish between diseases.

Prior approaches using physical and chemical methods for assessing tissue fluid have focused chiefly on extracting a few low molecular weight molecules that are freely present in the interstitial fluid, such as calcium and glucose. Use of tape stripping for physically harvesting superficially-lying tissue constituents with an adhesive tape has been reported; however this technique has been shown to be limited by inefficacy, lack of a standardized protocol, and high heterogeneity in tissue sampling.

BRIEF SUMMARY OF THE INVENTION

The current invention describes system, method and device, as well as compositions useful in such systems, methods and devices, involving application of energy to a tissue of interest to generate a liquefied sample comprising tissue constituents so as to provide for rapid tissue sampling, as well as qualitative and/or quantitative detection of analytes that may be part of tissue constituents (e.g., several types of biomolecules, drugs, and microbes). Determination of tissue composition can be used in a variety of applications, including diagnosis or prognosis of diseases, evaluating bioavailability of therapeutics in different tissues following drug administration, forensic detection of drugs-of-abuse, evaluating changes in the tissue microenvironment following exposure to a harmful agent, tissue decontamination and various other applications.

The current invention provides methods and devices for generating a liquefied tissue sample from a subject—living or diseased. The device and method involve applying energy and a liquefaction promoting medium to a tissue of interest of a subject, the applying producing a liquefied tissue sample, and collecting the liquefied tissue sample. In some embodiments, an analysis for the presence or absence of at least one analyte in the liquefied tissue sample is performed, wherein the analysis facilitates diagnosis of a condition of interest. In certain embodiments, the analysis involves generating an analyte profile from the liquefied tissue sample and comparing the analyte profile to a reference analyte profile, wherein the comparing facilitates diagnosis of a condition of interest.

In some embodiments, the purpose of said tissue liquefaction is to remove, or decontaminate the tissue from undesired substances. Non-limiting examples of such undesired substances include chemicals, environmental contaminants, biological toxins, and in general substances that are considered toxic or hazardous to the body. In certain embodiments, the said method of decontamination is performed by continuously moving the tissue liquefaction device over tissue-of-interest until removal of undesired substances at a preferred level is attained.

In some embodiments, the liquefaction promoting agent comprises of one of more of sodium chloride, potassium chloride, sodium phosphate dibasic, potassium phosphate monobasic, 3-{[tris(hydroxymethyl)methyl]amino}propanesulfonic acid, N,N-bis(2-hydroxyethyl)glycine, tris (hydroxymethyl) methylamine, N-tris(hydroxymethyl)methylglycine, 4-2-hydroxyethyl-1-piperazineethanesulfonic acid, 2-{[tris(hydroxymethypmethyl]amino}ethanesulfonic acid, 3-(N-morpholino)propanesulfonic acid, piperazine-N,N'-bis(2-ethanesulfonic acid), dimethylarsinic acid, saline sodium citrate, 2-(N-morpholino)ethanesulfonic acid. In certain embodiments, the liquefaction promoting agent comprises of one or more of a protease inhibitor, an RNase inhibitor, or a DNase inhibitor. In certain embodiments, the liquefaction promoting agent comprises at least one of free radical scavenger, a defoaming agent, and a protein stabilizer. In certain embodiments, the liquefaction promoting agent comprises at least one of Brij-30, 3-(Decyl dimethyl ammonio) propane sulfonate (DPS), 3-(Dodecyl dimethyl ammonio) propane sulfonate (DDPS), N-lauroyl sarcosine (NLS), Triton X-100, Sodium Dodecyl Sulfate, DMSO, fatty acids, azone, EDTA, or sodium hydroxide. In certain embodiments, the liquefaction promoting agent comprises a suspension of abrasive particles. In certain embodiments, the abrasive particles comprise silica or aluminum oxide.

In some embodiments, the energy is applied in the form of ultrasound, mechanical, optical, thermal, or electrical energy. In certain embodiments, the mechanical energy is applied by an abrasive material. In certain embodiments, the thermal energy is applied in the form of radio frequency energy. In certain embodiments, the optical energy is applied in the form of a laser.

In some embodiments, the liquefied tissue sample is generated for each of a healthy tissue of interest of the subject and a suspected diseased tissue of interest of the subject, and the analysis comprises comparing analytical results from the healthy tissue sample with analytical results from the suspected diseased tissue sample, wherein the comparing facilitates diagnosis of a condition of interest. In some embodiments, the liquefied tissue sample is generated for multiple tissue sites and the analysis comprises comparing analytical results from the multiple tissue sites, wherein said comparing facilitates diagnosis of a condition of interest. In some embodiments, the liquefied tissue sample is collected from multiple tissue sites, and the samples are combined to make a diagnosis.

In some embodiments, the liquefied tissue sample is collected by aspiration. In certain embodiments, the collecting is by retaining the liquefaction agent in a housing placed in contact with the tissue. In certain embodiments, the collecting is by mechanized transfer of the liquefied tissue sample in a housing located in the device.

In some embodiments, the liquefied tissue sample is mixed with a substance which assists in further liquefaction and in stabilization of analytes of interest for storage or transportation. In certain embodiments, the transferred tissue sample from that sample container is mixed with the substances which are pre-stored in a container. Examples include a protein stabilizer such as protease inhibitor, a nucleic-acid stabilizer such as EDTA, phenol, nonspecific proteinase, an RNase inhibitor and a DNase inhibitor, a defoaming agent, and surfactants such as Triton X-100, Sodium Dodecyl Sulfate, and DMSO, and abrasive particles comprise silica or aluminum oxide.

In certain embodiments, the device evaluates the tissue of interest prior, during, or after liquefaction process. In certain embodiments, the evaluation is performed by electrochemical, biochemical, or optical means. In some embodiments, the evaluation involves measurement of tissue's electrical conductivity. In an exemplary embodiment, electrical conductivity is measured by a means applying an AC electrical signal across the tissue of interest. The said electrical signal has voltage between 0.1 mV and 10 V and frequency between 1 Hz and 100 kHz.

In some embodiments, the device involves detecting certain tissue constituents in the liquefied tissue sample prior to analysis of an analyte of interest, such as a disease marker. In certain embodiments, the detecting is by electrochemical, biochemical, or optical means. In some embodiments the electrochemical means of detecting is an ion-elective electrode. In some embodiments the optical means of detecting is measuring the absorption or scattering coefficient of a liquid solution.

In some embodiments, the energy is applied to a tissue in the form of ultrasound with a mechanical index between 0.1 and 50. In certain embodiments, the energy is applied by contacting the tissue with a moving abrasive surface. In certain embodiments, the energy is applied to the tissue by contacting the tissue with a moving brushing device comprising a plurality of bristles. In certain embodiments, the energy is applied to the tissue by mechanical insertion of a patch bearing plurality of micro-needles into the tissue; and further injection of liquefaction medium through the micro-needles into the tissue. In some embodiments, additional energy is applied by moving the said micro-needle patch after its insertion into the tissue. In certain embodiments, the energy is applied to the tissue by mechanized stirring of the liquefaction agent. In certain embodiments, the energy is applied to the tissue by contacting the tissue with a high velocity jet comprising of liquefaction promoting medium, which may also contain abrasive particles in different embodiments.

In some embodiments, the tissue comprises breast, prostate, eye, vagina, bladder, nail, hair, colon, testicles, or intestine. In certain embodiments, the tissue comprises skin or a mucosal membrane. In certain embodiments, the tissue comprises lung, brain, pancreas, liver, heart, bone, or aorta wall.

In some embodiments, the analyte comprises a small molecule, a drug or metabolite thereof, a polypeptide, a lipid, a nucleic acid, or a microbe. In certain embodiments, the analyte comprises an antibody, a cytokine, an illicit drug, or a cancer biomarker.

In some embodiments, the liquefied tissue sample is held in a container, and the analyte profile is generated by integrating the liquid container with one or more analytical devices. In certain embodiments, the tissue liquefaction device contains a means for measuring the concentration of a calibrator analyte to provide a means for calibrating the analysis of the analyte.

In some embodiments, the device involves diagnosing allergic disease in a subject, and the device comprises means for analyzing the liquefied tissue sample for the presence or absence of IgE and IgG antibodies, cytokines such as IL4, IL5, IL10, IL-12, IL13, IL-16, GM-CSF, RANTES, MCP-4, CTACK/CCL27, IFN-g, TNFa, CD23, CD-40, Eotaxin-2, and TARC, wherein the analysis facilitates diagnosis of allergic disease in the subject.

In some embodiments, the device involves diagnosing cancer in a subject, and the device comprises means for analyzing the liquefied tissue sample for the presence or absence of one or more cancer markers, wherein the analysis facilitates diagnosis of cancer in the subject. In certain embodiments, the tissue of interest is breast, colon, prostate, skin, testicle, intestine, or mouth.

In some embodiments, the device involves diagnosing heart disease in a subject, and the device comprises means for analyzing the liquefied tissue sample for the presence or absence of one or more of cholesterol, triglycerides, lipoproteins, free fatty acids, and ceramides, wherein the analysis facilitates diagnosis of heart disease in the subject.

In some embodiments, the device involves detecting the presence of an illicit drug, or metabolite thereof, in a subject, and the device comprises means for analyzing the liquefied tissue sample for the presence or absence of an illicit drug, or metabolites thereof, wherein the analysis provides for detection of illicit drugs in the subject.

In some embodiments, the device involves detecting a microorganism in a subject, and the device comprises means for applying energy and a liquefaction medium to a tissue of interest in a subject and analyzing the liquefaction medium for the presence or absence of a microorganism, wherein the analysis provides for detection of the presence or absence of a microorganism.

Another object of the current invention is to provide a method and device for liquefying a tissue of a subject for facilitating the passage of a drug across or into the tissue. The method and device disclosed above are applicable not only to collection of tissue constituents but also to drug delivery. The device and method involve applying energy and a liquefaction medium to a tissue of interest of a subject, and delivering a drug through or into the site of the tissue to be liquefied. The advantage of using the present invention is 1) to provide higher fluxes of drugs into a tissue, and 2) to allow greater control of fluxes into a tissue. Drugs which would simply not pass through the tissues such as the skin are forced through the tissues when the method is applied.

In some embodiments, the present invention offers a method for delivering one or more drugs through the tissue to be liquefied into the circulatory system, which circumvents degradation in the gastrointestinal tract and rapid metabolism by the liver from which drugs to be routinely administered either orally or by injection suffer. In certain embodiments, the current invention provides a method and device for delivering one or more drugs locally to the tissue of interest, thus limiting side effects to the healthy tissues. The method and device may also be applicable for enhancing transport to cellular membranes.

In particular, the device of the present invention consists of the following major components: 1) an energy generator; 2) a liquefaction promoting medium; 3) a reservoir to hold drugs to be delivered and/or collect the liquefied tissue sample.

A drug to be administered can be added into the liquefaction medium prior or during tissue liquefaction process. In an alternate embodiment, application of energy is in combination of the liquefaction medium which does not contain a drug can be used for liquefying a tissue, and subsequently a drug in an appropriate carrier such as a patch can be applied on a site of the tissue to be liquefied.

The transport of drug into the tissue can be further enhanced by the simultaneous or subsequent application of a secondary driving force such as chemical permeability or transport enhancers, convection, osmotic pressure gradient, concentration gradient, iontophoresis, electroporation, magnetic field, ultrasound, or mechanical pressure. The driving force can be applied continuously over a period of time or at intervals during the period of liquefaction.

In some embodiments, the tissue to be administered comprises an organs as well as biological surfaces. In certain embodiment, the biological surfaces comprise a biological membrane and cellular membrane. In certain embodiment, the biological membrane comprises skin or a mucosal membrane. In certain embodiments, the biological membrane comprises a buccal membrane, eye, vagina, colon, or intestine. In some embodiment, the tissue comprises a diseased tissue.

In one embodiment, a device is provided that can be used on a tissue to obtain a liquefied sample comprising an energy source operably coupled to the tissue, and a chamber, operably coupled to said tissue, capable of delivering liquefaction promoting medium to and/or collecting said liquefied sample from said tissue.

In another embodiment, the device can be used on a tissue which is a part of a living organism; and the tissue can be excised from the organism prior to diagnosis.

In another embodiment, the device of claim 1 wherein the liquefied tissue sample is transferred to an assay for monitoring the presence or absence of at least one analyte.

In yet another embodiment, the chamber of the device can be a sponge-bellow assembly where the sponge is capable of storing said liquefaction promoting medium and/or liquefied tissue sample.

In another embodiment, a device is provided comprising an energy source operably coupled to the tissue, and a chamber, operably coupled to said tissue, capable of delivering liquefaction promoting medium to and/or collecting said liquefied sample from said tissue; also comprises a tube/needle, connected to said chamber, capable of delivering the liquefaction promoting medium to and/or aspirating liquefied tissue sample from the tissue.

In still another embodiment, a device is provided comprising an energy source operably coupled to the tissue, and a chamber, operably coupled to said tissue, capable of delivering liquefaction promoting medium to and/or collecting said liquefied sample from said tissue; also comprises a sample container, operably connected to said chamber, capable of storing aspirated liquefied tissue sample containing analytes, or transferring said aspirated liquefied tissue sample to an ancillary chamber; wherein the chamber is used only to deliver the liquefaction promoting medium to the chamber.

In another embodiment, a pressurized container and/or vacuum container is part of the device, which facilitates transfer of said liquefaction promoting medium and/or liquefied tissue sample.

In one embodiment, the energy emitted from the energy source in the deice is in the form of ultrasound, mechanical, optical, thermal, or electrical energy. In a particular embodiment, the mechanical energy is applied to the tissue by an abrasive material, vacuum, pressure or shear force. In another embodiment, the thermal energy is applied to the tissue in the form of radio frequency energy. In another embodiment, the optical energy is applied to the tissue in the form of a laser.

In yet another embodiment, a device is provided comprising an energy source operably coupled to the tissue, and a chamber, operably coupled to said tissue, capable of delivering liquefaction promoting medium to and/or collecting said liquefied sample from said tissue further comprising a sample container, operably connected to said chamber, capable of storing aspirated liquefied tissue sample containing analytes, or transferring said aspirated liquefied tissue sample to an ancillary chamber; wherein the chamber is used only to deliver the liquefaction promoting medium to the chamber.

In another embodiment, a device is provided comprising an energy source operably coupled to the tissue, and a chamber, operably coupled to said tissue, capable of delivering liquefaction promoting medium to and/or collecting said liquefied sample from said tissue, wherein the energy source comprises of a pad connected to a shaft.

In a more particular embodiment, the shaft has a pressure sensing unit, which maintains a predetermined pressure profile on to the tissue upon contact.

In another embodiment, the pad is selected from a group consisting of an abrasive surface and a patch comprising of a plurality of micro-needles.

In yet another embodiment, the device further comprises a plunger, operably connected to the top of the chamber.

In another embodiment, the device is divided into an upper and lower unit, and wherein the lower unit is detachable from said upper unit; wherein the upper unit comprises the energy source and the lower unit comprises the chamber.

In still another embodiment, the device further comprises an analytical unit operably connected to the chamber, and where the analytic unit is capable of performing temporal monitoring of the tissue sample by electrochemical, biochemical or optical means; or the analytic unit is capable of analyzing the analytes within said liquefied tissue sample.

In another embodiment, the device is connected to a diagnostic probe or a catheter; wherein the diagnostic probe is selected from a group consisting of endoscope, colonoscope, and laparoscope.

In still another embodiment, the use of the device results in situ liquefaction of the tissue sample.

In another embodiment, the device contains a liquefaction promoting medium that can preserve and enhance the detection of proteins, lipids and nucleic acids, comprising: 3-(decyl dimethyl ammonio) propane sulfonate (DPS) and polyethylene glycol dodecyl ether (Brij 30) dissolved in a buffered solution; and where the concentration of 3-(decyl dimethyl ammonio) propane sulfonate and polyethylene glycol dodecyl ether (B30) is between 0.01-10% (w/v); and where the 3-(decyl dimethyl ammonio) propane sulfonate and polyethylene glycol dodecyl ether are present at a ratio of 50:50.

In yet another embodiment, the liquefaction promoting medium within the device is buffered in a solution comprising either phosphate-buffered saline, Tris-buffered saline, Tris-HCL or EDTA.

In another embodiment, liquefaction promoting medium within the device comprises a nonionic surfactant selected from a Brij series surfactant, a Triton-X surfactant, and a Sorbitan surfactant; an anionic or a zwitterionic surfactant; and a hydrophilic solvent; wherein the medium has a total concentration of the surfactants from about 0.01%-10% (w/v).

These and other features of the invention will become apparent to those persons skilled in the art upon reading the details of the system, method and device for tissue-based diagnosis as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 (Panels a-g) is a collection of cross-sectional drawings illustrating structure, components and functioning of various abrasive energy-based tissue liquefaction devices. Panels a-c and Panels e-g show the sequential working of two separate liquefaction devices. Panel d is a schematic representation of a pressure-sensitive motorized shaft bearing an abrasive head.

FIG. 2 (Panels a-b) is a collection of cross-sectional drawings of moveable tissue liquefaction devices for continuous sampling of a large area of tissues.

FIG. 4 (Panel a-g) is a collection of cross-sectional drawings illustrating several types of abrasive heads.

DETAILED DESCRIPTION OF THE INVENTION

Definitions

Figure 3A:
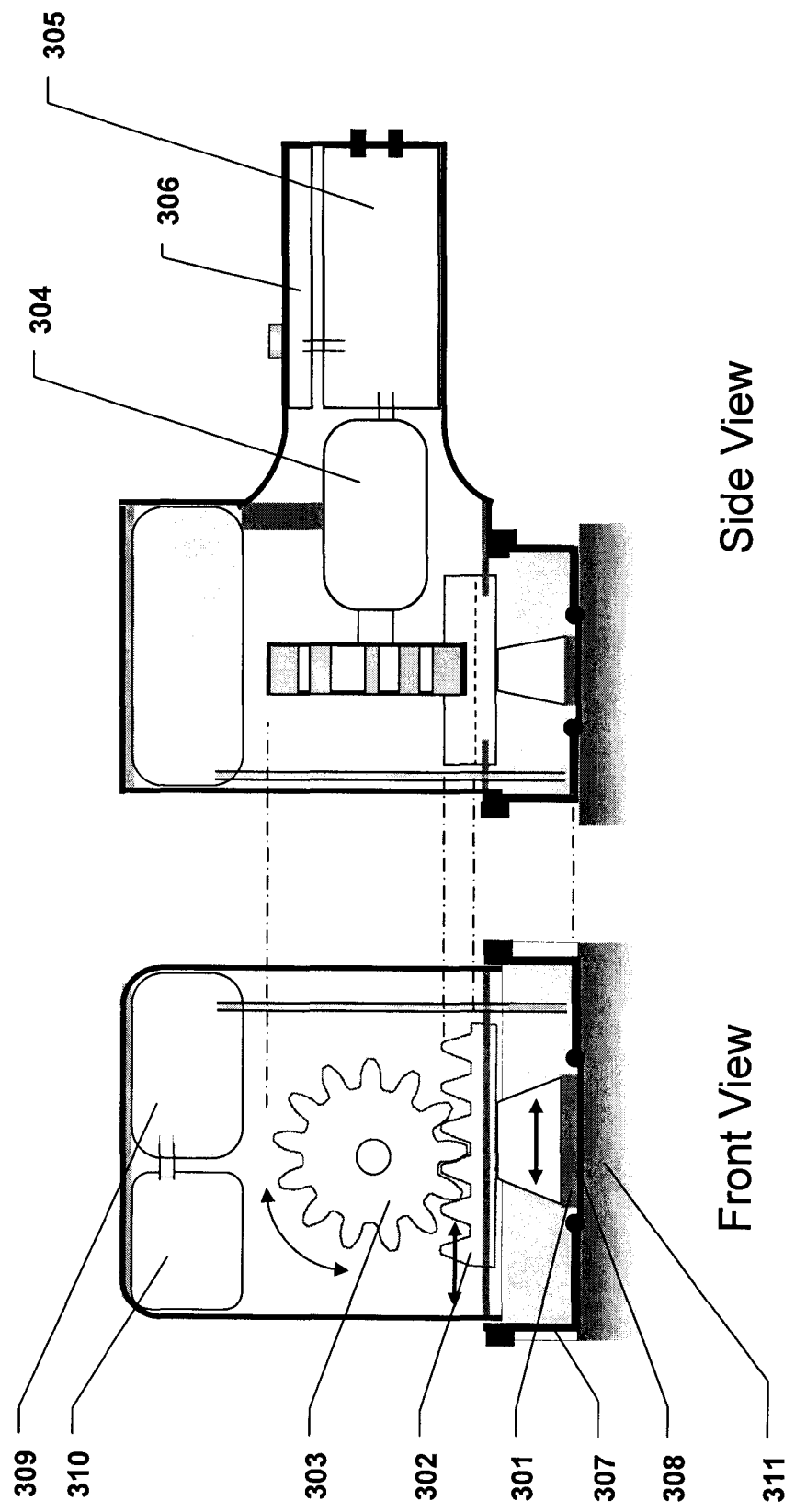
FIG. 3 (Panels a-c) is a collection of cross-sectional drawings illustrating structure and components of various linear abrasive motion-based tissue liquefaction devices. Panel c is a schematic representation of a pressure-sensitive support shaft bearing a gear.

"Energy" as used herein means any appropriate energy that can be applied to tissue to accomplish the objective of the methods disclosed herein (e.g., liquefying tissue). Exemplary types of energy include mechanical energy (e.g., abrasion, shear, vacuum, pressure, suction), ultrasound, optical (e.g., laser), magnetic, thermal, and electrical energy.

An "analyte" as used herein means any biomolecule (e.g., polypeptide, nucleic acid, lipid, and the like), drug (e.g., therapeutic drugs, drugs-of-abuse, and the like), small molecule (e.g., natural moisturizing factors, nicotine, and the like, with the understanding that small molecules can also be drugs), warfare agent, environmental contaminant (e.g., pesticides, etc.), microbe (e.g., bacterium, virus, fungus, yeast, and the like) and the like that is present in or on the tissue and can be extracted from the tissue of interest (e.g., skin, a mucosal membrane, and the like) and detected, analyzed, and/or quantified.

The term "liquefaction" is used to describe the process by which tissue and/or tissue constituents are converted to a sufficiently soluble state through exposure to sufficient energy and, optionally, a liquefaction promoting medium, and can involve conversion of at least a portion of a tissue structure of interest to a liquid form. A tissue sample that has been subjected to liquefaction as sometimes referred to herein as a "liquefied" sample.

The term "liquefaction-promoting medium" (LPM) is used to describe a substance that facilitates solubilization of one or more tissue constituents, facilitates conversion of at least a portion of a tissue structure into a liquid when exposed to energy, and/or facilitates preservation of bioactivity of one or more solubilized tissue constituents.

The term "liquefaction-promoting agent" (LPA) is used to describe a component of the liquefaction promoting medium, particularly an agent that promotes at least solubilization and/or preservation of bioactivity of one or more tissue constituents, and/or analysis of subsequent diagnostic assays.

A "calibration analyte" as used herein means any molecule naturally present in a tissue of interest at a known concentration, which can serve as a reference analyte (e.g., as a positive control to ensure a desired degree of liquefaction was achieved).

A "biomolecule" as used herein means any molecule or ion which has a biological origin or function. Non-limiting examples of biomolecules include proteins (e.g., disease biomarkers such as cancer biomarkers, antibodies: IgE, IgG, IgA, IgD, or IgM, and the like), peptides, lipids (e.g., cholesterol, ceramides, or fatty acids), nucleic acids (RNA and DNA), small molecules (e.g., glucose, urea, creatine), small molecule drugs or metabolites thereof, microbes, inorganic molecules, elements, or ions (e.g., iron, Ca2+, K+, Na+, and the like). In some embodiments, the biomolecule is other than glucose and/or is other than a cancer marker.

The term "abused drug" or "drug-of-abuse" or "illicit drug" are used interchangeably herein to refer to any substance which is regulated by a governmental (e.g. federally or state regulated) of which presence in a human tissue, and/or presence above a certain level in a human tissue, is illegal or can be harmful to a human being. Examples of abused drugs include: cocaine, heroin, methyl amphetamine, and prescription drugs taken in excess of dosage, or taken without a prescription (e.g., painkillers such as opioids).

The term "warfare agent" as used herein refers to any molecule, compound, or composition of either biological or chemical origin that may be used as a weapon. Examples of warfare agents include nerve gases (e.g. VX, Sarin), phosgene, toxins, spores (e.g., anthrax), and the like.

The term "environmental contaminant" as used herein includes any molecule, compound, or composition which can be detrimental to an individual, e.g., when at concentrations elevated above a risk threshold. Examples include water pollutants (e.g., fertilizers, pesticides, fungicides, insecticides, herbicides, heavy metals, halides), soil pollutants (e.g., fertilizers, pesticides, fungicides, insecticides, herbicides, heavy metals, halides), air pollutants (e.g., NOx, SOx, greenhouse gases, persistent organic pollutants (POPs), particulate matter, smog).

The term "decontamination" as used herein includes removal from tissues of any unwanted or undesired molecule, compound, or composition which can be detrimental to an individual. Examples include environmental contaminants (as defined above), toxic chemicals, and biological toxins.

The term "natural moisturizing factor" (NMFs) as used herein means any one of several types of small molecules, including but not limited to free amino acids, lactate, and urea, which are derivatives of fillagrin. NMFs can be used as analytes to facilitate assessment of general skin health (e.g., dry skin, flaky skin, normal skin, etc.). The term "mechanical index" as used herein means the ratio of the amplitude of peak negative pressure in an ultrasonic field and the square-root of the ultrasound frequency (Mechanical Index=(Pressure (MPa))/(Frequency (MHz))^0.5.

The term "drug delivery" as used herein means the delivery of one or more drugs into blood, lymph, interstitial fluid, a cell or tissue.

The term "sensitivity enhancer" as used herein means a substance or a mixture of substances that is mixed with LPM to stabilize liquefied tissue analytes and facilitate their analysis in terms of enhancing the sensitivity and specificity of the diagnostic analytical tests.

The term "blocking reagent" is used to describe a component which is used to prevent non specific binding of analytes to substrates used in a diagnostic assay.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a tissue" includes a plurality of such tissues and reference to "the liquid" includes reference to one or more liquids, and so forth. It is further noted that the claims may be drafted to exclude any optional element. As such, this statement is intended to serve as antecedent basis for use of such exclusive terminology as "solely," "only," and the like, in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The current invention provides systems, methods and devices, as well as compositions useful in such systems, methods and devices, involving application of energy to a tissue of interest to generate a liquefied sample comprising tissue constituents so as to provide for rapid tissue sampling, as well as qualitative and/or quantitative detection of analytes that may be part of tissue constituents (e.g., several types of biomolecules, drugs, and microbes—might want a paragraph to formally defined what you mean by tissue constituents). Determination of tissue composition or constituents can be used in a variety of applications, including diagnosis or prognosis of local as well as systemic diseases, evaluating bioavailability of therapeutics in different tissues following drug administration, forensic detection of drugs-of-abuse, evaluating changes in the tissue microenvironment following exposure to a harmful agent, decontamination, and various other applications.

Another object of the current invention is to provide a method and device for liquefying a tissue of a subject for facilitating the passage of a drug across or into the tissue. The method and device disclosed above are applicable not only to collection of tissue constituents but also to drug delivery. The device and method involve applying energy and a liquefaction medium to a tissue of interest of a subject, and delivering a drug through or into the site of the tissue to be liquefied. The advantage of using the present invention is 1) to provide higher fluxes of drugs into a tissue, and 2) to allow greater control of fluxes into a tissue. Drugs which would simply not pass through the tissues such as the skin and into the circulatory system are forced through the tissues when the method is applied.

Although the present invention may be described in conjunction with human applications, veterinary applications are within the contemplation and the scope of the present invention.

Tissue Diagnostics
Energy Application Devices

The tissue liquefaction devices disclosed herein can be generally described as having an energy source/generator operably coupled to a reservoir unit/housing, where the reservoir houses a medium in which analytes are collected and which, in most embodiments, facilitates transfer of energy to the tissue of interest and can thus, where desired, facilitate liquefaction of a tissue sample. In use, the reservoir housing is placed in contact with the subject's tissue to make contact between the medium and the tissue, and the energy source is activated. The device can be operably coupled to additional energy sources, (e.g., abrasive actuator, piezoelectric transducer, suction or pressure), which can also be applied to the tissue to facilitate transfer of energy to the tissue. As energy is applied to the tissue, constituents of the tissue are solubilized by the energy and collected in the medium. The medium can be retained in the reservoir housing, or alternatively be transferred to a separate container. The reservoir housing or container can be operably coupled to a detection device that can quantitatively measure the tissue constituents present in the medium.

Energy can be applied to the tissue from a single energy source or as a combination of sources. Exemplary energy sources include mechanical (e.g., abrasion, shear, vacuum, pressure, and the like), piezoelectric transducer, ultrasound, optical (e.g., laser), thermal, and electrical energy. The intensity of the energy applied, as well as the duration of the energy application, may be appropriately adjusted for the particular tissue of interest and the particular application of the method. The energy intensity and duration of application may also be appropriately adjusted based on the particular liquefaction promoting medium (LPM) used in connection with the energy. In some embodiments, an energy exposure time of greater than 1 minute, greater than 90 seconds, or greater than 2 minutes is provided in order to produce a suitable liquefied tissue sample. The magnitude of energy depends on the analyte of interest and the selection of LPM. Higher energies are required to liquefy tissues in the absence of surfactants or particles in the LPM. Use of high energies is limited by their adverse effects on the tissue or its constituents. A significant adverse effect is injurious tissue damage. In some embodiments, therefore, it might be necessary to incorporate certain device components that provide temporal monitoring (ideally, in real-time) of the change in tissue properties or the extent of tissue liquefaction such that, once safe limit for energy exposure is reached, the device can be stopped. The temporal evaluation can be performed prior, during, and after liquefaction process. In certain embodiments, the temporal evaluation is performed by electrochemical (e.g., tissue's electrical conductivity, measurement of certain ions by ion-selective electrodes, etc), biochemical (e.g., measurement of certain tissue components in the LPM by enzymatic assays such as ELISA and the like), or optical (e.g., measurement of LPM turbidity by spectrophotometer, etc) means. In an exemplary embodiment, tissue's temporal electrical conductivity is measured by applying a pre-defined AC electrical voltage across the tissue with a signal generator, and analyzing the resultant electrical current by a multimeter. Another significant adverse effect of high energy exposure is attributed to temperature elevation in the tissue, also known as thermal effects. In some embodiments, therefore, it might be necessary to incorporate a temperature sensing element (e.g., a thermocouple) that allows monitoring of the temperature of the tissue and/or the LPM, facilitating the judgment of a safe amount of energy exposure to the tissue.

The necessary energy level is significantly reduced by appropriate selection of LPM. For example, use of saline alone along with ultrasound resulted in recovery of less than 0.1 mg protein per $cm^2$ of skin. On the other hand, incorporation of surfactants such as DPS, NLS and Brij-30 at a concentration of 1% w/v in LPM increased protein recovery to more than 0.6 mg per $cm^2$ of skin.

In certain embodiments, use of energy to liquefy tissue may lead to reduction in biological activity of solubilized tissue constituents, necessitating selection of LPM which adequately preserve the bioactivity of tissue's molecules as well as aid tissue solubilization. For example, incorporation of one or more surfactants such as DPS, NLS and Brij-30 at a concentration of 1% w/v in LPM facilitated complete preservation of the bioactivity of solubilized proteins and nucleic acids under ultrasonic energy exposure.

In certain embodiments, energy can be applied to a tissue using an energy delivery chamber that includes an energy producing element. The chamber, when placed on the tissue, will expose the tissue to the energy producing element and allow energy to be applied to the tissue with minimal interference. Such a chamber can contain LPM and provide for contact of the LPM with the tissue such that, upon application of energy, tissue constituents can be directly collected into the solution.

In certain embodiments, the energy delivery chamber containing the LPM may also comprise a diagnostic device, for example, an analyte sensor, for detecting and, optionally, quantifying analytes that may be present in the LPM. These diagnostic devices can serve as chemical sensors, biosensors, or can provide other measurements to form a complete sampling and measurement system. An element having an internal channel for fluid transfer can be fabricated together with a sensor to form a disposable unit. The device can also be adapted to include or be provided as a disposable unit that provides for collection of analytes in the LPM for analysis.

Alternatively, the diagnostic element can be located elsewhere (e.g., separate from the energy device) and the contents of the energy delivery chamber in contact with tissue can be pumped using mechanical forces, capillary forces, ultrasound, vacuum, or electroosmotic forces into a sensing chamber and analyzed.

In certain embodiments, e.g., when evaluating topical formulations or determining pharmacological parameters, the unit can be constructed to function as a closed loop drug delivery unit, including drug delivery means, analyte recovery means, sensing means to measure the analyte, and control means to provide a signal to the drug delivery means.

An example of the general operation of an energy-assisted analyte device is described here. A portable disposable unit is inserted into a portable or bench-top energy generator. The energy generator may also include circuitry for tissue resistance measurements, analyte concentration measurements, and display of analyte concentration measurements. The system (e.g., energy applicator and disposable unit) is placed against the tissue, and energy is applied for a certain period of time, either alone or as a combination with other physical, mechanical, electrical, and chemical forces. The tissue of interest is liquefied, and analytes from the liquefied tissue are collected in the disposable unit and are measured using appropriate assays.

The preferred embodiment of the present invention and its advantages are best understood by referring to FIGS. 1 through 19 of the drawings, like numerals being used for like and corresponding parts of the various drawings.

Referring to FIGS. 1a through 1g, the structure, components and functioning of abrasive energy-based tissue liquefaction devices are shown. Panels through c of FIG. 1 show the sequential working of a device that utilizes a rotary abrasive component 101 as means for applying energy to tissues for liquefaction. Liquefaction is achieved by placing and setting abrasive component 101 in motion against a tissue of interest 107. Abrasive component 101 is attached to a shaft 102, which is further connected to a rotary motor 103 in the device. In some embodiments, shaft 102 is designed to sense and control the pressure applied by abrasive component 101 on tissue 107. In an exemplary embodiment, shaft 102 is constructed of shaft 1021 and shaft 1022 which are connected to each other by a pressure-sensitive spring 1023 (FIG. 1d). In another embodiment, shaft 1021 and shaft 1022 sandwich between them a pressure-sensing piezoelectric crystal for monitoring and controlling applied pressure to tissue 107. A battery pack 104 powers motor 103, which can subsequently set abrasive component 101 in rotary motion when directed by the device operator. Prior to liquefaction, abrasive component 101 is designed to be held in isolation against tissue 107 using a housing 105, and specifically, a thin sheet 106 located on the base of housing 105 (FIG. 1a). Upon initiation of the liquefaction process, LPM stored in a cartridge 108 is transferred to the housing 105 (FIG. 1a), whereupon the LPM contacts the surface of the sheet material 106, followed by setting the abrasive component 101 in motion against sheet 106. Material of sheet 106 is chosen such that it can be quickly abraded by abrasive component 101, allowing LPM and abrasive component 101 to come in contact with tissue 107 leading to tissue liquefaction (FIG. 1b). Non-limiting examples of sheet 106 include sheet of paper, rubber sheet, metal foil, plastic sheet, or any water-soluble sheet. Upon completion of liquefaction process, motor 103 stops and LPM containing tissue constituents is transferred to a sample container 110 (FIG. 1c) [not liquefied sample not clearly shown in 110 so would need a revised figure]; or directly into a pre-vacuumized container (thus avoiding the need for suction pump 109 and container 110). Where there is no pre-vacuumized container, collection of the sample is facilitated by a suction pump 109.

In some embodiments, certain device components are designed as disposable units such that, after each use of the device, these components can be replaced to allow sterile usage. Such components may include housing 105, abrasive component 101, cartridge 108, sample container 110, and other fluid-handling device components, as deemed necessary to maintain device sterility. Alternatively, in some embodiments, the whole device may be made disposable.

In certain embodiments, LPM storing cartridge 108 can be replaced with a sponge-bellow assembly for storage and release of LPM. Panels e through g of FIG. 1 show the sequential working of such a device. A flexible bellow-shaped housing 112 contains a sponge 111 filled with LPM (FIG. 1e). As the device is pushed against tissue 107, sponge-bellow housing is squeezed to release LPM and abrasive component 101 is set in motion (FIG. 1f). Upon completion of liquefaction process, motor 103 stops and LPM containing tissue constituents is transferred to a sample container 110 (FIG. 1g). Collection of the sample is facilitated by a suction pump 109. Alternatively, in some embodiments the suction pump 109 and container 110 may be avoided by collecting the sample into the sponge by lifting the device back into its original position.

Referring to FIGS. 2a and 2b, the structure and components of moveable tissue liquefaction devices designed for continuous sampling of a large area of tissue are shown. Panel a of FIG. 2 show a device that utilizes a rotary abrasive component 201 as means for applying energy to tissues for liquefaction. Liquefaction is achieved by placing and setting abrasive component 201 in motion against a tissue of interest 207. Abrasive component 201 is attached to a shaft 202, which is further connected to a rotary motor 203 in the device. In some embodiments, shaft 202 is designed to sense and control the pressure applied by abrasive component 201 on tissue 207. In an exemplary embodiment, shaft 202 is constructed of two distinct shafts which are connected to each other by a pressure-sensitive spring or a pressure-sensing piezoelectric crystal for monitoring and controlling the applied pressure to tissue 207. A battery pack 204 powers motor 203, which can subsequently set abrasive component 201 in rotary motion when directed by the device operator. Once the device is placed against tissue 207, a continuous liquefaction procedure is initiated by performing three key processes—LPM stored in a cartridge 208 is continuously delivered to housing 212 at the device-tissue interface; abrasive component 201 is set in motion against tissue 207; and liquefied tissue sample is continuously collected in a sample container 210 using a suction pump 209. The device can be moved around such that additional tissue surfaces are exposed to the device and liquefied. When desired, the liquefaction process can be stopped by switching-off motor 103 and cumulative tissue sample can be accessed from container 210.

In some embodiments, additional device components may be used for preventing LPM leakage from housing 212 due to the motion of device over tissue surface. In an exemplary embodiment, suction pump 209 can be used to create a vacuum-assisted seal between tissue 207 and chamber 206 located in a flanged housing 205 around the device.

Panel b of FIG. 2 show a device that utilizes a piezoelectric element 251 as means for applying mechanical energy to tissues for liquefaction. Piezoelectric element 251 is placed in a housing 252 that interfaces with a tissue of interest 259, and liquefaction is achieved by activating piezoelectric element 251 with LPM present as a coupling fluid between tissue 259 and piezoelectric element 251. Piezoelectric element 251 is a transducer of electrical energy, which is supplied to it by means of circuitry placed in a flexible tubing 253. During liquefaction, LPM is supplied to housing 252 by a flexible tubing 254 using an operator-controlled injection system 256. Liquefied tissue sample can be simultaneously collected from housing 252 into a sample container 257 using a flexible tubing 255. Sample collection is facilitated by a suction pump 258 which is serially connected to sample container 257. In some embodiments, suction pressure created in housing 252 by suction pump 258 may provide for an effective seal between housing 252 and tissue 259 for preventing LPM leakage from housing 252 during liquefaction. In some embodiments, suction pressure created in housing 252 by suction pump 258 may provide for an additional source of energy for liquefaction.

In some embodiments, housing 252 may be moved to liquefy additional tissue surfaces and collect a sample representing tissue constituents accumulated from various tissue surfaces. In such a device LPM is continuously supplied to housing 252 by tubing 254 and sample is continuously collected by tubing 255.

In certain embodiments, the device in FIG. 2b may operate without a piezoelectric element 251. In this embodiment, the LPM which flows from a tubing 254 into the housing 252 makes contact with the tissue and liquefies the tissue. Liquefied tissue is collected from the housing by tubing 255. The housing may be moved continuously or intermittently to collect samples from a large tissue area. The device may have additional means that are practically necessary to allow the movement of the device on a tissue, liquefaction of tissue and collection of liquefied tissue. In certain embodiments, either pressure or vacuum but not both may be used to direct LPM towards the tissue and collect liquefied tissue.

In certain embodiments, liquefaction devices may be integrated with a diagnostic probe such as endoscope, colonoscope, laparoscope, and the like.

Figure 3C:
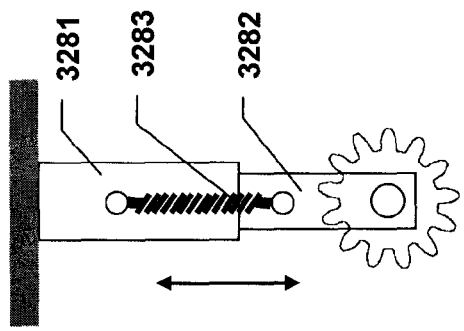
Figure 3B:
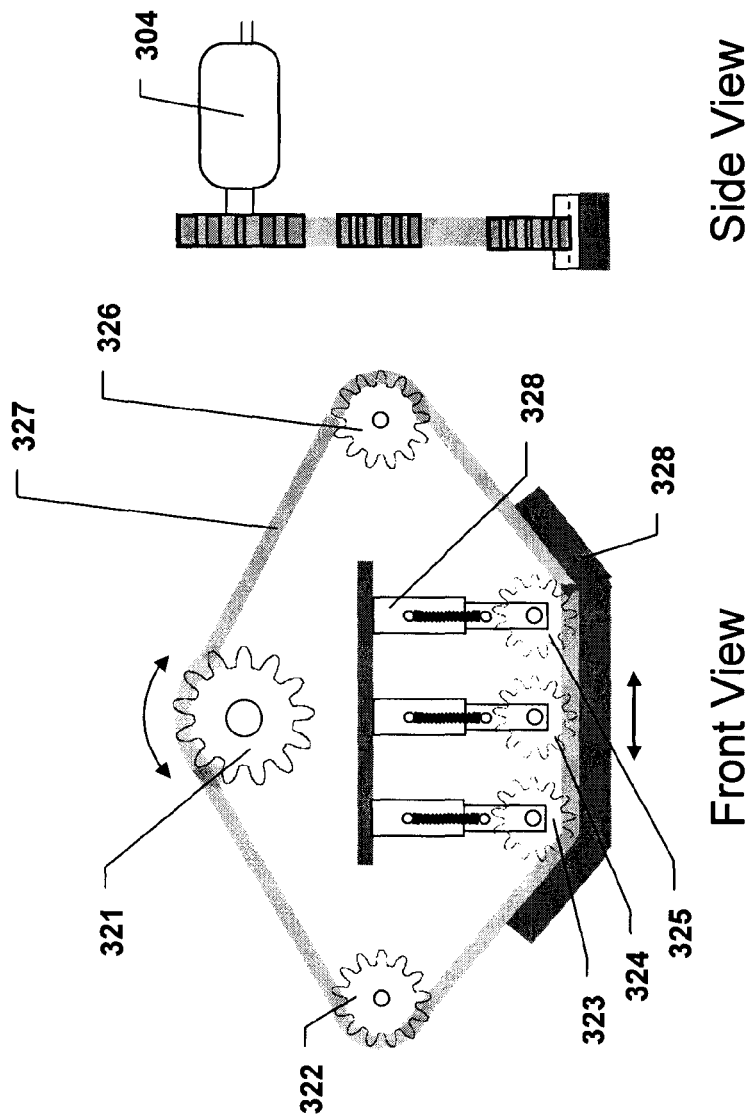

Referring to FIGS. 3a through 3c, the structure and components of liquefaction devices that utilize an oscillating abrasive component as means for applying energy to tissues for liquefaction are shown. Referring to FIGS. 3a, liquefaction is achieved by placing and setting abrasive component 301 in motion against a tissue of interest 311. Linear motion can be achieved, for example, by a rack and pinion arrangement (FIG. 3a). Specifically, abrasive component 301 is attached to a rack 302, which slides in a linear oscillatory motion using a circular gear 303 (pinion). Gear 303 is driven in oscillatory circular motion by a motor 304. A battery pack 305 powers motor 304. In some embodiments, motor 304 is a servo motor which may require an electronic microchip controller 306 to produce oscillatory circular motion. Prior to liquefaction, abrasive component 301 is designed to be held in isolation against tissue 311 using a housing 307, and specifically, a thin sheet 308 located on the base of housing 307. LPM can be pre-stored in housing 307, for instance, so that it is in contact with 308. In some embodiments, LPM may be transferred to housing 307 from a cartridge located elsewhere in the device. Liquefaction process is initiated by setting the abrasive component 301 in linear motion against sheet 308. Material of sheet 308 is chosen such that it can be quickly abraded by abrasive component 301, allowing LPM and abrasive component 301 to come in contact with tissue 311 leading to tissue liquefaction. Non-limiting examples of sheet 311 include sheet of paper, rubber sheet, metal foil, plastic sheet, or any water-soluble sheet. Upon completion of liquefaction process, motor 304 stops and LPM containing tissue constituents is transferred to a sample container 309. Collection of the sample is facilitated by a suction pump 310. In certain embodiments, the sample may be directly collected in a pre-vacuumized container, avoiding the need of suction pump 310 and container 310.

In some embodiments, certain device components are designed as disposable units such that, after each use of the device, these components can be replaced to allow sterile usage. Such components may include housing 307, abrasive component 301, sample container 309, and other fluid-handling device components, as deemed necessary to maintain device sterility. Alternatively, in some embodiments, the whole device may be made disposable.

In some embodiments, the linear oscillatory motion of abrasive component 301 may be generated by other mechanism such as using linear motors, linear motion actuators, ball screw assembly, leadscrew assembly, jackscrew assembly, and other devices for translating rotational motion to linear motion.

In some embodiments, a single rack and pinion system as described in FIG. 3a may be replaced with an arrangement of multiple gears and a belt as exemplified in FIG. 3b. Specifically, a belt 327 (not clear where belt is on figure—need revised figure) is mounted on gears 321, 322, 323, 324, 325 and 326. An abrasive component 328 is attached to belt 327 and is set in a linear oscillatory motion when gear 321 is driven by motor 304 in an oscillatory rotation motion. While gears 321, 322 and 326 are fixed to the housing of device, gears 323, 324 and 325 are mounted on shaft 328. Shaft 328 is fixed to the housing of device. In some embodiments, shaft 328 has a flexible length such that, as abrasive component 328 is pressed against a non-flat tissue surface, shafts 328 attached with gears 323, 324 and 325 are able to adjust their lengths in order to make abrasive component 328 contour with the non-flat tissue surface. Additionally, shaft 328 may be designed to sense and control the pressure applied by abrasive component 328 on tissue surface. In an exemplary embodiment, shaft 328 is constructed of shaft 3281 and shaft 3282 which are connected to each other by a pressure-sensitive spring 3283 (FIG. 3c).

Referring to FIGS. 4a through 4g, several designs of abrasive component used in devices, methods and systems disclosed in this invention are described. FIG. 4a illustrates an abrasive component comprising of a sheet of abrasive material with uniform thickness. Non-limiting examples of abrasive material with uniform thickness include fabric, abrasive crystals (e.g., quartz, metal, silica, silicon carbide, dust and derivatives of aluminum (such as $AlO_2$), diamond dust, polymeric and natural sponge, and the like, etc. In some embodiments, it may be advantageous to design an abrasive component with heterogeneous abrasiveness, for example, those having spatial variation of abrasiveness. In an exemplary embodiment, abrasive component is a disc with a gradient of abrasiveness that varies from high abrasiveness at disc's center to low abrasiveness at the disc periphery (FIG. 4b). In some embodiments, the shape of abrasive component may be varied to a non-planar geometry. In exemplary embodiments, FIG. 4c shows an abrasive component with a smooth and rounded tissue-facing surface (aspect ratio—defined as the ratio of height and width—may vary from 10 to 0.1), and FIG.

4d shows a circular ring-shaped abrasive component. FIGS. 4e through 4g show embodiments of abrasive components using brush as means for tissue abrasion. FIG. 4e illustrates an abrasive component comprising of a brush with bristles of uniform height and abrasiveness. In some embodiments, abrasive component comprises of a brush with bristles of different height and/or abrasiveness. FIG. 4f shows an exemplary embodiment of a circular disc-shaped brush with bristles of high abrasiveness at the center surrounded by bristles with low abrasiveness in the disc periphery. FIG. 4g shows an exemplary embodiment of a brush with bristles of different lengths forming a smooth and rounded tissue-facing surface (aspect ratio—defined as the ratio of height and width of abrasive component—may vary from 10 to 0.1).

Figure 5A:
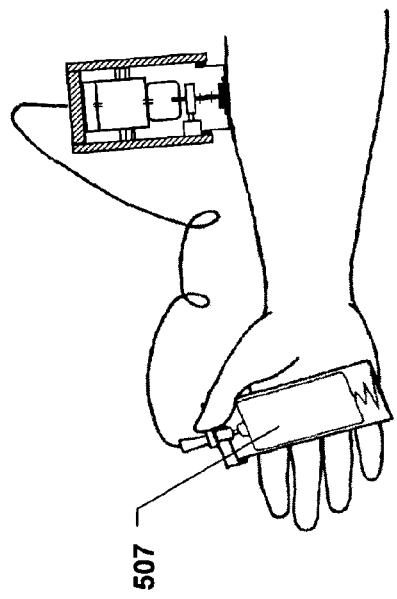
FIG. 5 (Panels a-d) is a collection of cross-sectional device drawings and schematics for measuring tissue's electrical conductivity.
Figure 5B:
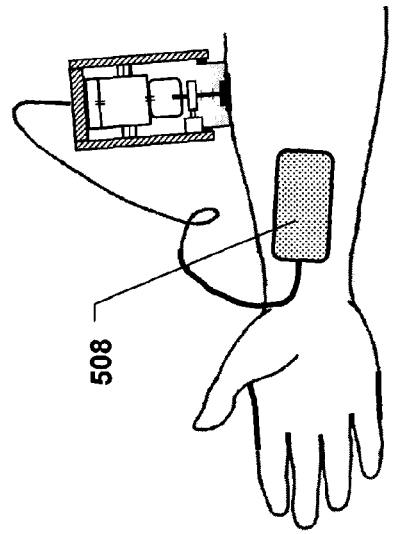
Figure 5C:
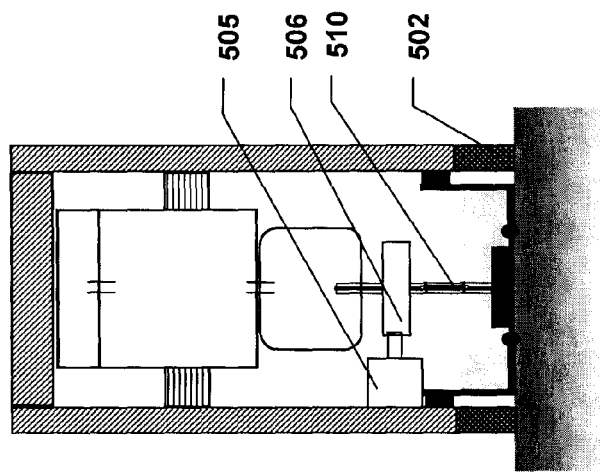
Figure 5D:
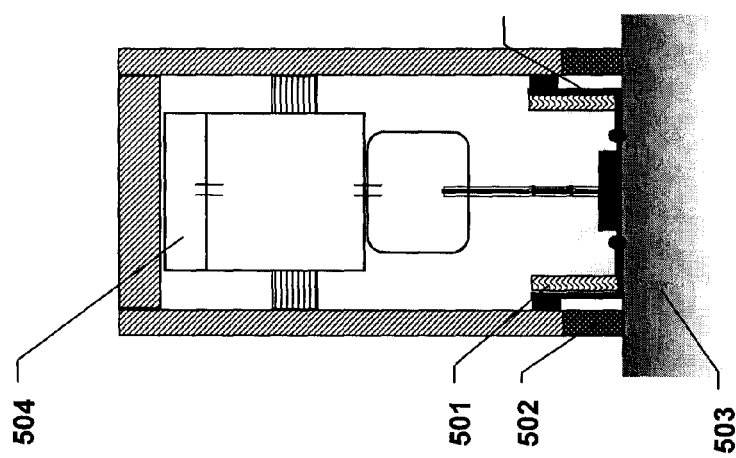

Referring to FIGS. 5a through 5d, device components for measuring a tissue's electrical conductivity are disclosed. While high energy exposure favorably liquefies tissues, its use may lead to significant adverse effects such as injurious tissue damage. In some embodiments, therefore, it might be necessary to incorporate certain device components that provide temporal monitoring (ideally, in real-time) of the change in tissue properties, e.g., tissue's electrical conductivity, such that, once safe limit for energy exposure is reached, the device can be stopped. Temporal measurement and monitoring of tissue's electrical conductivity during liquefaction process can be done by applying a pre-defined AC electrical voltage across the tissue of interest 503 using a measurement electrode 501 placed on tissue 503 and a reference electrode 502 placed in the vicinity of the region on tissue 503 that is being liquefied. The resultant electrical current across the two electrodes, as measured by an ammeter 504, can be taken as a measure of tissue's electrical conductivity. In some embodiments, measurement electrode 501 is maintained in electrical contact with LPM, or directly with the region on tissue 503 that is being liquefied. In an embodiment, measurement electrode 501 is located as an inner surface lining of LPM housing 509 (FIG. 5a). In certain embodiments, measurement electrode is a sliding contact 506 that is fastened to a motorized shaft 510 immersed in LPM (FIG. 5b). Electrical current is transmitted by sliding contact 506 to an isolated stud 505 secured on the device housing. In some embodiments, reference electrode 502 is an extension of LPM housing 509 and is placed in peripheral vicinity of the region on tissue 503 that is being liquefied (FIG. 5a and FIG. 5b). In some embodiments, reference electrode is a handheld cylindrical electrode 507 that is electrically connected with the electrical conductivity measurement components located in the liquefaction device (FIG. 5c). In some embodiments, reference electrode is a patch electrode 508 that is electrically connected with the electrical conductivity measurement components located in the liquefaction device (FIG. 5d).

Figure 6F:
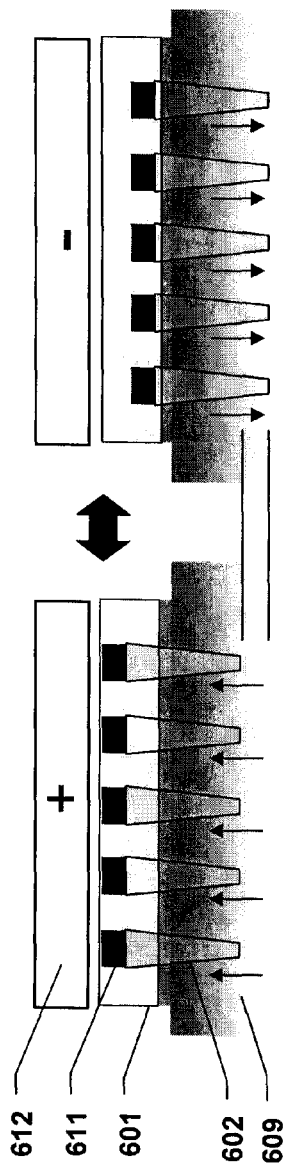
FIG. 6 (Panels a-g) is a collection of cross-sectional drawings illustrating structure, components and functioning of various microneedle-based tissue liquefaction devices.

Referring to FIGS. 6a through 6g, structure, components and functioning of devices utilizing microneedle-based tissue liquefaction are disclosed. Microneedle-based devices apply energy to tissues through mechanical disruption of tissue components which is primarily accomplished by pushing microneedles into the tissue. FIG. 6a shows the basic design of a microneedle patch 601 bearing a multitude of microneedles 602 which are pre-filled with LPM 613. Microneedle patch 601 can be inserted in the tissue of interest allowing disruption and dissolution of tissue components in LPM 613. LPM 613 can be later aspirated from patch 601 for diagnostic analysis.

Additional energy for liquefaction may be applied by post-insertion motion of microneedles inside the tissue. FIG. 6b illustrates a vibratory component 603 which may be secured on microneedle patch 601, which after insertion of patch 601 into tissue can be activated to vigorously shake microneedles 602 inside the tissue. Vibratory component 603 contains a multitude of mechanical vibrators 6031 and a battery-operated electronic circuit board 6032 for powering and controlling the motion of mechanical vibrators in desired directions. In an exemplary embodiment, mechanical vibrators 6031 can be vibrated in directions parallel and perpendicular to the axis of microneedles 602.

Figure 6G:
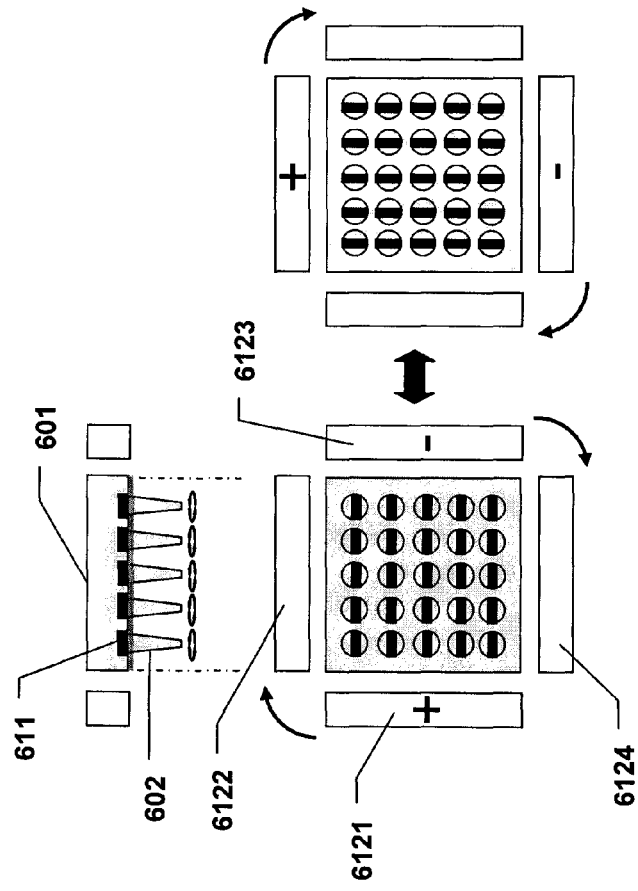

In some embodiments, motion of microneedles post-insertion may be produced by the motion of each microneedle 602 with respect to patch 601. FIG. 6f discloses an electromagnet 612 placed on top of patch 601. Electromagnet 612 may be used to produce oscillatory motion of each microneedle 602 along its axis. This can be achieved by fastening a magnet 611 on top of each microneedle 602, such that magnet 611 responds to an alternating polarity profile of electromagnet 612 leading to oscillatory linear motion of microneedles 602. In certain embodiments rotary motion of microneedles may be desired. Electromagnets 6121, 6122, 6123 and 6124 are placed symmetrically around patch 601 (FIG. 6g). Magnet 611 attached on top of each microneedle 602 responds to alternating polarity profile of electromagnet 6121, 6122, 6123 and 6124 leading to rotary motion of microneedles 602.

In FIG. 6b-6e, additional energy for liquefaction may be further applied by forced motion of LPM in tissue using active injection and withdrawal of LPM through microneedles. A housing 604 placed in the device may contain a compressed air container 605 which can be utilized to force LPM contained in patch 601 to flow inside tissue. A suction pump 606 in housing 604 may be used to apply vacuum for withdrawing LPM from tissue. In some embodiments, compressed air container 605 and suction pump 606 may be alternatively used for repeated injection and withdrawal of LPM from tissue for enhanced liquefaction. A battery-operated electronic circuit board 607 in housing 604 is used for powering and controlling compressed air container 605 and suction pump 606. In some embodiments, suction pump 606 may be additionally connected to a sample container to aspirate and transfer liquefied tissue sample from patch 601 to the sample container. In certain embodiments, housing 604 may be replaced by a flexible elastic cap 608 (see FIG. 6d) fitted on top of patch 601. Flexible cap 608 may be repeatedly pushed in and pushed out, for example, by pushing with a finger, such that LPM is repeatedly injected and withdrawn from the tissue through microneedles 602.

Microneedles 602 may be coated with a substance 610 to enhance tissue liquefaction (FIG. 6e). In some embodiments, substance 610 is an abrasive material which may help in enhanced disruption of tissue constituents and their faster dissolution in LPM. In some embodiments, substance 610 is an enzyme which may cleave specific tissue components such as extracellular matrix for enhanced tissue liquefaction. In some embodiments, substance 610 is a molecule that specifically binds to tissue analytes of interest leading to enhanced recovery of the analyte from the tissue. In an exemplary embodiment, substance 610 is an antibody.

Referring to FIG. 6, in some embodiments, certain device components may be designed as disposable such that, after each use of the device, these components can be replaced to allow sterile usage. Such components may include microneedle patch 601, microneedles 602, compressed air container 605, suction pump 606 and other fluid-handling device components, as deemed necessary to maintain device sterility. Alternatively, in some embodiments, the whole device may be made disposable.

Liquefaction-Promoting Medium (LPM)

The LPM can be designed to serve one or more of the following four purposes: a) it facilitates dispersion of tissues into its constituents, b) it acts as a medium to collect liquefied tissue constituents, and c) it inhibits degradation of the sampled constituents such that their chemical or biological activity is retained (e.g., by preserving various molecules' structural conformation and by preserving the ability of sampled microbes to multiply), and d) ensure compatibility to the subsequent analytical techniques.

In general, LPM comprises a solvent, such as aqueous solutions (e.g., Tris-HCl, phosphate buffered saline, etc) or organic ("non-aqueous") liquids (e.g., DMSO, ethanol, and the like), which may additionally contain a variety of liquefaction-promoting agents, including but not limited to surfactants (non-ionic, anionic, or cationic), fatty acids, azone-like molecules, chelating agents (e.g., EDTA, etc), inorganic compounds, and abrasive substances. "Liquefaction-promoting agent" as used herein refers to a component of a LPM which can facilitate liquefaction of a tissue sample and/or solubilization of tissue constituents. Depending on the tissue type and the analytes of interest, constituents of the LPM can be rationally selected based on the criteria described above. For example, a delicate tissue, such as mucosal membrane, can be liquefied by a saline solution with minimal or no surfactants, whereas keratinized tissues, such as skin, will require additional constituents, such as surfactants.

The liquefaction promoting agents within the LPM can comprise a variety of suitable components including, but not limited to: water, tris-HCl saline (phosphate-buffered saline (PBS), and tris-buffered saline (TBS)), alcohols (including ethanol and isopropanol (e.g., in a concentration range of 10-100% in aqueous solution)), abrasive substances, such as dust or derivatives of silica, aluminum oxide, or silicon carbide (e.g., in a concentration range of 0.01-99% (w/v) in water-based solution), surfactants, such as Brij (various chain lengths, e.g., Brij-30), 3-(Decyl dimethyl ammonio) propane sulfonate (DPS), 3-(Dodecyl dimethyl ammonio) propane sulfonate (DDPS),N-lauroyl sarcosine (NLS), Triton X-100, Sodium Dodecyl Sulfate (SDS) and Sodium Lauryl Sulfate (SLS), HCO-60 surfactant, Hydroxypolyethoxydodecane, Lauroyl sarcosine, Nonoxynol, Octoxynol, Phenylsulfonate, Pluronic, Polyoleates, Sodium laurate, Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Tweens, Sodium alkyl sulfates, and alkyl ammonium halides, (e.g., in concentrations ranging between 0.01-20% in water-based solution), DMSO (e.g., in a concentration range of between 0.01-20% in water-based solution), fatty acids such as linoleic acid (e.g., in a concentration range of between 0.1-2% in ethanol:water (50:50), azone (e.g., in a concentration range of 0.1-10% in ethanol:water (50:50), polyethylene glycol (e.g., in a concentration range of 10-50% in water-based solution), histamine (e.g., in a concentration range of 10-100 mg/ml in water-based solution), EDTA (e.g., in a concentration range of 1-100 mM), and sodium hydroxide (e.g., in a concentration range of 1-100 mM). In some embodiments the LPM may contain surfactants other than TWEEN, CTAB, SPAN, or Sodium Alkyl Sulfate. In some embodiments, the LPM may contain surfactants other than cationic surfactants. Where the LPM includes a surfactant, the total concentration of the surfactant (w/v) in the LPM can range from at least 0.5%, to 10%, and can be, for example, about 0.5%, about 1%, about 1.5%, about 2%, about 2.5%, or about 3%.

The LPM can include agents that facilitate preservation of bioactivity of an analyte of interest. For example, the LPM can contain free radical scavengers (e.g., antioxidants (e.g., polyphenol, beta-carotene, lutein, lycopene, selenium, etc), vitamin A, vitamin C, vitamin E, alpha-tocopherol, butylated hydroxytoluene, sodium benzoate, sodium formate, and the like); defoaming agents (e.g., silicone or non-silicone anti-foaming agents such as dimethylpolysiloxane, hydrocarbon oil, low fatty acid diglyceride, and the like); and shear protectants (e.g., polyethylene glycol, polyvinyl alcohol, pluronic F68, and the like). "Bioactivity" as used in the context of an analyte refers to a structural conformation that facilitates detection (e.g., such as an epitope bound by a specific antibody or other structural feature that is sensitive to denaturation), and may also include a biological activity of an analyte (e.g., enzymatic activity).

LPM of particular interest are those that contain a combination of surfactants that when used in connection with the devices, methods and systems disclosed herein provides for a desired level of tissue constituents in the LPM while providing for preservation of bioactivity of analytes in the LPM, particularly so as to provide for maintenance of structural conformation of an analyte (e.g., avoid denaturation of a protein analyte).

Use of different combinations of surfactants including combination of nonionic surfactant, zwitterionic surfactant and anionic surfactant in the LPM may provide for both high levels of tissue constituents in the LPM and good preservation of bioactivity of an analyte contained in the LPM following use in devices, methods and systems described herein.

Non-limiting examples of non-ionic surfactants of interest include Brij series surfactants (e.g., Polyethylene glycol dodecyl ether (Brij 30), Polyoxyethylene 23-lauryl ether (Brij 35), Polyoxyethylene 2-cetyl ether (Brij 52), Polyoxyethylene 10-cetyl ether (Brij 56), Polyoxyethylene 20-cetyl ether (Brij 58), Polyoxyethylene 2-stearyl ether (Brij 72), Polyoxyethylene 10-stearyl ether (Brij 76), Polyoxyethylene 20-stearyl ether (Brij 78), Polyoxyethylene 2-oleyl ether (Brij 92), Polyoxyethylene 10-oleyl ether (Brij 96), Polyoxyethylene 100-stearyl ether (Brij 700), Polyoxyethylene 21-stearyl ether (Brij 721), and the like); Triton X (e.g., Triton X-15, Triton X-45, Triton X-100, Triton X-114, Triton X-165, Triton X-200, Triton X-207, Triton X-305, Triton X-405, and the like); and Sorbitan (e.g., Span-20, Span-40, Span-60, Span-65, Span-80, Span-85, and the like).

Non-limiting examples of zwitterionic surfactants of interest include 3-(Decyl dimethyl ammonio) propane sulfonate, 3-(Dodecyl dimethyl ammonio) propane sulfonate, Myristyldimethyl ammonio propane sulfonate, Hexadecyldimethyl ammonio propane sulfonate, ChemBetaine C, ChemBetaine Oleyl, ChemBetaine CAS, and 3-(3-cholamidopropyl)-dimethylammonio-1-propanesulfonate.

Non-limiting examples of anionic surfactants of interest include N-lauroyl sarcosine, Sodium Cocoyl Sarcosinate, Sodium Myristoyl Sarcosinate, Isopropyl Lauroylsarcosinate, Sodium Palmitoyl Sarcosinate, and Disodium Lauroamphodiacetate Lauroyl Sarcosinate.

In some embodiments, non-ionic surfactants are combined with zwitterionic surfactants. In certain embodiments, non-ionic surfactants are combined with anionic surfactants. In these embodiments, the ratio of non-ionic surfactant to zwitterionic, or anionic surfactant present in the LPM can be adjusted to achieve desired results. Non-limiting ratios of interest include 25:75 non-ionic:zwitterionic surfactant, 50:50 non-ionic: zwitterionic surfactant, 75:25 non-ionic: zwitterionic surfactant, 25:75 non-ionic:anionic surfactant, 50:50 non-ionic:anionic surfactant, and 75:25 non-ionic:anionic surfactant. A mixture of particular interest is a 50:50 surfactant mixture of a Brij series surfactant (e.g., Brij-30)

and N-lauroyl sarcosine (NLS). Another mixture of particular interest is a 50:50 surfactant mixture of a Brij series surfactant (e.g., Brij-30) and 3-(Decyl dimethyl ammonio) propane sulfonate (DPS). As illustrated in the Examples below, these combinations of surfactants, when included in the LPM at a total surfactant concentration of 0.5-1% (w/v), provided for solubilization of a high level of tissue constituents as assessed by total protein concentration, and provided for retention of bioactivity (as assessed by ELISA technique).

In some specific cases, for example, the collection of live pathogens, different LPM compositions can be used to achieve desired results. Saline and tris-Hcl were used as an LPM to provide for collection of a wide variety of skin-resident bacteria, and additionally, these microbes remained potent to multiply and grow ex vivo. In some embodiments, an LPM may contain an enrichment broth medium to supports growth of sampled microbes. Some of anaerobic bacteria are sensitive to an oxygen atmosphere. Thus, the LPM for collecting anaerobic bacteria may contain a nitrogen and hydrogen atmosphere. It will be evident to the ordinarily skilled artisan upon reading the present disclosure that LPM compositions varying in components can be readily produced for use in specific applications.

LPM can also include stabilizers of analytes of interest, such as protease-inhibitors, RNase-inhibitors, and DNase-inhibitors, which can provide for collection and at least temporary storage of analytes with minimal or no detectable degradation or loss of bioactivity. Other exemplary liquefaction-promoting agents are described in U.S. Pat. No. 5,947,921, which is incorporated herein by reference in its entirety. For example, the liquefaction-promoting agent can include surfactants, abrasive particles, and biomolecule stabilizers.

In one exemplary embodiment, the LPM is composed of a solution of 1% w/v mixture of NLS and Brij-30 in sterile PBS. In another exemplary embodiment, the LPM is composed of a solution of 0.5% w/v mixture of DPS and Brij-30 in sterile PBS. In certain embodiments, specifically where the analytes are one or more proteins, the LPM contains a 1-10% v/v protease inhibitor cocktail (e.g., catalog number: P8340, provided by Sigma-Aldrich, St. Louis, Mo.). In certain embodiments, the LPM is a saline solution. In certain embodiments, the LPM is a tris-HCl solution.

LPM can also include agents defined as "sensitivity enhancers", which are used to stabilize liquefied tissue analytes and facilitate their analysis in terms of enhancing the sensitivity and specificity of the diagnostic analytical tests. As deemed necessary to achieve these goals, the sensitivity enhancers can be added into LPM prior, during or after tissue liquefaction process, or prior or during the diagnostic analysis. For example, the sensitivity enhancer may be pre-stored in a container, and later the liquefied tissue sample may be mixed.

In typical embodiments, sensitivity enhancers are formulated of substances that synergistically act with specific components of LPM (as disclosed above) to enhance the detection sensitivity and specificity of analytes of interest. In an exemplary embodiment, sensitivity enhancers are formulated of substances for preventing non-specific binding of protein analytes present in tissue sample to various diagnostic assay substrates, resulting in their sensitive and specific detection. In some embodiments, sensitivity enhancers are formulated to stabilize analytes of interest by deactivating molecules such as protease, RNase and DNase. In some specific cases, sensitivity enhancers may be formulated of substances that activate proteases to prevent non specific biding of certain analytes of interest with proteins present in the liquefied sample. In some embodiments, sensitivity enhancers are used to adjust the physiological state (for example, pH) of the liquefied samples to facilitate downstream analysis of analytes of interest.

In some embodiments, sensitivity enhancer may comprise of a solvent, such as aqueous solutions (e.g., phosphate buffered saline, tris-buffered saline, etc) or organic liquids ("non-aqueous") liquids (e.g., DMSO, ethanol, phenol and the like), which may additionally contain but not limited to blocking reagents (e.g., Tween 20, Triton X-100, bovine serum albumin, non-fat dry milk, casein, caseinate, fish gelatin, sonicated-sperm-nucleic acids and the like), stabilizers such as protease, protease-inhibitors, RNase-inhibitors and DNase-inhibitors, broth mediums. Depending on the type of tissue and analyte of interest, components of the sensitivity enhancer can be rationally chosen. In an exemplary embodiment, for detecting nucleic acids in liquefied keratinized tissue such as skin, the sensitivity enhancer comprises of 100 mM NaCl, 10 mM Tris Cl (pH 8), 25 mM EDTA (pH 8), 0.5% SDS, and 0.1 mg/ml protease K. Herein, Protease K may not only facilitates liquefaction of the skin but may also stabilize nucleic acids by decomposing DNase and RNase—present in the sample as a tissue analyte.

In some embodiments involving analyte detection by an immunoassay, sensitivity enhancer may comprise of a variety of suitable components including, but not limited to: solvent (e.g., water, a buffer solution (e.g., phosphate-buffered saline, tris-HCl, tris-buffered saline, etc), and the like), a stabilizer such as a protease inhibitor, and a blocking reagent such as Tween 20, Triton X-100, bovine serum albumin (e.g., in a concentration range of 1-5%), non-fat dry milk (e.g., in a concentration range of 0.1-0.5%), casein or caseinate (e.g., in a concentration range of 1-5%), fish gelatin (e.g., in a concentration range of 1-5%). In an exemplary embodiment, the sensitivity enhancer for immunoassays is composed of a solution of 10% BSA and 0.5% Tween 20 in Tris-buffered saline and is mixed with the tissue sample at ratio of 1:10.

In some embodiments involving detection of nucleic acids as an analyte of interest, sensitivity enhancer may comprise of various suitable components including, but not limited to: water, a buffer solution (e.g., TE, TAE, sodium citrate, etc), a chelating agents such as EDTA, a stabilizer (e.g., RNase-inhibitor, DNase-inhibitor, protease, phenol, ammonium sulfate, guanidine isothiocyanate, etc), a surfactant such as sodium dodecyl sulfate, and blocking reagents such as sonicated-sperm-nucleic acids, Tween 20, Triton X-100, bovine serum albumin (e.g., in a concentration range of 1-5%), non-fat dry milk (e.g., in a concentration range of 0.1-0.5%), casein or caseinate (e.g., in a concentration range of 1-5%), fish gelatin (e.g., in a concentration range of 1-5%). In some embodiments, where detection of nucleic acids is desired by using polymerase-chain-reaction (PCR) technology, the LPM has to be chosen so as to avoid inclusion of PCR-inhibitors as LPA. In exemplary embodiments, PCR-compatible LPM is Tris-Hcl buffer, or EDTA buffer.

In some embodiments involving detection microbes as an analyte of interest, sensitivity enhancer may comprise an enrichment broth medium so as to facilitate growth of microbes ex vivo. Some of anaerobic bacteria are sensitive to an oxygen atmosphere. Thus, the sensitivity enhancer for collecting anaerobic bacteria may contain a nitrogen and hydrogen atmosphere.

Other formulations of sensitivity enhancer for specific assay system or specific analyte of interest will be evident to the ordinarily skilled artisan upon reading the present disclosure.

In some embodiments, the thermal properties (e.g., temperature, heat-capacity, and the like) of the LPM can be manipulated before or during tissue liquefaction so as to reduce the adverse thermal effects of energy exposure on tissue and/or its constituents. In one embodiment, the temperature of the LPM is maintained low enough not to induce melting of the tissue constituents. In another exemplary embodiment, a pre-cooled LPM having temperature lower than the ambient temperature (about 25° C.) can be used for ultrasound liquefaction. In another exemplary embodiment, the temperature of the LPM can be continuously reduced during energy exposure by transferring its heat to a pre-cooled liquid flowing through a heat-transfer jacket coupled to the LPM-containing reservoir.

Analytes

A variety of analytes can be detected (qualitatively or quantitatively) with the devices, methods and systems disclosed herein and, optionally, characterized to provide an analyte profile of the tissue in question. Non-limiting examples include: structural and signaling proteins (e.g., keratins (e.g., basic keratins, acidic keratins), β-actin, interleukins, chemokines, growth factors, colony-stimulating factors, interferons, antibodies (IgE, IgG, IgA, IgD, IgM), cancer biomarkers (e.g., CEA, and the like), heat shock proteins (e.g., Hsp-60, Hsp-70, Hsp-90, etc.), and the like, lipids (e.g., cholesterol), ceramides (e.g., ceramides 1-6), fatty acids, triglycerides, paraffin hydrocarbons, squalene, cholesteryl esters, cholesteryl diesters, free fatty acids, lanosterol, cholesterol, polar lipids (e.g., glucosyl-derivatives and phospholipids), and the like, nucleic acids (e.g., RNA and DNA), small molecules (e.g., free amino acids, lactate, exogenously delivered drug molecules, environmental contaminants, warfare agents, and the like) and microorganisms (e.g. bacteria, fungi, viruses and the like). These analytes are found within the tissue itself, and may not be solely present in the interstitial fluid around the tissue. The analyte may be other than a marker associated with interstitial fluid, such as a tumor marker. Thus, the devices, methods and systems disclosed herein can be adapted to detect tumor markers that are present in tissue structures, but which may or may not also be present in interstitial fluid.

In a particular embodiment, antibodies against allergens and cytokines are liquefied (are these liquefied or is the tissue liquefied to produce these soluble analytes) and characterized to provide an allergy profile for the tissue and the subject in question. Specific types of antibodies include but are not limited to IgE and IgG antibodies. Specific types of cytokines include but are not limited to IL4, IL5, IL10, IL-12, IL13, IL-16, GM-CSF, RANTES, MCP-4, CTACK/CCL27, IFN-g, TNFa, CD23, CD-40, Eotaxin-2, and TARC.

The analytes can be analyzed in many ways, which can be readily selected by the ordinarily skilled artisan in accordance with the analyte to be evaluated. A reservoir or collecting container can be applied to the site for collection of sample, which is then measured using analytical techniques. Application of energy can be optimized to maximize analyte recovery. It may be desirable for certain applications to maintain the relative levels of the analyte to other components of the sample. Exemplary assay methods include but are not limited to gel electrophoresis, agar plating, enzymatic testing, antibody-based tests (e.g., western blot tests, Enzyme-Linked Immuno Sorbent Assay (ELISA), lateral flow assays, and the like), thin layer chromatography, HPLC, mass spectrometry, radiation-based tests, DNA/RNA electrophoresis, (UV/Vis) spectrophotometry, flow assays, and the like.

A quantitative measurement of the presence of tissue constituents in the liquefied tissue sample can assess the extent of tissue liquefaction. Such an internal calibration can be accomplished by measuring one or more optical properties of the liquefied tissue sample such as absorbance, transmittance, scattering, or fluorescence emission upon being irradiated by a source emitting electromagnetic waves. Additional sample parameters such as gravimetric-weight, total protein content, pH, and electrical conductance can be used for calibrating the extent of liquefaction. Further, measurement of tissue properties such as thickness, rate of water loss, and electrical conductivity can be used. Direct measurement of the concentration of one or more sampled analytes such as β-actin, β-tubulin, GAPDH (glyceraldehyde 3-phosphate dehydrogenase), LDH (lactate dehydrogenase), or any other abundantly-present biomolecule whose concentration is expected to remain constant in the tissue, can be used for calibrating the extent of tissue liquefaction. Analytes could also be quantified using immunological based assay (i.e. radioimmuno; Eliza; FACs).

Tissue Cells and Microorganisms

In addition to the analytes described above, whole cells of tissue under analysis, as well as a variety of microorganisms, can be detected in tissues of interest using the devices, methods and systems disclosed herein. Tissue cells and most microorganisms are much larger than the analytes described above, and their extraction from a tissue of interest can be accomplished using various embodiments of the current invention. Pathogenic and nonpathogenic bacteria, virus, protozoa, and fungi play well-known roles in various infectious diseases, and their detection can facilitate a diagnosis of a disease caused by the microorganism (e.g., tuberculosis, herpes, malaria, ringworm, etc.). The disease state exhibits either the presence of a novel microorganisms or an alteration in the proportion of resident microorganisms. When a subject is suspected of having an infection with such a microorganism, the devices, methods and systems disclosed herein can be used to quantify or detect the presence or absence of a microorganism, and facilitate diagnosis of the condition.

Non-pathogenic microorganisms are normally present in healthy tissues ("normal flora"), and can play a role in many bodily functions and maintenance of health of a subject. Detection of these normal flora microorganisms (e.g., bacteria) in a tissue of interest can also be accomplished with the current method and device. A subject's tissue can be sampled and analyzed using the devices, methods and systems disclosed herein to examine the various microorganisms that are naturally present. When a subject is suspected to have an abnormal condition, tissue of the subject can be sampled according to the devices, methods and systems disclosed herein to detect the presence or absence of a change in a profile of non-pathogenic microorganisms relative to that of a normal, healthy subject. A change in this microorganism profile can facilitate diagnosis of a condition of interest in the subject.

In some embodiments, tissues can be liquefied to recover their cells or microorganisms residing therein. Application of the present devices, methods and systems using energy provide for collection of bacteria from skin of a subject into a collection medium which may optionally contain an LPA. For example, application of ultrasound energy to the tissue of interest using tris-Hcl or PBS is sufficient to collect bacterial microflora. In general, use of a device utilizing this method involves application of a sufficient level of ultrasound energy so as to dislodge microorganisms from the tissue and enter the collection medium, which is then collected for subsequent analysis, which may include culturing the medium to determine whether certain microorganisms are present, directly assaying the medium (e.g., using ELISA techniques, e.g., involving microorganism-specific antibodies, e.g. involving a latex agglutination test, e.g., using a nucleic-acid-based diagnostic assay including the polymerase chain reaction hybridization, DNA sequencing method), or a combination of these approaches. Detection of microorganisms in the medium facilitates diagnosis of a condition of interest. Furthermore, a high yield collection of microorganisms could shorten or eliminate a process to amplify the number of nucleic acids for diagnostics.

The invention described herein can also be used to collect cells from the tissue. Application of energy with an appropriate LPM that liquefies tissues without disrupting cell membranes can be used to harvest whole cells, including viable whole cells from tissues. LPM in this case may comprise chemicals including but not limited to ion chelating agents such as EDTA or enzymes such as trypsin to dislodge the cells. Similarly, with changes in parameters of energy and/or LPM as discuss above, the devices, methods and systems of the present disclosure can be used to collect nuclei or other cellular organelles.

Tissue of Interest

A variety of tissues are well suited to the devices, methods and systems disclosed herein. These tissues include but are not limited to skin, mucosal membranes (nasal, gut, colon, buccal, vagina etc.) or mucus, breast, prostate, eye, intestine, bladder, stomach, esophagus, nail, testicles, hair, lung, brain, pancreas, liver, heart, bone, or aorta wall. In one embodiment, the tissue is skin, which can be skin of the face, arms, hands, legs, back, or any other location. While skin and mucosal surfaces are highly accessible for performing liquefaction, liquefaction devices, methods and systems described in this disclosure can be designed to readily adapt to various internal tissues listed above. Exemplary devices specific to internal tissues that can find use in the methods disclosed herein include those disclosed in U.S. Pat. No. 5,704,361, U.S. Pat. No. 5,713,363, and U.S. Pat. No. 5,895,397, each of which are incorporated herein by reference in their entirety.

In some embodiments, the tissue of interest is other than a tumor or a tissue suspected of being a tumor. Where the devices, methods and systems disclosed herein are applied to detection of a microorganism, the tissue of interest is one suspected of containing a microorganism (e.g., a tissue suspected of having an infection, particularly a deep tissue infection, e.g., infection of the dermal and/or subdermal layers of the skin, including such layers of mucosal membranes).

Method of Use

The methods disclosed herein can be used for a broad range of tissue evaluations, including assessment of the presence or absence of an analyte(s) of interest to facilitate diagnosis of a condition of interest. In some embodiments, the methods find use where, for example, the patient presents with clinical signs and symptoms suggestive of one or more conditions, where the methods disclosed herein can facilitate a differential diagnosis.

In certain embodiments, the current invention provides methods that involve comparing a test analyte profile generated from a patient sample to a reference analyte profile. A "reference analyte profile" or "analyte profile for a reference tissue" generally refers to qualitative or quantitative levels of a selected analyte or set of 1, 2, 3, 4, 5, 6, 7, 8, 9, 10 or more analytes, which are characteristic of a condition of interest. Exemplary conditions of interest for which a reference analyte profile may be provided include, but are not limited to, normal reference analyte profile (e.g., healthy tissue (i.e., absence of disease), general tissue health, acceptable or tolerated levels of an analyte (e.g., a drug, environmental contaminant, etc.), disease reference analyte profile (e.g., an analyte profile characteristic of the presence of, for example, microbial infection (e.g., bacterial, viral, fungal, or other microbial infection), localized diseases in tissues (e.g., dermatitis, psoriasis, cancers (prostate, breast, lung, etc.), urticaria, etc.), systemic diseases manifested in tissues (e.g., allergies, diabetes, Alzheimer's disease, cardio-vascular diseases, and the like); etc.), environmental contaminant reference analyte profile (e.g., an analyte profile characteristic of the presence of unacceptably high levels of an environmental contaminant (e.g., warfare agent, pollens, particulates, pesticides, etc.), drug reference analyte profile (e.g. an analyte profile characteristic of therapeutic levels of a drug, drug-of-abuse (e.g., to facilitate assessment of drug-of-abuse), etc.); and the like. Reference analyte profiles may include analytes that are members of one or more classes of analytes (e.g., proteins (e.g., antibodies, cancer biomarkers, cytokines, cytoskeletal/cytoplasmic/extra-cellular proteins, and the like), nucleic acids (DNA, RNA), lipids (which include ceramides, cholesterol, phospholipids, etc.), biologically-derived small molecules, drugs (e.g., therapeutic drugs, drugs-of-abuse), environmental contaminants, warfare agents, etc.) or members of a subclass of analytes (e.g., antibodies, phospholipids). Reference analyte profiles of a given condition of interest may be previously known in the art or may be derived from the tissue using the methods described in this invention. Reference analyte profiles can be stored in electronic form (e.g., in a database) to provide for ready comparison to a test analyte profile to facilitate analysis and diagnosis.

A "test analyte profile" or "analyte profile for a tissue of interest" refers to qualitative or quantitative levels of a selected analyte or set of 1, 2, 3, 4, 5, 6, 7, 8, 9, 10 or more analytes, to facilitate diagnosis or prognosis of a condition of interest. A test analyte profile may include analytes that are members of one or more classes of analytes (e.g., proteins, nucleic acids, lipids, biologically-derived small molecules, drugs (e.g., proteins (e.g., antibodies, cancer biomarkers, cytokines, cytoskeletal/cytoplasmic/extra-cellular proteins, and the like), nucleic acids (DNA, RNA), lipids (which include ceramides, cholesterol, phospholipids, etc.), biologically-derived small molecules, drugs (e.g., therapeutic drugs, drugs of abuse), environmental contaminants, warfare agents, etc.) or members of a subclass of analytes (e.g., antibodies, phospholipids). In general, the analytes selected for analysis to generate a test analyte profile are selected according to analytes of a desired reference analyte profile. Comparison of a test analyte profile to an appropriate reference analyte profile facilitates determining the presence or absence of the condition or state of interest, e.g., by assessing whether there is a substantial "match" between a test analyte profile and a reference analyte profile.

Methods for generating reference and test analyte profiles of a selected analyte or set of analytes can be accomplished using methods available in the art, and will be selected according to the analyte(s) to be assessed.

The current methods can be used for a broad range of tissue evaluations. Energy-assisted tissue liquefaction can provide a quantitative evaluation and profile of normal tissue. Comparison of the normal tissue profile with a profile of tissue under investigation can facilitate diagnosis of changes in tissue microenvironment (e.g. up/down-regulation of several proteins, lipids, nucleic acids, small molecules, drugs, etc) which can indicate various diseased conditions such as allergies, cardio-vascular disease, dermatitis, etc. The methods can also be used as a tool for monitoring tissue recovery and evaluating therapeutic efficacy of various treatments (as in monitoring of therapy, which can be combined with modification of therapy as desired or needed). The analyte profiling methods can also provide tools for the personal-care industry for evaluation of topical formulations (e.g., as in cosmetics). This methodology can be utilized for determining pharmacologic parameters by liquefying tissues and detecting the drug molecules therein. In a similar manner, rapid and routine testing of chemicals, bio-hazardous contaminants, and drugs-of-abuse can also be quantitatively accomplished. The methods can also be used for sensitive detection and diagnosis of pathogenic microflora.

In certain embodiments, the current methods provide a profile of normal tissue, wherein normal tissue is defined by the absence of the abnormal tissue condition of interest. Energy is applied to the normal tissue, e.g., by ultrasound exposure or abrasion, in the presence of a liquefaction-promoting agent. Various tests are performed upon the liquefied tissue sample to isolate and identify the analytes present in the tissue.

In certain embodiments, the methods can be applied to facilitate diagnosis of various tissue diseases which are characterized by a quantitative evaluation of a change in the tissue microenvironment. This evaluation is performed by comparing an analyte profile of a reference tissue (e.g., a reference analyte profile, which may be stored in a database) with the analyte profile of the tissue of interest (i.e., the test analyte profile). The quantitative presence or absence of a certain analyte or set of analytes present in a tissue under investigation, when compared to the quantitative presence or absence of the same analytes in a reference tissue will indicate the presence or absence of a particular disease, and thus facilitate diagnosis of the condition. The reference analyte profile can be one characteristic of tissue which is known to not be affected with the disease in question, or can be a reference analyte profile characteristic of the disease in question for the tissue in question.

In one embodiment, the tissue under investigation is skin and/or mucosal membranes, and the quantitative test analyte profile is compared to a reference analyte profile to determine the presence or absence of a disease such as allergy, urticaria, microbial infection, auto-immune disease, cardiovascular disease, or cancer.

In certain embodiments, this method can be used to monitor tissue recovery. This monitoring is performed by comparing an analyte profile of reference tissue with the analyte profile of tissue under investigation. The quantitative presence or absence of a certain analyte or composition of analytes present in a tissue under investigation, when compared to the quantitative presence or absence of the same analytes in a reference tissue can indicate whether or not the tissue is returning to its healthy state. The reference tissue is usually tissue that is in a healthy state.

In certain embodiments, the current methods can be used to evaluate the therapeutic effect of various treatments, including bioavailability of therapeutics in tissues of interest. The analyte in the liquefied tissue sample can be quantified to indicate how much of the analyte is present in the tissue. The quantitative presence or absence of a certain analyte or composition of analytes present in a tissue under investigation, when compared to the quantitative presence or absence of the same analytes in a reference tissue, can indicate whether or not the dosed therapeutic agent is staying in the specific tissue or body long enough to achieve its desired effect. The reference tissue is usually tissue that is in a healthy state.

In certain embodiments, the methods disclosed herein can be used to evaluate therapeutic formulations on a tissue such as skin, specifically, whether component(s) of a formulation (e.g., lotions, creams, salves, and the like) are being absorbed by the tissue, and if the amount delivered is therapeutically effective. In certain embodiments, the methods disclosed herein can include a closed loop system, in which the same system can apply the therapeutic formulation, liquefy the analytes, analyze the analyte profile, and adjust the delivery of the formulation accordingly. The reference tissue in this case would be healthy tissue, or tissue at various levels of recovery from the condition that the therapeutic formulation was treating.

In certain embodiments, the current methods can be used to determine the analyte profile for use in determining pharmacological parameters or efficacy of pharmaceutical agents. The presence or absence of certain analytes (e.g., immune system responders, cytokines) can be used to correlate certain dosages of pharmaceutical agents to biological parameters, including but not limited to bioavailability, AUC, clearance, and half life.

In certain embodiments, the methods disclosed herein can be used to detect the presence or absence of certain chemicals, including but not limited to bio-hazardous contaminants, warfare agents, illicit drugs, known pharmaceutical agents, and the like. Such methods find use in, for example, law enforcement, regulation of doping in competitive sports, evaluation of exposure and/or risk of disease as a result of exposure to toxins or contaminants, and the like.

In certain embodiments, the current methods can be used for detecting or diagnosing pathogenic microbes (e.g., bacteria, fungi, viruses, and the like). Current methodologies for microbial diagnostics in tissues, such as replica plating, swabbing, and washing, are unattractive due to large variability and low dispersion of extracts, which leads to decreased sensitivity and high protocol-dependency. Various tests can be performed upon the liquefied tissue sample to isolate and identify the microbial analytes present in the tissue. In certain embodiments, these tests include plating on agar plates.

Drug Delivery

The present invention provides a method and device involving liquefaction of a tissue so as to control and enhance the flux of drugs into or through the tissue. The method includes the steps of 1) applying energy and a liquefaction promoting medium to a tissue where transport is desired of a subject; and 2) delivering one or more drugs into or through the tissue to be liquefied continuously or repeatedly. The method may further include reliquefy the tissue over the period of time during which transport occurs. The method comprising liquefying a tissue can perturb the barrier properties of a tissue or biological surface, leading to reducing the resistance to the drug's passage. The advantage of the present invention is that the rate and efficiency of transfer is both improved and controlled. Drugs which would simply not pass through the biological surfaces, or pass at a rate which is inadequate or variable over time, are forced into the biological surfaces when energy in combination of a LPM is applied. By controlling the mode, intensity and time of energy application and formulation of a LPM, the rate of transfer is controlled.

The transport of drugs can be modulated or enhanced by the simultaneous or subsequent application of a secondary driving force such as chemical permeability or transport enhancers, convection, osmotic pressure gradient, concentration gradient, iontophoresis, electroporation, magnetic field, ultrasound, or mechanical pressure.

Enhancement of the disclosed method was demonstrated by the following non-limiting example employing $^3$H-labelled Acyclovir and Inulin. The required type, length of time, and intensity of energy and formulation of a LPM are dependent on a number of factors including the type of tissues and the property of drugs, which varies from species to species, with age, injury or disease, and by location on the body.

Drug to be Administered

Drugs to be administered include a variety of bioactive agents, but are preferably proteins or peptides. Specific examples include insulin, erythropoietin, and interferon. Other substances, including nucleic acid molecules such as antisense, siRNA and genes encoding therapeutic proteins, synthetic organic and inorganic molecules including anti-inflammatories, antivirals, antifungals, antibiotics, local anesthetics, and saccharides, can also be administered. The drug will typically be administered in an appropriate pharmaceutically acceptable carrier having an absorption coefficient similar to water, such as an aqueous gel. Alternatively, a patch can be used as a carrier. Drug can be administered in a gel, ointment, lotion, or suspension.

In one embodiment, the drug is in the form of or encapsulated in a delivery device such as liposome, lipid vesicle, emulsion or polymeric nanoparticles, microparticle, microcapsule, or microsphere (referred to collectively as microparticles unless otherwise stated). These can be formed of polymers such as polyhydroxy acids, polyorthoesters, polyanhydrides, and polyphosphazenes, or natural polymers such as collagen, polyamino acids, albumin and other proteins, alginate and other polysaccharides, and combinations thereof. The microparticles can be coated or formed of materials enhancing penetration, such as lipophilic materials or hydrophilic molecules, for example, polyalkylene oxide polymers, and conjugates, such as polyethylene glycol.

Administration of Drug

The drugs are preferably administered, using the liquefaction devices mentioned, to the tissues at a site selected based on convenience to the patient as well as to achieve desired treatment results. A variety of tissues including biological surfaces are well suited to the current method. These tissues include but are not limited to skin, mucosal membranes (nasal, gut, colon, buccal, intestine, vagina, etc.). In one embodiment, the method of the current invention is preferably administered to the skin of the face, arms, hands, legs, back, or any other location. While skin is highly accessible for performing liquefaction, the devices described in this disclosure can be designed to readily adapt to various internal membranes listed above.

In some embodiment, the tissue to be administered is a diseased tissue such as infectious organs, tissues that is inflamed, and solid tumors. In a certain embodiment, the present invention comprises using the liquefying devices on the healthy tissues in the vicinity of and/or the diseased tissue, and delivering drugs across the healthy tissues and/or into the site of the diseases. Steroids such as corticosteroids and many of chemotherapeutic agents including estramustine phosphate, paclitaxel, and vinblastine have potentially severe side effects. Hence, if given systemically, they are likely to cause undesirable side effects. This problem is overcome by delivering these drugs locally to the disease tissues. Other indications include delivery of drugs into abnormal skin such as psoriasis, atopic dermatitis, and scars.

In some embodiments, the current invention is used to enhance the passage of a compound such as a large molecular weight or polar molecule through the tissue such as skin, mucosal membranes (nasal, gut, colon, intestine, buccal, vagina etc.). Greater control and drug utilization are achieved by increasing the rate and directional control of the applied drug. The percentage of drug which quickly enters the bloodstream is increased accordingly and undesirable side effects are avoided. Drugs through the tissues stated above are infused into the bloodstream at an optimal rate.

Liquefaction Promoting Medium (LPM) for Drug Delivery

A LPM is also an important component for drug delivery. The design of the LPM for drug delivery is overlapping somewhat to that of the LPM for sample collection. The LPM can be designed to serve one or more of the following five purposes: a) it couples energy to a tissue, b) it facilitates liquefaction of the tissue, c) it storages drugs to be delivered into the tissue, d) it increases the solubility of the drugs, and e) it inhibits degradation of the drugs such that their biological or chemical activity is retained.

The LPM may also contain a drug prior or during tissue liquefaction process. In an alternate embodiment, application of energy and the LPM which excludes a drug can be used for liquefying a tissue, and subsequently a drug in an appropriate carrier such as a patch can be applied on a site of the tissue to be liquefied.

Kits

The present disclosure also encompasses kits for practicing the current methods. The subject kits can include, for example, the entire energy application device and a liquefaction-promoting agent to liquefy tissues of interest, reagents for conducting assays to detect and analyze (qualitatively or quantitatively) the presence or absence of tissue analytes in the liquefied tissue sample generated through methods disclosed herein. The various components of the kit may be present in separate containers, or certain compatible components may be pre-combined into a single container, as desired.

In addition to the above-mentioned components, the kits typically further include instructions for using the components of the kit to practice the methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step, or steps, to the objective, spirit and scope of the present invention. All such modifications are intended to be within the scope of the claims appended hereto.

Example 1

Sampling of Skin by an Abrasive Energy-Based Device

Figure 7A:
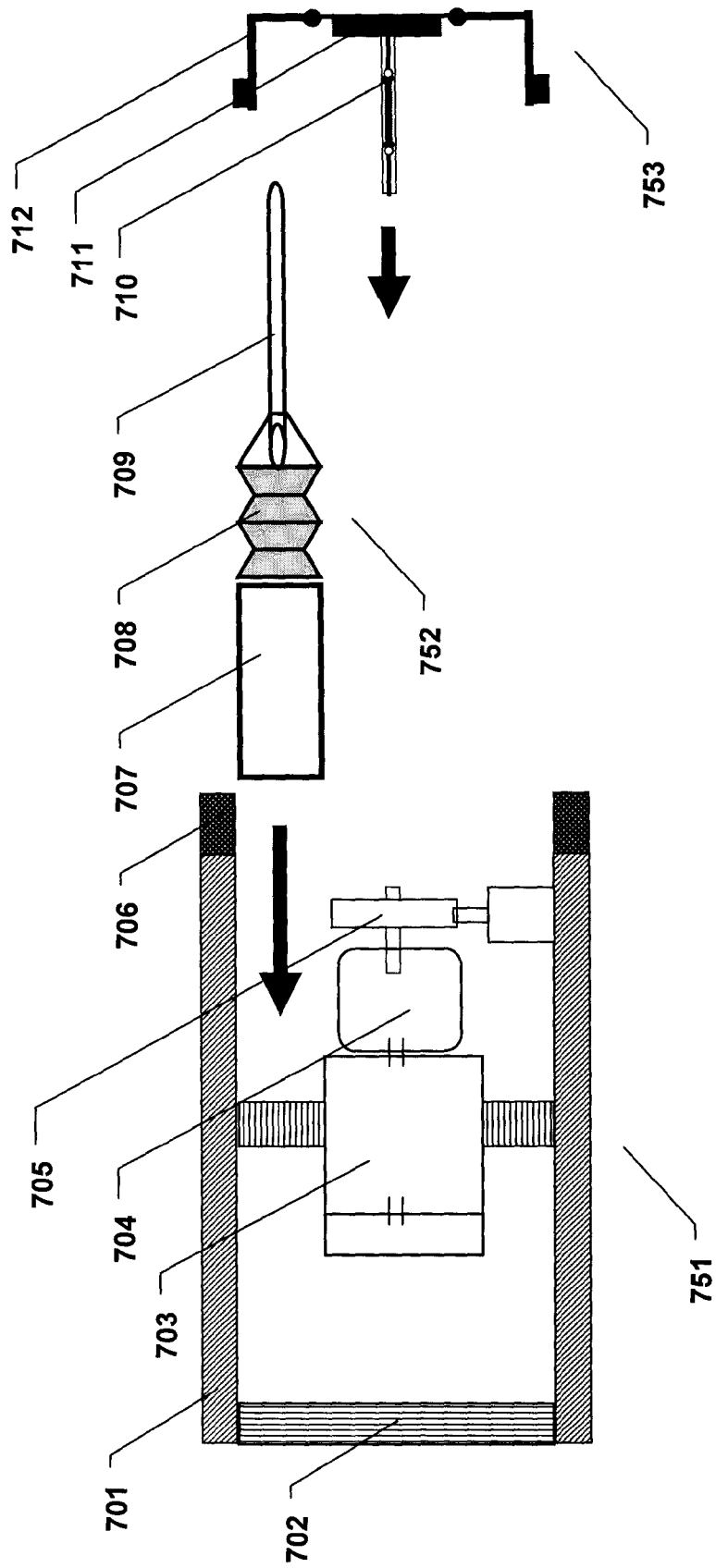
FIG. 7 (Panels a-e) is a collection of cross-sectional drawings of an exemplary abrasive energy-based tissue liquefaction device. Panel a shows various assembly components of the device. Panel b-d show sequential working steps of the device including transfer of the liquefaction medium to be placed in contact with the tissue (Pane b-c), sample generation by liquefaction (Panel c), and collection of the sample in a container (panel d). Panel e shows post-liquefaction retrieval of sampling container from the device.
Figure 7D:
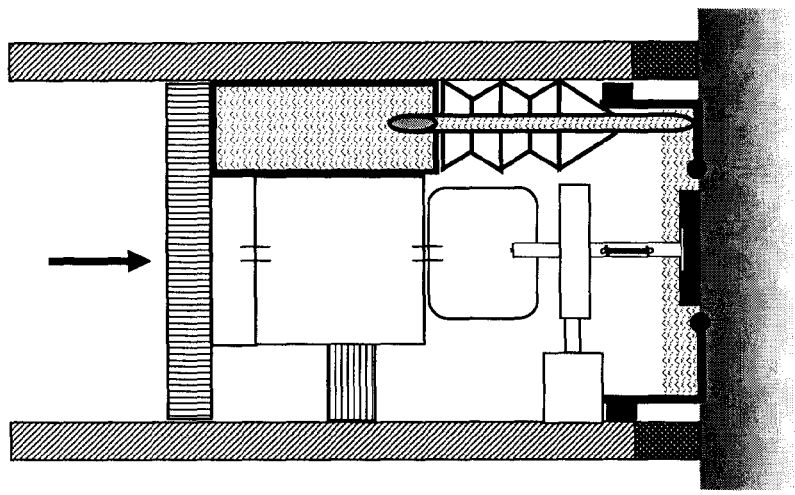
Figure 7C:
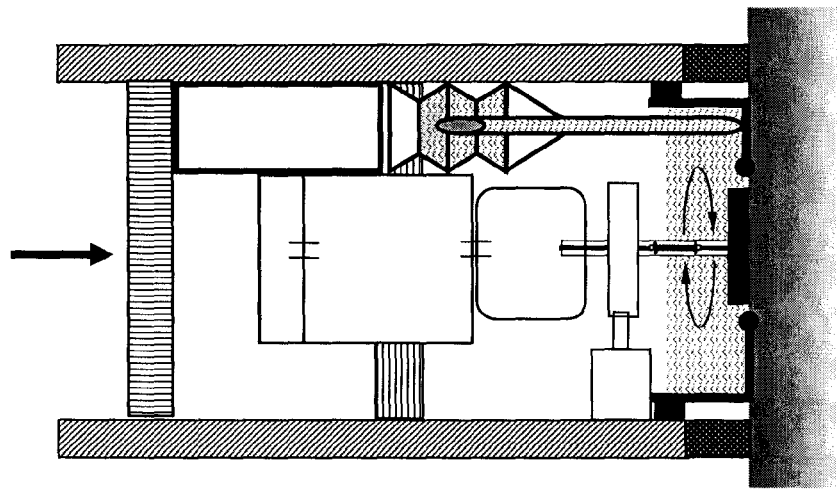
Figure 7B:
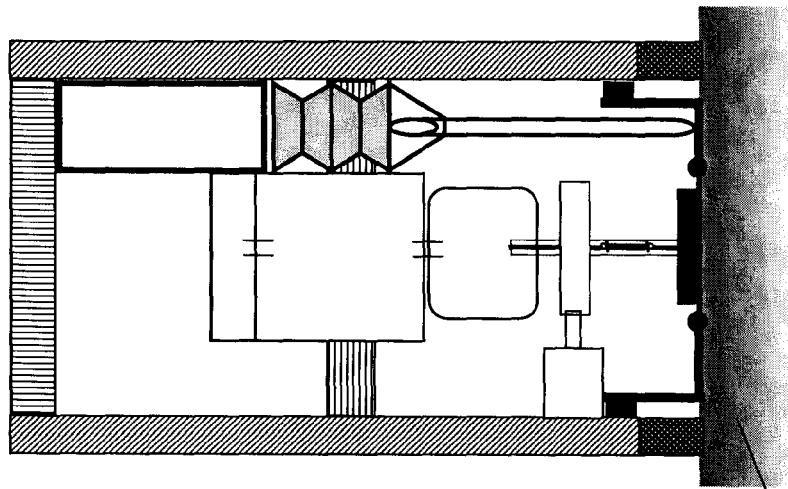
Figure 7E:
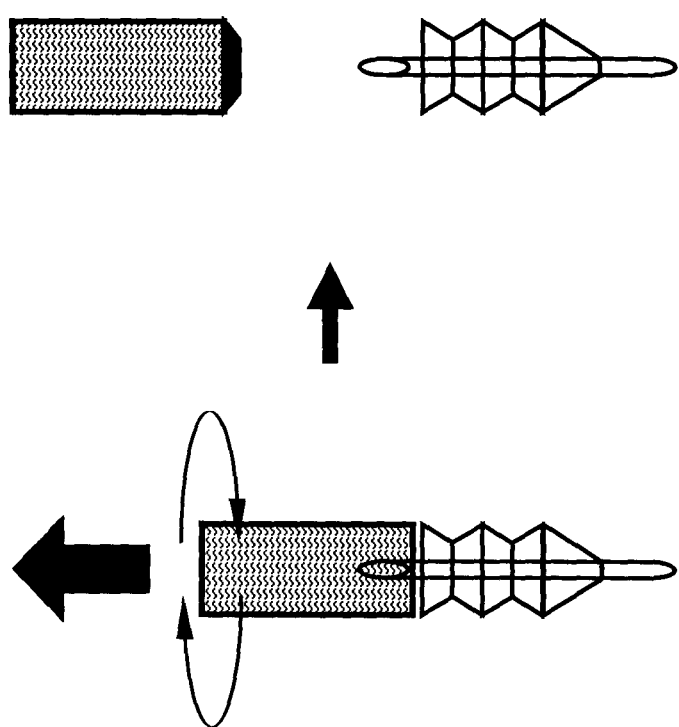

Referring to FIGS. 7a through 7e, an abrasive energy-based tissue liquefaction device for sampling of skin tissue is described. Device is assembled from three components—751 (assembly of device housing 701 containing motor 704 and electrical conductivity components 705 and 706); 752 (disposable assembly of LPM cartridge 708, collection container 707 and needle 709); and 753 (disposable assembly of LPM housing 712, abrasive pad 711 and shaft 710) (FIG. 7a). The assembled device is placed against a pre-identified region of interest on skin 713, such that abrasive pad 711 is facing skin 713 (FIG. 7b). Sliding plunger 702 located on top of the device is pushed towards skin, which pushes needle 709 into LPM cartridge 708, breaking its sterile seal and transfers LPM into housing 712. Sliding plunger 702 also energizes motor 704 through battery pack 703, setting the shaft 710 and abrasive pad 711 in rotary motion against skin tissue 713. As skin tissue is liquefied, tissue components are dissolved in LPM contained in housing 712. Electrical conductivity of skin tissue 713 is also simultaneously measured using sliding contact 705 fastened to shaft 710 as measurement electrode and reference electrode 706. Once the safe energy exposure limit is reached as determined by threshold electrical conductivity, motor 704 stops. Sliding plunger 702 is further pushed towards skin such that needle 709 punctures a pre-vacuumized sample container 707, which aspirates the sample from housing 712 in it (FIG. 7d). The device is removed form skin and disassembled. The device component 752 is further dissembled and sample container 707 is processed for detection of analytes.

Example 2

Sampling of Skin by a Microneedle-Based Device

Figure 8D:
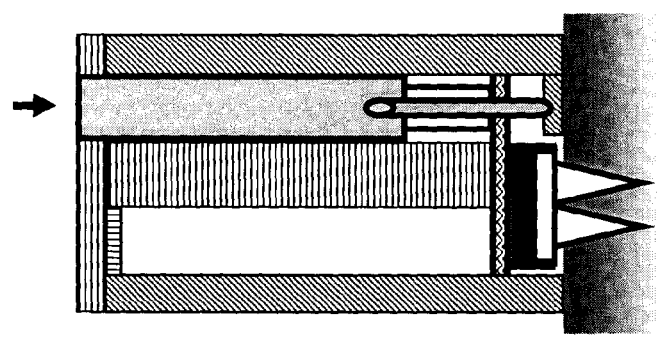
FIG. 8 (Panels a-d) is a collection of cross-sectional drawings illustrating sequential working steps of an exemplary microneedle-based tissue liquefaction device: transfer of the liquefaction medium to be placed in contact with the tissue (Pane a-b); sample generation by liquefaction (Panel c); and collection of the sample in a container (panel d).
Figure 8C:
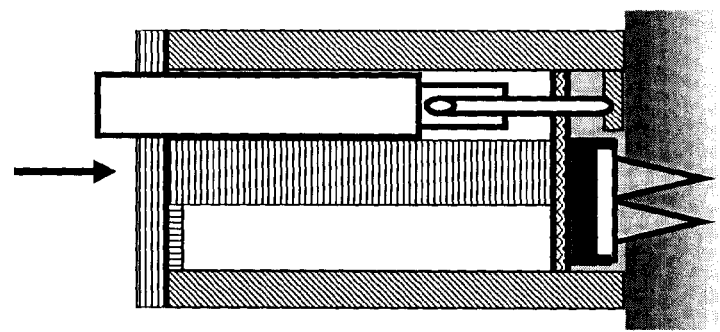
Figure 8B:
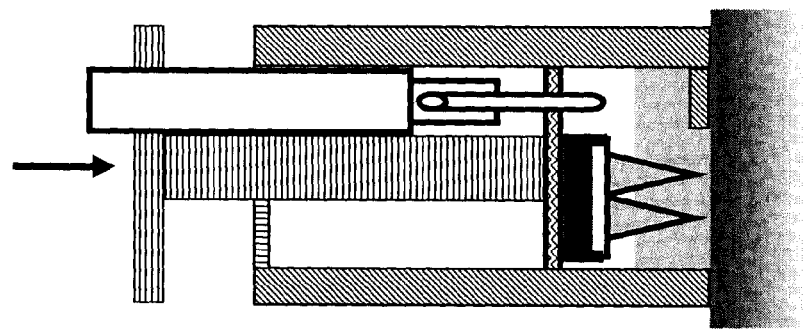
Figure 8A:
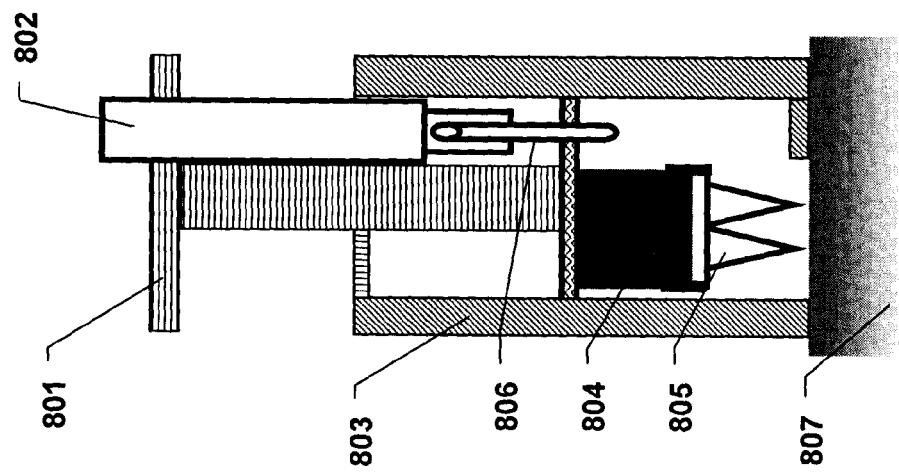

Referring to FIGS. 8a through 8d, a microneedle-based tissue liquefaction device for sampling of skin tissue is described. The device is placed against a pre-identified region of interest on skin 807, such that microneedle bearing patch 805 is facing skin 807 (FIG. 8a). Sliding plunger 801 located on top of the device is pushed towards skin 807 such that LPM soaked sponge 804 is squeezed and releases LPM into housing 803 (FIG. 8b). Consequently, microneedles in patch 805 and housing 803 at the skin interface are filled with LPM. To initiate liquefaction process, sliding plunger 801 is further pushed into skin tissue 807 leading to insertion of microneedles 805 into skin tissue 807 (FIG. 8c). As skin tissue is liquefied, tissue components are dissolved in LPM contained in housing 803. Upon completion of skin liquefaction, pre-vacuumized sample container 802 is pushed towards skin tissue 807 such that needle 806 punctures sample container 802 resulting in aspiration of sample from housing 803 in it (FIG. 8d). The device is removed from skin and disassembled. Sample container 802 is retrieved for analyte analysis and the rest of the device components are disposed off.

Example 3

Reservoir Housing for Capturing Tissue Analytes

Figure 9:
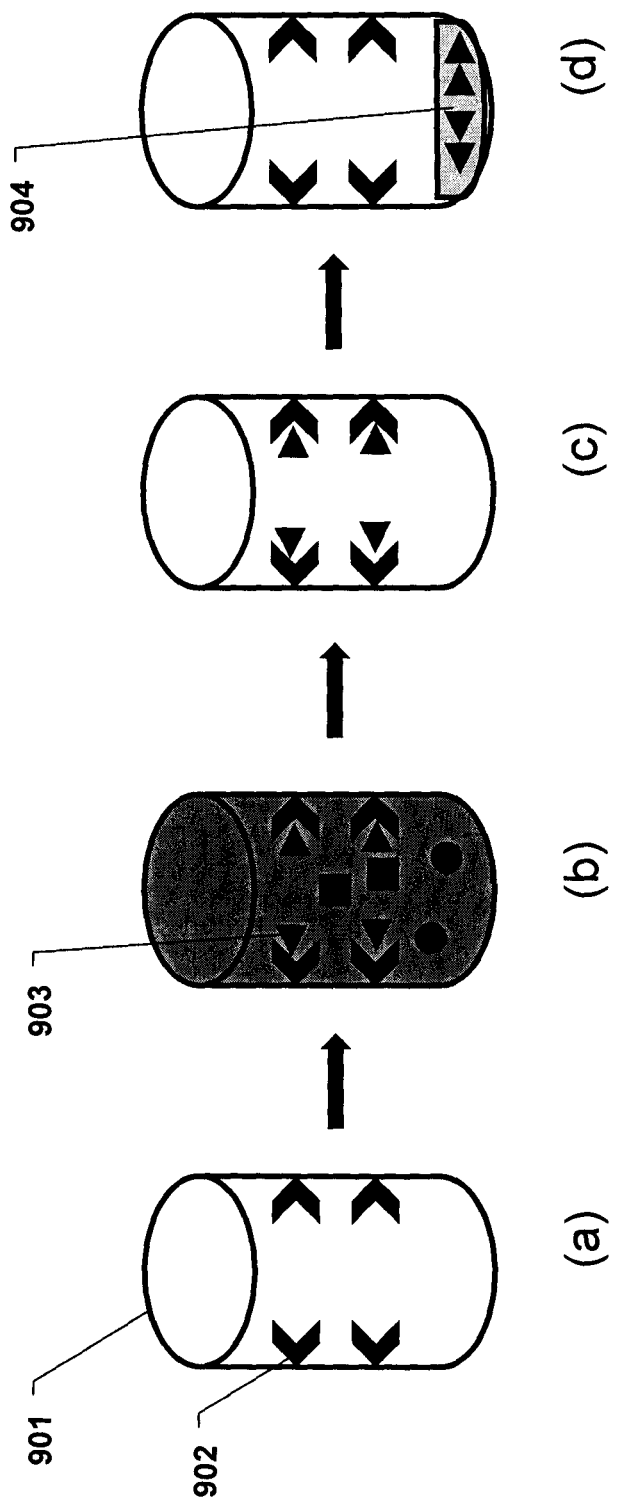
FIG. 9 (Panels a-d) is a collection of drawings illustrating a sampling container. Panels a-d show the sequential working steps for transporting and/or analysis of the generated samples. Panel a shows substrates which selectively bind to analytes of interest are coated on the inside surface of the container. The analytes in the liquefied tissue samples are selectively captured by the coated substrates (Panel b). Upon sufficient incubation of the tissue sample, the sample is discarded while the analytes are held in the container (Panel c). The analytes are eluted by a buffer for subsequent analysis (Panel d).
Figure 10:
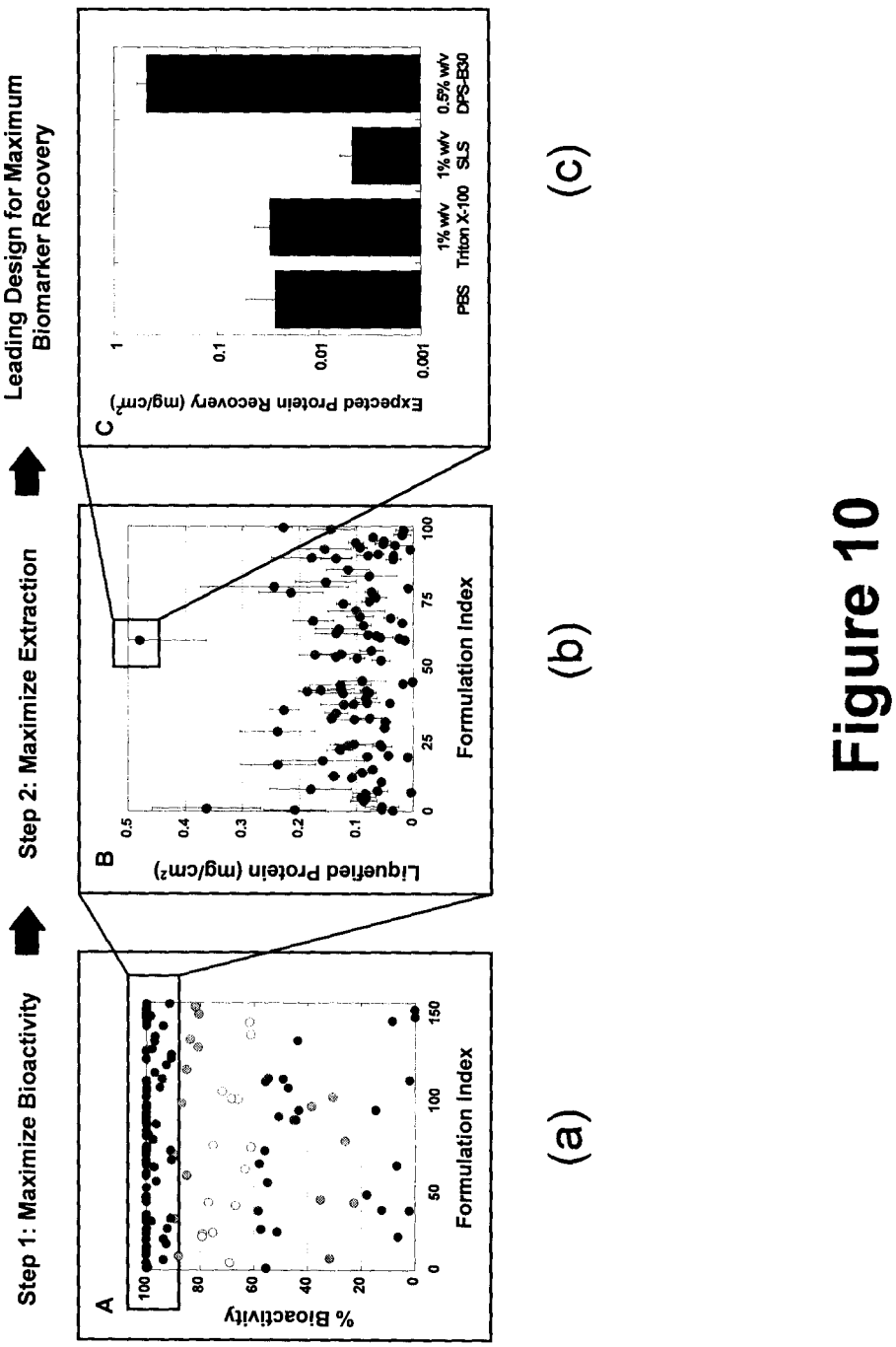
FIG. 10 (Panels a-c) is a collection of drawings illustrating the screening methodology for identifying unique surfactant formulations of LPMs. Panel a ranks over 150 surfactant formulations in their ability to preserve protein bioactivity. Panel b ranks best formulations from Panel a on their tissue solubilization potential. Panel c compares the best LPM from entire screening—0.5% (w/v) DPS-Brij30 with other conventional surfactants in their potential to sample functional proteins from skin tissue.
Figure 11:
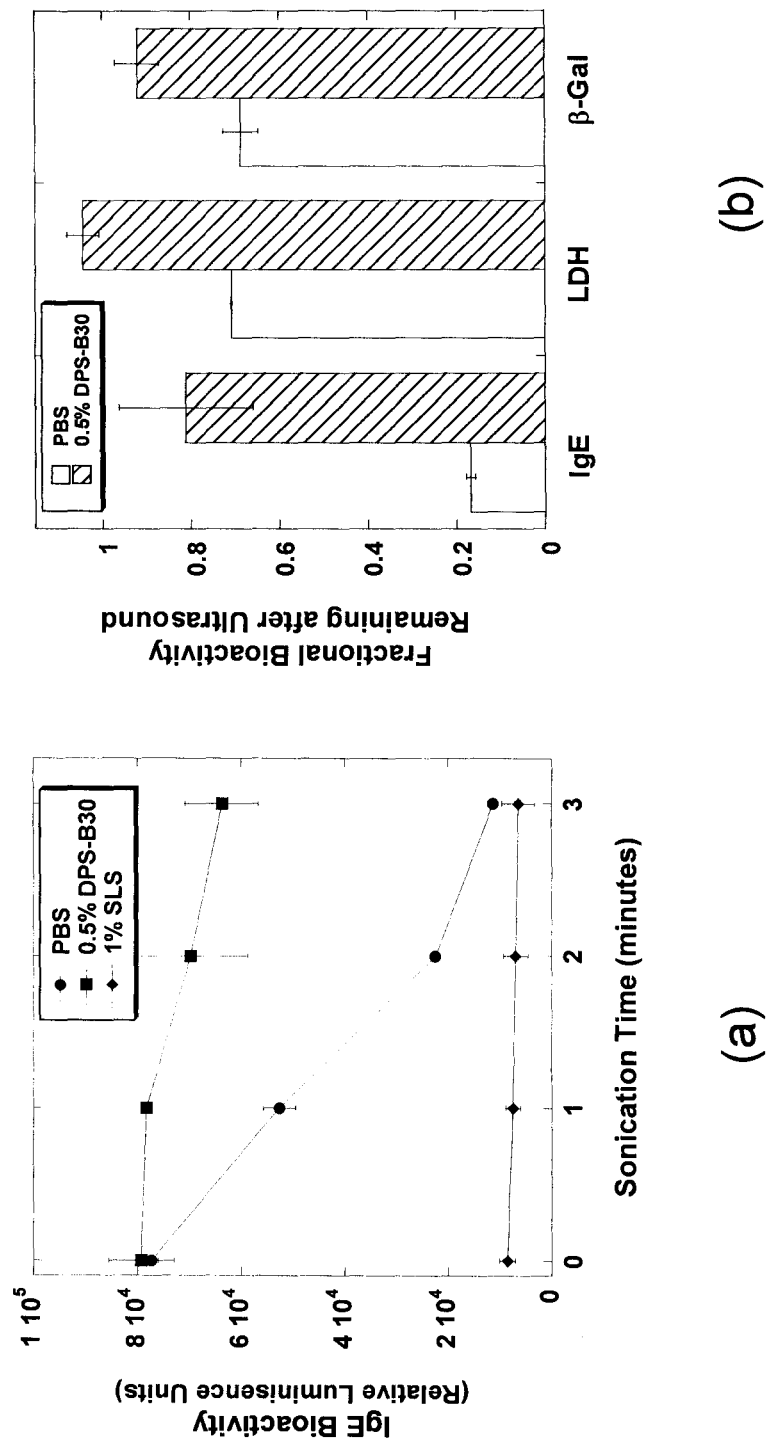
FIG. 11 (Panel a-b) is a collection of drawings illustrating LPM-assisted preservation of bioactivities of various proteins (IgE—panel a; IgE, LDH and β-gal—panel b) under mechanical stress of ultrasound exposure.
Figure 12:
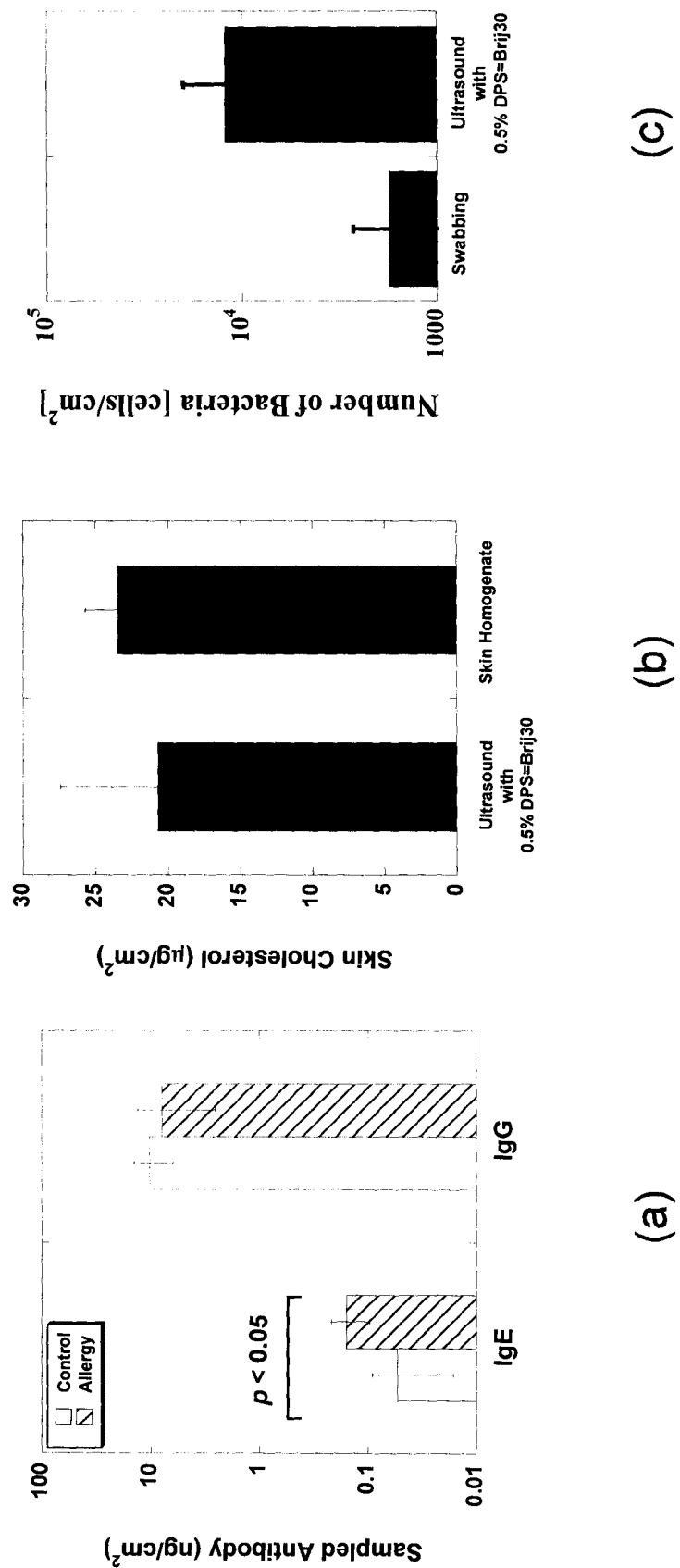
FIG. 12 (Panel a-c) is a collection of drawings illustrating the ability of ultrasonic exposure in the presence of LPM (saline solution of 0.5% (w/v) DPS-B30) to sample a variety of functional disease biomarkers (IgE—Panel a; Cholesterol—Panel b; Bacteria—Panel c) from skin tissue.

Referring to FIG. 9 (Panels a-d) a design for a reservoir housing to capture tissue analytes from liquefied tissue samples is described. The reservoir housing (901) is intended to be used with energy-application devices described herein, as a container to collect the liquefied tissue sample. The housing is coated with capture substrates (902) which selectively bind to tissue analytes (903) present in the sample. Upon sufficient incubation of the tissue sample, the sample is discarded while the analytes (903) are held in the housing. The analytes are eluted by an elution buffer in the housing for subsequent capture of the analytes as a separate sample (904). Alternatively, the housing can be integrated in an analytical tool for analyzing the bound analytes (903).

Example 4

Surfactant Formulations for Enhanced Tissue Solubilization and Protein Functionality Retention Unique surfactant formulations were identified that make up the liquefaction promoting medium (LPM) according to the definition disclosed in this text. A library of 153 binary surfactant formulations was created using 19 surfactants belonging to four distinct categories: (i) anionic surfactants (sodium lauryl sulfate (SLS), sodium laureth sulfate (SLA), sodium tridecyl phosphate (TDP), sodium deoxycholate (SDC), sodium decanoyl sarcosinate (NDS), sodium lauroyl sarcosinate (NLS), sodium palmitoyl sarcosinate (NPS)); (ii) cationic surfactants (octyl trimethyl ammonium chloride (OTAB), dodecyl trimethyl ammonium chloride (DDTAB), tetradecyl trimethyl ammonium chloride (TTAB)); (iii) zwitterionic surfactants (3-[(3-Cholamidopropyl) dimethyl ammonio]1-propane sulfonate (CHAPS), 3-(Decyl dimethyl ammonio) propane sulfonate (DPS), 3-(Dodecyl dimethyl ammonio) propane sulfonate (DDPS)); (iv) nonionic surfactants (Polyethylene glycol dodecyl ether (B30), Polyoxyethylene 23-lauryl ether (B35), Polyoxyethylene 10-cetyl ether (B56), Polyoxyethylene 2-stearyl ether (B72), Polyethylene glycol oleyl ether (B93), Nonylphenol polyethylene glycol ether (NP9)). Only a handful of surfactants from these categories (for example, nonionic surfactants) have been traditionally utilized for extracting functional tissue proteome. Additionally, these surfactants are highly limited in their ability to efficiently solubilize tissue constituents. As such, across all surfactant types, extraction potential and bioactivity preservation of tissue constituents are largely considered as mutually conflicting properties. By combining nonionic surfactants with other types of surfactants that have been previously described for their high solubilization ability (anionic, cationic and zwitterionic surfactants), we show the discovery of new families of surfactant formulations that simultaneously possess superior solubilization as well as non-denaturing capabilities.

The surfactant library was first screened for identifying non-denaturing surfactant formulations that retain protein bioactivity in extracts, and subsequently ranked for the ability of formulations to solubilize tissue proteins. FIG. 10a shows the potency of 153 surfactant formulations to preserve the specific functionality of a model protein—IgE antibody. Specifically, binding ability of IgE antibody with ovalbumin was tested. The x-axis in this figure represents the formulation index unique to each binary formulation. The y-axis represents % IgE bioactivity retention, defined as the fractional IgE binding activity in surfactant formulation compared with IgE binding activity when surfactants in pure solvent (phosphate buffered saline, PBS). The formulations spanned a wide range of denaturing potentials. Surprisingly, an increasing number of denaturing surfactants upon combination with gentler nonionic surfactant yielded a high synergistic gain in IgE functionality retention. Non-denaturing potential, averaged over all binary surfactant formulations was found to be significantly higher than their constituent single surfactant formulations ($p<0.006$; two-tailed heteroscedastic student's t-test); further demonstrating unique synergic interactions.

Surfactant formulations exhibiting high bioactivity retention (≥90%) were further screened for their ability to extract tissue proteins in conjunction with a brief sonication treatment. Porcine skin was used as a model tissue for these studies. While a majority of formulations revealed an extraction potential close to 0.1 mg protein per $cm^2$ of skin tissue, only a couple of formulations achieved protein extraction exceeding 0.3 $mg/cm^2$ (FIG. 10*b*).

The leading candidates screened from the surfactant library generally resulted in formulations that were exceptionally non-denaturing, yet more effective in solubilizing tissues than some of the most widely used extraction surfactants reported in the literature. FIG. 10*c* compares the leading surfactant formulation—0.5% (w/v) DPS-B30, with 1% (w/v) SDS for skin sampling. Despite a moderate extraction ability ($0.16\pm0.07$ $mg/cm^2$), SDS is highly denaturing which results in a low yield of functional protein recovery (product of fractional bioactivity retained and total extracted protein). In contrast, 0.5% (w/v) DPS-B30 formulation not only extracts more skin proteins ($0.48\pm0.12$ $mg/cm^2$) but also preserves protein activity, amounting to an excess of 100-fold enhancement in expected functional protein recovery over SDS. Similarly, more than 10-folds of protein recovery were accomplished over commonly used non-denaturing surfactant 1% (w/v) Triton X-100 and PBS.

Example 5

Bioactivity Retention Under Stress

We show that unique surfactant formulations, or LPMs (as indentified by method described in Example 1) additionally protect a variety of analytes under stress. We specifically show denaturing effects of mechanical energy such as ultrasound exposure (a commonly known denaturant to biomolecules), can be neutralized with the use of unique surfactant formulations.

In separate experiments, a globular protein (IgE) and two representative enzymes—lactate dehydrogenase (LDH) and beta-galactosidase (β-Gal) were dissolved in 0.5% (w/v) DPS-B30 surfactant formulation and sonicated to determine retention of protein bioactivity over time. Proteins dissolved in saline (PBS) were prepared as comparative controls. A progressively sharp decrease in functionality was observed for IgE dissolved in PBS; however, 0.5% (w/v) DPS-B30 formulation, surprisingly, extended protection to IgE proteins towards ultrasonic denaturing stress (FIG. 11*a*). Irrespective of ultrasound treatment, IgE dissolved in SDS showed complete state of denaturation. Similar trends were observed on extended preservation of enzymatic activities for LDH and β-Gal prepared in 0.5% (w/v) DPS-B30 formulation (FIG. 11*b*). Protein preparation in PBS resulted in significant loss of bioactivity ($p<0.006$; two-tailed heteroscedastic student's t-test), amounting to a fractional bioactivity of 16.7% (IgE), 70.8% (LDH) and 68.7% (β-Gal) after 3 minutes of sonication.

Example 6

Tissue Sampling And Molecular Diagnostics

The ability of ultrasonic exposure in the presence of LPM (saline solution of 0.5% (w/v) DPS-B30) to sample a variety of functional disease biomarkers from tissues was demonstrated.

Sampling of allergy-specific IgE antibodies from the skin of mice allergic to egg was demonstrated. Six to eight weeks old female BALB/CJ mice were purchased from Charles River Labs (Wilmington, Mass.) and maintained under pathogen-free conditions. Allergic reaction was induced in mice by an epicutaneous exposure protocol. After anesthesia with 1.25-4% isofluorane in oxygen, the skin on the back of the mice was shaved and then tape stripped 10-times (Scotch Magic tape, 3M Health Care, St Paul, Minn.) to introduce a standardized skin injury. A gauze patch (1 cm×1 cm) soaked with 100 μL of 0.1% OVA was placed on the back skin and secured with a breathable elastic cloth-based adhesive tape. The patches were kept affixed for 1 week. The whole experiment comprised a total of three 1-week exposures with a 2-week interval between each exposure week. Sampling was performed by gluing a custom made flanged chamber (skin exposure area of 1.33 $cm^2$) to the shaven skin area with a minimal amount of cyanoacrylate-based adhesive. The chamber was filled with 1.8 ml of 0.5% (w/v) DPS-B30 surfactant formulation and 20 kHz ultrasound was applied at 50% duty cycle, 2.4 $W/cm^2$ for 5 minutes. Skin biopsies of ultrasound treated or untreated eczema skin sites were obtained, and skin homogenate samples were prepared as positive controls. FIG. 12*a* shows that ultrasound-assisted sampling successfully sampled significantly more amount of allergy-specific IgE antibodies from allergic mice skin as compared to healthy mice. Expectedly, no difference was seen in the amount of IgG antibodies in the samples from allergic and healthy mice skins.

Sampling of cholesterol from mouse skin was also demonstrated. With similar procedures as described in above paragraph, skin samples with the ultrasound procedure were collected. Skin homogenates were prepared as positive controls from biopsies collected from untreated skin. Skin cholesterol is an important biomarker for diagnosing cardiovascular disease [1]. FIG. 12*b* shows that ultrasound-assisted sampling successfully samples cholesterol from skin and the amount sampled is comparable to the cholesterol present in skin homogenate.

Lastly, sampling of bacterial genome from porcine skin was demonstrated. Tissues, particularly skin and mucosal membranes are colonized by a diverse set of microorganisms including bacteria, fungi and viruses [2-5]. Accurate diagnosis of bacterial infection leads to appropriate patient management, providing information on prognosis and allowing the use of a narrow-spectrum antibiotics [6-8]. Thus, definitive microorganism detection is essential for diagnosis for treatment of infection and trace-back of disease outbreaks associated with microbial infections. Accurately obtaining samples which represent microorganisms on skin, however, is a major challenge [2]. The most practical method of collection would be swabbing because it is simple, quick and non-invasive [3, 9]. However, swabbing has several limitations including poor recoveries of the microorganisms and lack of a standardized protocol, which suggests it either does not accurately represent the microorganisms on the skin or provide quantitative data. Ultrasound-assisted sampling can effectively address these limitations. In particular, excised porcine skin was sampled by swabbing with a cotton ball soaked in saline (PBS), and by ultrasound-assisted sampling with 0.5% (w/v) DPM-Brij30 as LPM in separate experiments. The bacterial genome was purified from each sample by standard phenol-chloroform extraction method. Briefly, samples were first incubated in a solution consisting of 20 mM Tris at pH 8.0 (BP154-1, Fisher Scientific), 2 mM EDTA (BP120-500, Fisher Scientific), 1.2% Triton X-100 (BP151-100, Fisher Scientific), and 20 mg/ml lysozyme (62970-1G-F, Sigma-Aldrich) for 30 min at 37° C. [9]. Subsequently, samples were incubated for 3 hours at 37° C. in a solution consisting of 0.1 mg/ml Proteinase K (P2308-25MG, Sigma-Aldrich), 0.5% (w/v) sodium lauryl sulfate (S529, Fisher Scientific), and 100 mM sodium chloride (BP358-1, Fisher Scientific). Genomic DNA was then extracted with an equal volume of phenol (P4557, Sigma-Aldrich), followed by extraction with phenol/chloroform/isoamyl alcohol, 25:24:1 (P2069, Sigma-Aldrich). The DNA was precipitated by incubation with ethanol and centrifugation for 20 min. The DNA pellets were washed twice with 70% ethanol, allowed to dry, and resuspended in 80 μl of tris buffer. The amount of bacteria sampled by each methodology was evaluated by determining the presence of the conserved 16S bacterial gene in each sample using quantitative-polymerase-chain-reaction (qPCR). FIG. 12c shows that ultrasound-assisted sampling sampled at least 7-fold higher amount of bacterial genome from skin than the conventional cotton swabbing procedure.

Example 7

Buffer Design of LPMs Compatible With Nucleic-Acid-Based Tests

To ensure compatibility of the liquefied tissue samples with subsequent analysis, the components of LPMs have to be carefully chosen. Compatibility of several LPM components with nucleic-acid-based analytical technique was tested. Specifically, the compatibility of LPM components with qPCR—the most common gene-based test, was evaluated by measuring the test's ability to amplify plasmid DNA added in different LPMs.

Ten million copies of Luciferase plasmid (E1741, Promega Corp.) were spiked in 10 μl of different solutions: (i) water, (ii) 0.91% (w/v) sodium chloride (BP358-1, Fisher Scientific) in water, (iii) PBS (P4417, Sigma-Aldrich), (iv) 10 mM Tris-HCl, pH 7.9 (BP154-1, Fisher Scientific), (v) 0.075 M sodium phosphate buffer, pH 7.9, derived from sodium phosphate monobasic monohydrate and sodium phosphate dibasic (S9638-25G, 57907-100G, Sigma-Aldrich), and (vi) 0.5 mM EDTA (BP120-500, Fisher Scientific) in water. The solutions were combined with 10 μl of PCR reaction buffer. Luciferase amplification primers were 5'-GCC TGA AGT CTC TGA TTA AGT-3' for the forward primer and 5'-ACA CCT GCG TCG AAG-3' for the reverse primer, creating an amplicon of 96 bp [10]. Amplification reactions were performed in a 20 μl solution containing MgCl$_2$ at 1.5 mM, primers at 0.2 μM (each), and 0.2 mM dNTPs in PCR buffer and 0.025 units/μl of Taq polymerase (10966-034, Invitrogen) and SYBR-green (S-7563, Invitrogen) at 1:45,000. Aliquots of plasmid DNA were diluted in water to generate a standard curve. Analysis was performed on iCycler PCR machine (Bio-Rad Laboratories, Inc.) using optical grade 96-well plates. Thermal cycle of the reaction was set as follows: initial denaturation at 95° for 3 min, followed by 40 cycles of denaturation at 95° C. for 30-sec, 30-sec annealing at 60° C., and 30-sec elongation at 72° C., all followed by a final extension of 10 min at 72° C. For each sample, three replicates were performed. For each buffer, the compatibility was calculated by comparing with the control (plasmid DNA in water).

Figure 13:
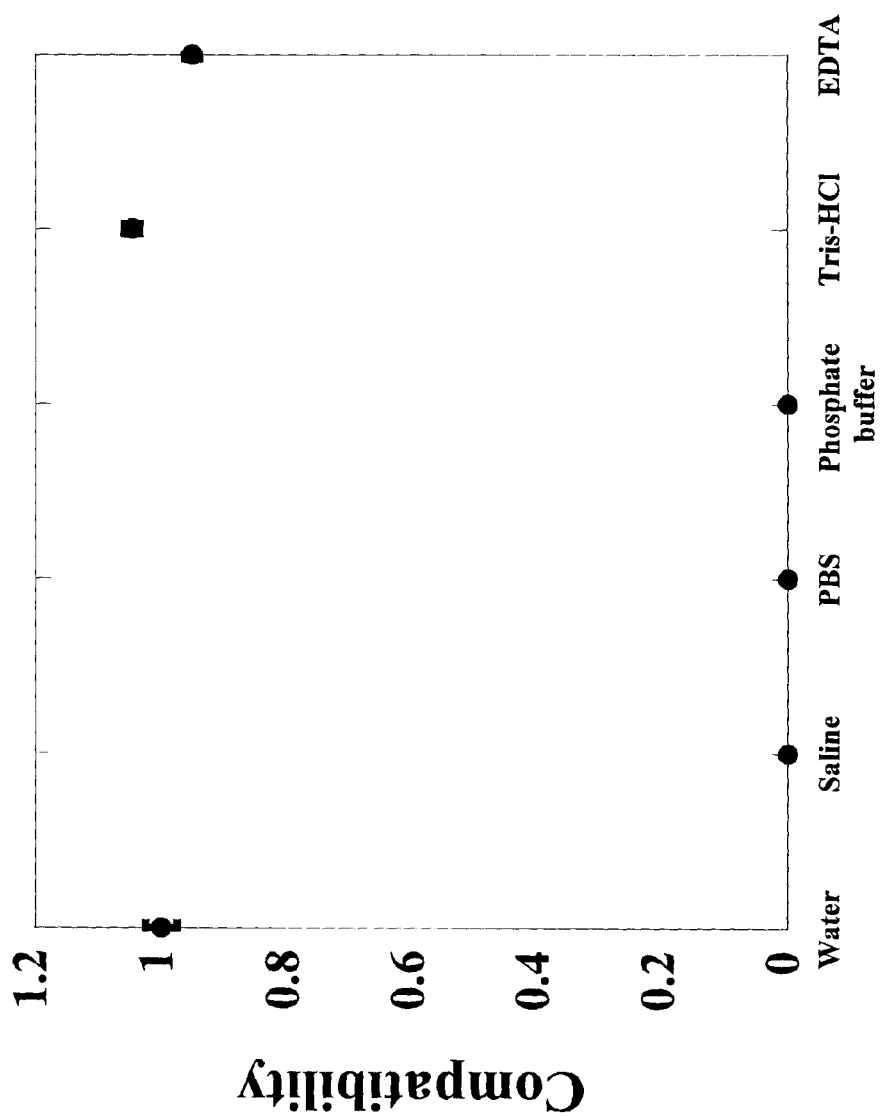
FIG. 13 is a graph illustrating the effect of buffers in LPMs on the compatibility with quantitative PCR.

FIG. 13 shows that sodium chloride, PBS, and sodium phosphate buffer was incompatible as detection buffer for quantitative PCR assay as compared with control. However, use of tris-HCl or EDTA as buffer increased the analytical assay's detection ability.

Example 8

Compatibility of LPMs With Nucleic-Acid-Based Tests

Compatibility of various LPMs (disclosed in EXAMPLE 1) with existing nucleic-acid-based tests was tested. Specifically, plasmid DNA was mixed with different LPMs and the ability of qPCR to amplify DNA was assessed. LPMs were prepared by adding surfactants at various concentrations in 10 mM Tris-HCl buffer. To mimic the process of tissue liquefaction as disclosed in this text, each LPM was mixed with 0.2 mg/ml of pig skin homogenate and ten million copies of Luciferase plasmid (E1741, Promega Corp.) were spiked per 10 μl of LPM. This solution was combined with 10 μl of PCR reaction buffer. qPCR was performed according to the protocol described in Example 4. Purified plasmid DNA were diluted in a tris-HCl solution to generate a standard curve. Compatibility of each LPM was calculated by detrmining the amount of plasmid amplified by qPCR and comparing it with the control buffer (plasmid DNA in tris-HCl without surfactant).

Figure 14:
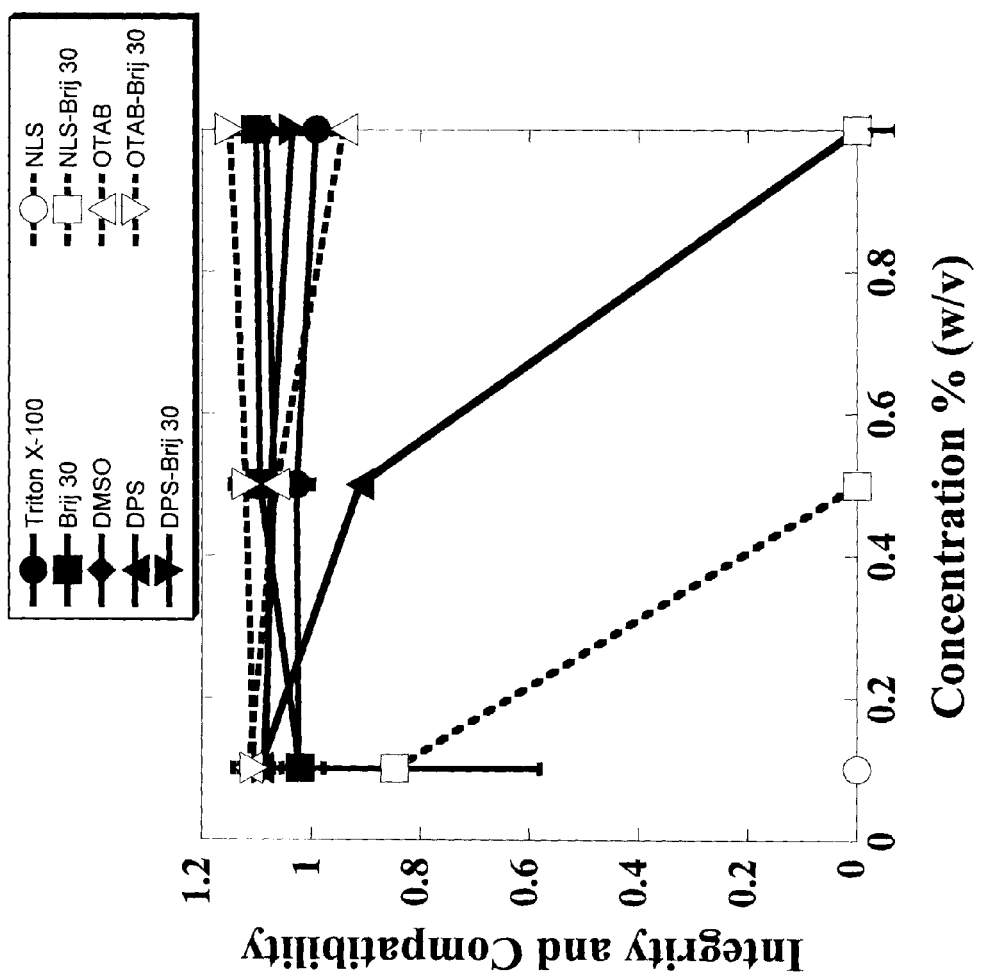
FIG. 14 is a graph illustrating the influence of surfactant mixture on the compatibility with quantitative PCR.

FIG. 14 shows that Triton X-100, Brij 30, DMSO, OTAB, OTAB-Brij 30, and DPS-Brij 30 were highly compatible with quantitative PCR; however LPMs consisting of NLS or NLS-Brij30 failed to amplify the DNA. Notably, DPS-Brij 30 as a LPM effectively samples biomolecules from tissues, retains protein activity and is compatible with analytical methods including ELISA, chromatography and qPCR. Therefore, DPS-Brij 30 is most desirable as liquefaction promoting media for analyzing proteins, lipids and nucleic acids. Triton X-100 and DMSO, which have been known as a facilitator of PCR [11], were consistently shown to effectively produce polymerase-chain reactions; however, they do not yield satisfactory tissue extraction.

Example 9

Identification of Ultrasonic Parameters for Sampling Viable and Genetically-Intact Microorganisms From Tissues This example describes a nonlethal condition of ultrasound to efficiently collect living microorganisms from tissues. Microorganisms can be collected from tissue by applying various form of energy to tissues; however use of high energies is highly detrimental to the viability of microorganisms. Therefore, it is essential to find out nonlethal conditions of energy application for sampling living microorganisms. We describe ultrasound exposure conditions for sampling viable and genetically-intact bacteria from skin.

Bacterial culture of E. Coli strain DH10α (18290-015, Invitrogen) were grown in Luria-Bertani (BP1426, Fisher Scientific) at 37° C., 250 rpm or as solid culture on Agar plates (37° C.). Culture was harvested by centrifugation and the resulting pellet was suspended in LPM comprising of 10 mM Tris-HCl, pH 7.9 at a concentration of $10^9$ cells/ml. E. Coli cells were quantified with a spectrophotometer (Biophotometer, Eppendorf), and a bacterial culture of $0.25 \times 10^9$ cells/ml was considered to correspond to an optical density absorbance value of 0.25 at a wavelength of 600 nm. One ml of the resuspended cells was placed in a sterilized cylindrical container (internal diameter 20 mm, flat base, 1.3 mm wall thickness, 31 mm height). All experiments were performed with a 600-Watt sonicator (Sonics & Materials, Newtown, Conn.)

operating at a frequency of 20 kHz at 50% duty cycle. The power setting and the time of ultrasound exposure were varied in this experiment. The transducer was lowered into the container until the probe was immersed in the fluid at a distance of 5 mm from the bottom. The transducer was sterilized by 70% ethanol between sonication procedures on different samples. After sonication, 10-fold serial dilutions of each sample were prepared in 10 mM Tris-HCl (pH 7.9). 100 ul of sample from each dilution step was plated onto Luria-Bertani agar and spread with a sterile spreader. The plates were incubated at 37° C. for 24 h and viable bacterial colony counts were made on the surface of agar plates. Results were expressed as percentage reduction in viability relative to non-sonicated controls. To evaluate integrity of bacterial genome in samples exposed to ultrasound, electrophoresis was carried out. All samples were incubated at 56° C. in Proteinase K (19131, Qiagen) and 0.5% (w/v) sodium lauryl sulfate (S529, Fisher Scientific). After 1-h incubation, total genomic DNA was extracted by using the DNeasy DNA Extraction Kit (69504, Qiagen). The standard protocol for the kit was followed for all subsequent steps. The purified genomic DNA was resuspended in 400 µl of Buffer AE and stored at −20° C. until analysis. The purified DNA was electrophoresed for 90 min at 100 V in a 2% (w/v) Tris-acetate-EDTA-agarose gel. The gels were stained with SYBR Gold (S 11494, Invitrogen) and visualized under UV light.

Figure 15:
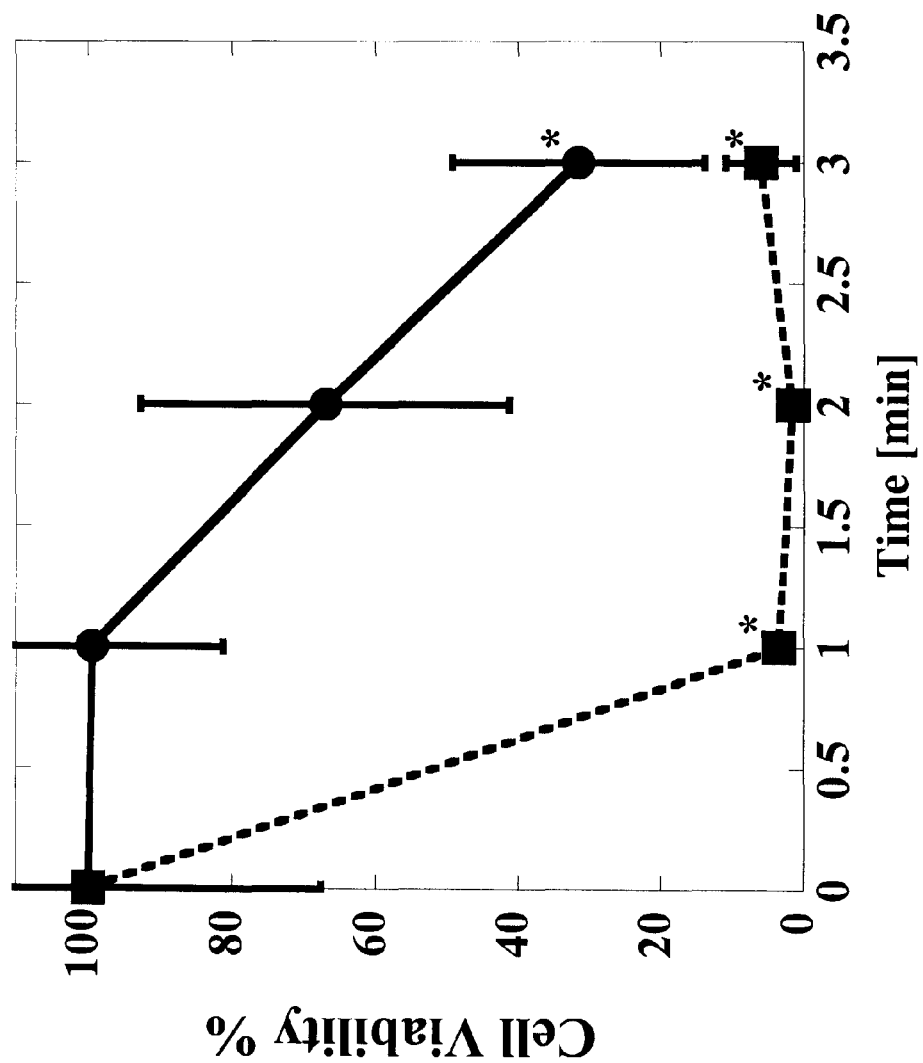
FIG. 15 is a graph illustrating the effect of ultrasound intensity and exposure time on $E.$ $Coli$ viability. Samples were exposed to ultrasound at intensities of 1.7 W/cm$^2$ (•) and 2.4 W/cm$^2$ (■). Each point represents the mean value from three independent samples.
Figure 16:
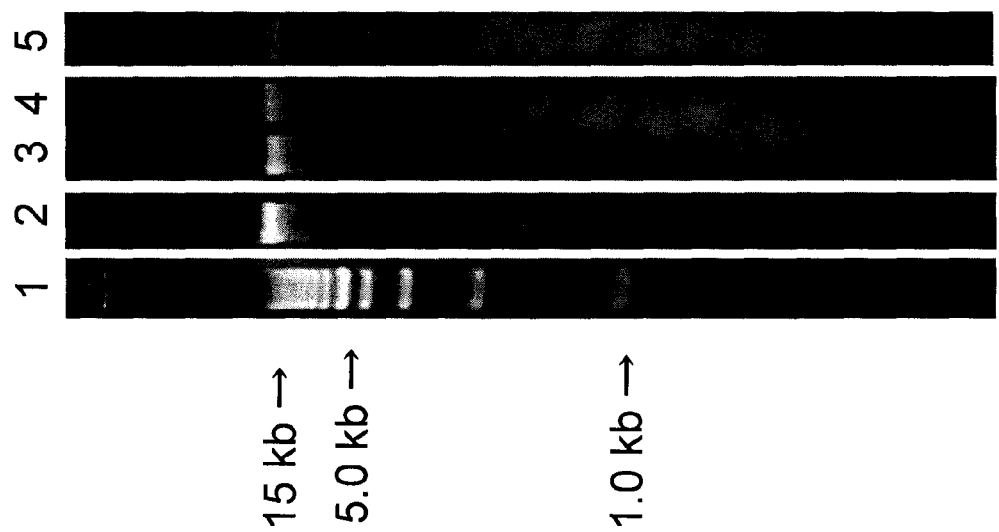
FIG. 16 is a photograph of agarose gel-electrophoresis of genomic DNA from $E.$ $coli$ cells sonicated at different conditions in tris-HCl. Lane 1 molecular standard; lane 2 Non-treated cell; lane 3 1.7 W/cm$^2$, 2 min; lane 4 1.7 W/cm$^2$ 3 min; lane 5 2.4 W/cm$^2$, 3 min.

FIG. 15 shows that viability of *E. coli* exposed to ultrasound at an intensity of 1.7 W/cm$^2$ for up to 2 min was statistically insignificant to the viability of non-treated *E. coli* samples. This suggests that these ultrasonic liquefaction conditions can be used for sampling bacteria without a major loss of viability. However, samples sonicated at higher power output exhibited a more rapid decrease with application time, and the cell viabilities were significantly different compared with non-treated cells. Even after 1 minute exposure at a higher intensity, viability was reduced to 3.6% ($p<0.05$). This observation is in agreement with bacterial genome integrity as assessed by electrophoresis (FIG. 16). No damage to bacterial genome was observed upon sonication for 2 minutes at 1.7 W/cm$^2$ (conditions shown to maintain cell viability); however, in contrast, the genomic DNA of *E. coli* cells sonicated at intensities of 1.7 W/cm$^2$ (32% viability) and 2.4 W/cm$^2$ (8% viability) for 3 min were highly fragmented as can be seen by their migration to lower molecular weight part of the gel. These results suggest that collection of living bacteria should be performed at an ultrasound intensity of 1.7 W/cm$^2$ for up to 2 min.

Example 10

Detection of Living Microorganisms from Tissues

A brief exposure of ultrasonic energy coupled with LPM (tris-HCl buffer) can sample viable bacteria from skin. Skin bacteria sampled by ultrasound were quantified by the conventional colony counting assay as well as real-time quantitative PCR, and evaluated by comparing with standard sampling methods such as swabbing and the surfactant scrubbing technique.

In vitro experiments were performed on porcine skin to assess sampling of skin-resident bacteria. Pre-cut frozen full-thickness porcine skin harvested from the lateral abdominal region of Yorkshire pigs was procured in 10 cm×25 cm strips from Lampire Biological Laboratories Inc., PA. The skin was stored at −70° C. until the experiment. Skin pieces with no visible imperfections such as scratches and abrasions were thawed at room temperature and cut into small pieces (2.5 cm×2.5 cm) and mounted on a Franz diffusion cell (Permegear, Hellertown, Pa., USA). The receiver chamber of the diffusion cells was filled with phosphate buffered saline (PBS) (P4417, Sigma-Aldrich, St. Louis, Mo.) and the donor chamber (skin exposure area of 1.77 cm$^2$) was filled with 1 ml of 10 mM Tris-HCl buffer (pH 7.9), which also acted as the coupling fluid between the ultrasound transducer and skin. The ultrasound transducer was placed at a distance of 5 mm from the skin surface and an ultrasonic intensity of 1.7 W/cm$^2$ was applied for 2 minutes. The probe was disinfected with 70% ethanol between experiments on different samples. As comparative controls, samples were obtained by swabbing the skin. Cotton swabs (B4320115, BD Diagnostics) were soaked in sterilized phosphate-buffered saline before use. The area of the sample site was standardized by holding a sterilized metal ring enclosing an area of 3.3 cm$^2$ onto the skin surface. The skin surface was rubbed gently and repeatedly for approximately 20 seconds. Each swab was extracted with 1 ml of PBS. Skin bacteria were also sampled by the surfactant scrub technique of Williamson and Kligman [2, 12]. A sterile metal ring was firmly held against the skin surface and 1 ml of 0.1% Triton X-100 in 0.075 M phosphate buffer, pH 7.9, was pipette into it. The skin surface within the ring was rubbed firmly for 1 min with a Teflon cell scraper and the resulting sample was collected in a sterile centrifuge-tube. The procedure was repeated at the same skin site for two additional times and samples were pooled together. Serial 10-fold dilutions of each sample were prepared and 100 µl aliquots from each diluted sample were placed on Tryptic Soy agar plates (90002, BD Diagnostics) [12]. The plates were subsequently incubated under aerobic conditions at 37° C. for 24 hours and colonies were counted to obtain an estimate of extraction efficiency by calculating the colony-forming unit per unit area of sampled skin (CFU/cm$^2$). To quantify total bacteria, real-time quantitative PCR was performed based on an amplicon of the 16S rRNA gene. All biological specimens were first incubated in a preparation of enzymatic lysis buffer (20 mM Tris at pH 8.0, 2 mM EDTA, 1.2% Triton X-100) and lysozyme (20 mg/mL) for 30 min at 37° C. [9]. Subsequently, samples were incubated for 1 hour at 56° C. in Buffer AL and Proteinase K from the DNeasy DNA Extraction Kit (Qiagen). The standard protocol for the kit was followed for all subsequent steps. The DNA eluted by Buffer AE was precipitated by incubation with equal volumes of absolute isopropanol and then centrifuging for 20 min. The DNA pellets were washed once with 70% ethanol, allowed to dry, and resuspended in 80 µl of Buffer AE. Negative controls were also prepared using untreated sterile cotton swabs in PBS. Analysis of the 16S genes was performed on the iCycler PCR machine (Bio-Rad Laboratories, Inc.) using optical grade 96-well plates. A portion of the bacterial 16S gene was amplified using forward primer 63F (5'-AGAGTTTGATCCTG-GCTCAG-3') and reverse primer 355R (5'-GACGGGCGGT-GTGTRCA-3 [9, 13]. A standard curve was constructed by amplifying serial dilutions of genomic DNA from known quantities of *E. Coli* cells in 10 µl of Buffer AE. 10 µl of purified DNA was mixed with 2 pmol of each primer and Platinum PCR Supermix (11784, Invitrogen) to a final reaction volume of 20 µl Thermal cycling was set as follows: initial denaturation at 94° for 5 min, followed by 32 cycles of a 30-sec 94° C. denaturation, 30-sec annealing at 66° C., and 30-sec elongation at 72° C., all followed by a final extension of 10 min at 72° C. For each sample, three replicates were performed.

Figures 17A, 17B:
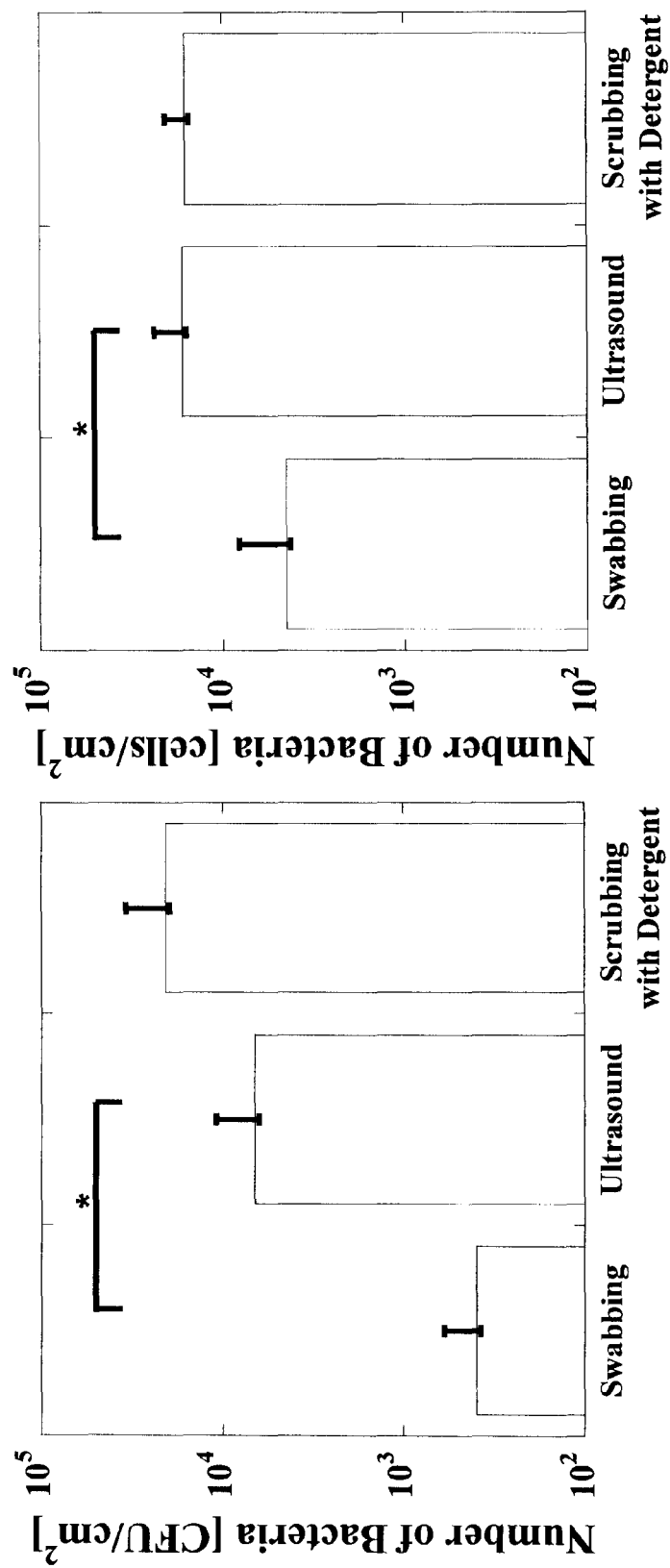
FIG. 17 (Panels a and b) is a graph illustrating the number of bacteria sampled by ultrasound coupling with tris-HCl, swabbing, and surfactant scrub technique, measured by (a) culture assay and (b) quantitative PCR. Each point represents the mean value from five independent samples.

FIG. 17 shows comparison of the sampling efficacies of different techniques. FIG. 17a shows that ultrasonic sampling recovered approximately 17-fold higher number of bacteria from skin than cotton swabbing ($p<0.05$). Notably, counts of the total number of bacteria collected by ultrasound did not differ significantly from the positive control (surfactant scraping method). The effectiveness of ultrasonic sampling was further tested using quantitative real-time PCR based on amplifying the 16S rDNA bacterial gene (FIG. 17b). Consistently, ultrasound collected $1.7 \times 10^4$ bacteria/cm$^2$ which is significantly higher than swabbing ($4.5 \times 10^3$ bacteria/cm$^2$), and equivalent to scrubbing technique ($1.6 \times 10^4$ bacteria/cm$^2$).

Example 11

Use of Sensitivity Enhancers to Facilitate Detection of Human IgE in LPM

The ability of sensitivity enhancers to facilitate detection of a model analyte—human IgE antibody, which was dissolved in a model LPM—1% w/v NLS-Brij 30 in a PBS, was tested. ELISA assay was used to evaluate detection of human IgE antibody in presence or absence of sensitivity enhancers in LPM. Specifically, 1 microgram of antibodies (A80-108A, Bethyl laboratory, TX) with specific binding to human IgE antibodies was coated per well of a 96-well ELISA plate. Human IgE (RC80-108, Bethyl laboratory, TX) was dissolved in the LPM with or withour sensitivity enhancer at a concentration of 0-100 ng/ml. As a positive control, human IgE samples were prepared by dissolving in a standard diluent containing 1% w/v BSA and 0.05% w/v Tween 20 (P7949, Sigma-aldrich, MO) in 50 mM Tris-buffered saline (T6664, Sigma-aldrich, MO) which is commonly used in immunoassays. Two types of sensitivity enhancers were formulated: 10% BSA and 0.5% Tween 20 in PBS and 10% BSA and 0.5% Tween 20 in 50 mM Tris-buffered saline. Each of these sensitivity enhancers was separately added to LPM containing IgE in a ratio of 1:10. After 30-minutes incubation of ELISA plates with a standard blocking buffer, these samples were incubated in individual wells for 1 hour. After washing the wells, HRP-conjugated-secondary antibodies at a concentration of 1 microgram/ml were incubated in each well for 1 hour. After washing, a HRP-based chemiluminescence signal (induced by substrates 54-61-00, KPL, MD), signifying detection ability of IgE antibodies by ELISA, was measured for each test case using a spectrophotometer.

Figure 18:
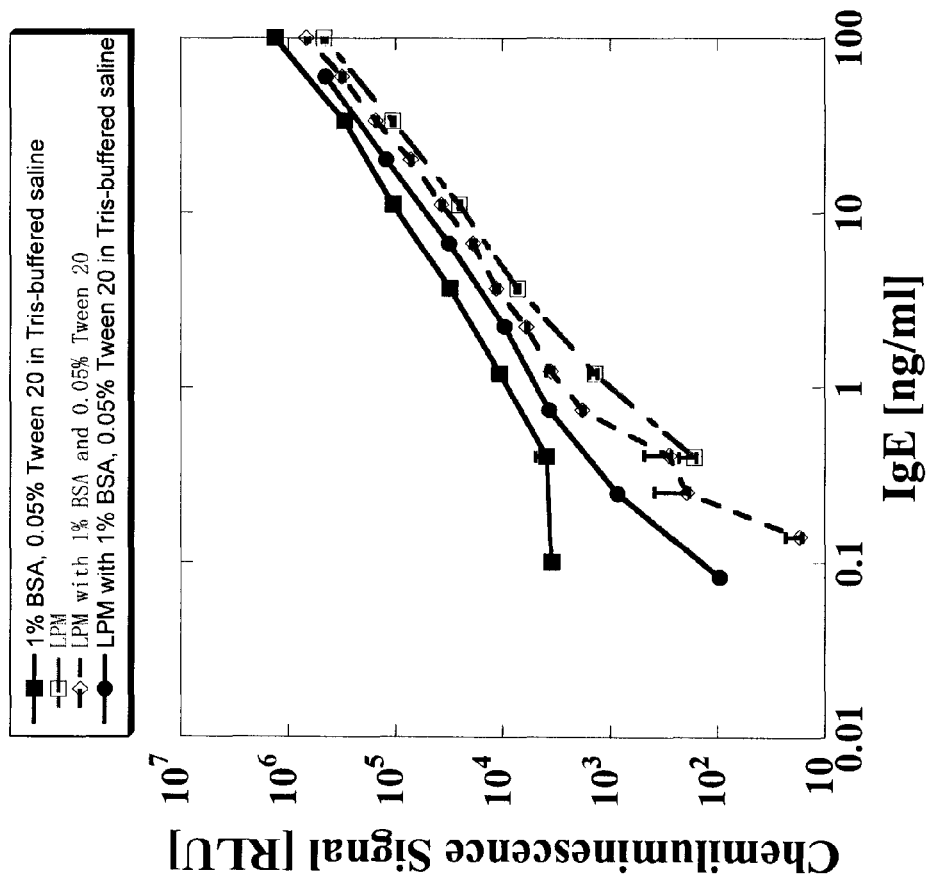
FIG. 18 is a graph illustrating the effect of adding various sensitivity enhancers in LPM for enhanced detection of a model analyte—human IgE antibody, in it. Sensitivity enhancers used in the analysis are a mixture of 10% w/v BSA and 0.5% w/v Tween 20 in phosphate-buffered saline (PBS) (open diamond); and a mixture of 10% w/v BSA and 0.5% w/v Tween 20 in tris-buffered saline (closed circle). Prior to analysis, each of the sensitivity enhancers was diluted at 1:10 ratio with LPM containing model analyte. As a control, LPM containing model analyte (open square) and a commonly-used analytical solvent comprising of a mixture of 1% w/v BSA and 0.05% w/v Tween 20 in tris-buffered saline (solid square) were used. The LPM was composed of a solution of 1% w/v mixture of NLS and Brij 30 in PBS. Error bars indicate the standard deviation.

FIG. 18 plots the chemiluminescence signal intensity from various test cases as a function of analyte concentration. Results show that LPM by itself was not a suitable detection reagent for ELISA assay as compared with positive control. However, adding sensitivity enhancers to LPM increased the analytical assay's detection ability. Additionally, tris-buffered saline was shown to elevate the signal intensity as compared with phosphate-buffered saline, when they are used as solvents to prepare sensitivity enhancers. These results demonstrated that LPM by itself is not efficient in facilitating analyte detection by ELISA; however, addition of sensitivity enhancers can significantly enhance detection ability of analytes by ELISA.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

Example 12

Delivery of Inulin and Acyclovir into Pig Skin

Drug delivery experiments were performed on pig skin in vitro. Pre-cut frozen full-thickness porcine skin, harvested from the lateral abdominal region of Yorkshire pigs, was obtained from Lampire Biological Laboratory, Inc., PA. The skin was stored at −80° C. freezer prior to the experiment. The skin was thawed at room temperature, and the skin with no visible imperfections such as scratches and abrasions were cut into small pieces (2.5×2.5 cm). Skin pieces were mounted on to a Franz diffusion cell (PermeGear, Inc., PA). Before each experiment, the receiver compartment was filled with a LPM or phosphate buffer saline (PBS). A 1%-w/v mixture of NLS and Brij 30 in PBS was chosen as a model formulation of a LPM. Prior to each experiment, the electrical conductivity of the skin was measured to ensure its integrity. The skin was considered damaged if the initial conductivity was more than 2.2 microA/cm$^2$. Ultrasound was applied using a sonicator (VCX 400, Sonics and Materials) operating at a frequency of 20 kHz at an intensity of 2.4 W/cm$^2$ for 5 minutes. After the LPM or PBS was removed, the donor compartment was filled with 10 microCi/ml solution of Inulin (NET086L001MC, PerkinElimer Life and Analytical Sciences, Inc., MA) in PBS. Samples were taken from the receiver compartments 24 hours after ultrasound application. In a separate experiment, a rotating abrasive surface (a circular brush with plastic bristles) was introduced in the donor chamber such that it directly contacted the skin sample. 10 microCi/ml solution of Acyclovir was placed on the skin for 24 hours. The skin was washed by a saline and dissolved in Solvable (PerkinElmer, MA). The concentrations of those samples were measured by a scintillation counter (Tri-Carb 2100 TR, Packard, CT). All experiments were conducted at room temperature, 22° C. Neither ultrasound nor abrasive device was applied on the controls. Error bars indicate the standard deviation.

Figure 19B:
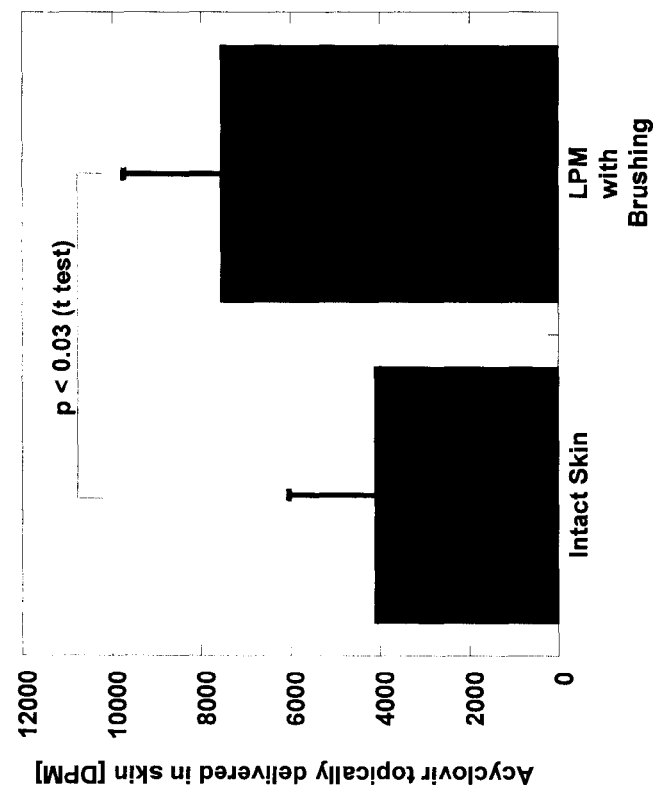
FIG. 19 (Panels a-b) is a collection of graphs illustrating delivery of Inulin across and of Acyclovir into pig skin in vitro after ultrasound application (a) or abrasion with a plurality of bristles (b).
Figure 19A:
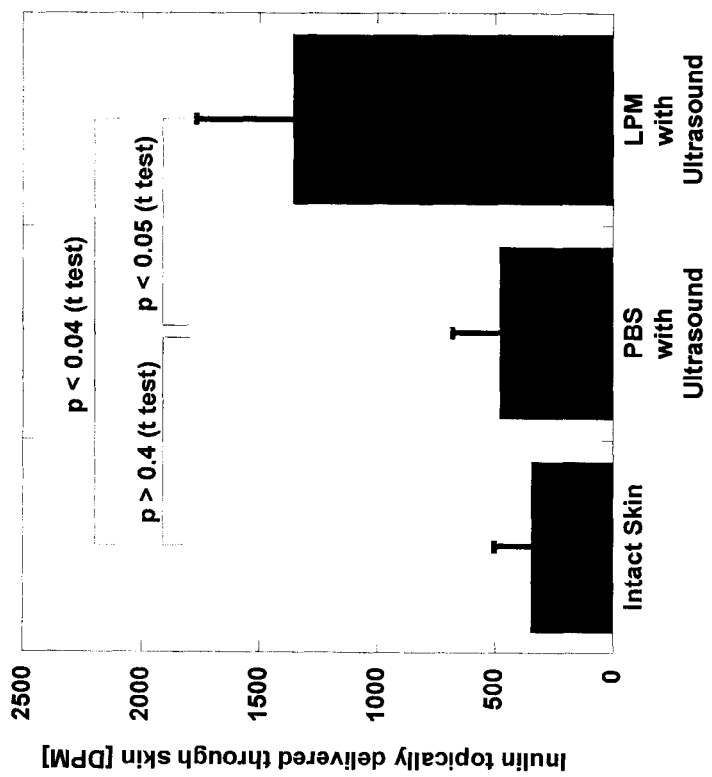

5 minutes of ultrasound irradiation in combination with the LPM increased drug transport, compared to that both by ultrasound alone and by the passive diffusion on intact skin, as shown in FIG. 19(a). The same effect was observed when the skin was abraded with a moving brushing device comprising a plurality of bristles (FIG. 19(b)). In summary, the examples using pig skin in vitro demonstrated that applying energy with a LPM is effective in enhancing the passage of molecules through or into tissues. Parameters such as power, time of application and a formulation of a LPM can be optimized to suit the individual situation, both with respect to the type of tissue and the substances to be transported.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A device for at least partly liquefying a tissue, comprising:
   a reservoir;
   an abrasive material operatively coupled to the reservoir, the reservoir being configured to transmit mechanical energy through the abrasive material to the tissue in the form of stirring, abrasion, pressure, or shear force; and
   a liquefaction promoting medium, the liquefaction promoting medium comprising a non-ionic surfactant and a zwitterionic surfactant, the zwitterionic surfactant comprising one or more of: 3-(decyl dimethyl ammonio) propane sulfonate, 3-(dodecyl dimethyl ammonio) propane sulfonate, myristyldimethyl ammonio propane sulfonate, hexadecyldimethyl ammonio propane sulfonate, cocamidopropyl betaine, oleyl betaine, cocamidopropyl hydroxysultaine, or 3-(3-cholamidopropyl)-dimethylammonio-1-propanesulfonate, and
   the reservoir being configured to be operatively connected to the tissue and to apply the liquefaction promoting medium to the tissue.

2. The device of claim 1, the liquefaction promoting medium comprising 3-(decyl dimethyl ammonio) propane sulfonate and polyethylene glycol dodecyl ether in a buffered solution.

3. The device of claim 1, a total concentration of the non-ionic surfactant and the zwitterionic surfactant (w/v) in the liquefaction promoting medium being between about 0.5% to about 10%.

4. The device of claim 1, the non-ionic surfactant and the zwitterionic surfactant being in a ratio of between about 25:75 and about 75:25.

5. The device of claim 1, the non-ionic surfactant comprising one or more of: polyethylene glycol dodecyl ether, polyoxyethylene 23-lauryl ether, polyoxyethylene 2-cetyl ether, polyoxyethylene 10-cetyl ether, polyoxyethylene 20-cetyl ether, polyoxyethylene 2-stearyl ether, polyoxyethylene 10-stearyl ether, polyoxyethylene 20-stearyl ether, polyoxyethylene 2-oleyl ether, polyoxyethylene 10-oleyl ether, polyoxyethylene 100-stearyl ether, or polyoxyethylene 21-stearyl ether.

6. The device of claim 1, the abrasive material comprising at least one of: a fabric, abrasive crystals, diamond dust, a polymeric sponge, a natural sponge, an abrasive disc, or a brush.

7. The device of claim 1, the abrasive material including a sponge, the sponge being configured to store the liquefaction promoting medium.

8. The device of claim 1, further comprising a plunger operatively connected to the reservoir and configured to apply the liquefaction promoting medium from the reservoir to the tissue.

9. The device of claim 1, at least a portion of the device being disposable.

10. The device of claim 1, the device being sterile.

11. A device for at least partly liquefying a tissue to form a liquefied tissue and delivering a drug to the liquefied tissue, comprising:
    a reservoir;
    an abrasive material operatively coupled to the reservoir, the reservoir being configured to transmit mechanical energy through the abrasive material to the tissue in the form of stirring, abrasion, pressure, or shear force;
    a liquefaction promoting medium, the liquefaction promoting medium comprising a non-ionic surfactant and a zwitterionic surfactant; and
    a drug,
    the zwitterionic surfactant comprising one or more of: 3-(decyl dimethyl ammonio) propane sulfonate, 3-(dodecyl dimethyl ammonio) propane sulfonate, myristyldimethyl ammonio propane sulfonate, hexadecyldimethyl ammonio propane sulfonate, cocamidopropyl betaine, oleyl betaine, cocamidopropyl hydroxysultaine, or 3-(3-cholamidopropyl)-dimethylammonio-1-propanesulfonate, and
    the reservoir being configured to be operatively connected to the tissue and to apply to the tissue at least one of: the liquefaction promoting medium and the drug.

12. The device of claim 11, the liquefaction promoting medium comprising 3-(decyl dimethyl ammonio) propane sulfonate and polyethylene glycol dodecyl ether in a buffered solution.

13. The device of claim 11, a total concentration of the non-ionic surfactant and the zwitterionic surfactant (w/v) in the liquefaction promoting medium being between about 0.5% to about 10%.

14. The device of claim 11, the non-ionic surfactant and the zwitterionic surfactant being in a ratio of between about 25:75 and about 75:25.

15. The device of claim 11, the non-ionic surfactant comprising one or more of: polyethylene glycol dodecyl ether, polyoxyethylene 23-lauryl ether, polyoxyethylene 2-cetyl ether, polyoxyethylene 10-cetyl ether, polyoxyethylene 20-cetyl ether, polyoxyethylene 2-stearyl ether, polyoxyethylene 10-stearyl ether, polyoxyethylene 20-stearyl ether, polyoxyethylene 2-oleyl ether, polyoxyethylene 10-oleyl ether, polyoxyethylene 100-stearyl ether, or polyoxyethylene 21-stearyl ether.

16. The device of claim 11, the abrasive material comprising at least one of: a fabric, abrasive crystals, diamond dust, a polymeric sponge, a natural sponge, an abrasive disc, or a brush.

17. The device of claim 11, the abrasive material including a sponge, the sponge being configured to store the liquefaction promoting medium.

18. The device of claim 11, further comprising a plunger operatively connected to the reservoir and configured to apply the liquefaction promoting medium from the reservoir to the tissue.

19. The device of claim 11, at least a portion of the device being disposable.

20. The device of claim 11, the device being sterile.

* * * * *